(12) United States Patent
Vardi et al.

(10) Patent No.: US 11,957,374 B2
(45) Date of Patent: *Apr. 16, 2024

(54) METHOD AND CATHETER FOR CREATING AN INTERATRIAL APERTURE

(71) Applicant: InterShunt Technologies, Inc., St. Louis, MO (US)

(72) Inventors: Gil M. Vardi, Town and Country, MO (US); Chris Minar, Excelsior, MN (US)

( * ) Notice: Subject to any disclaimer, the term of this patent is extended or adjusted under 35 U.S.C. 154(b) by 340 days.

This patent is subject to a terminal disclaimer.

(21) Appl. No.: 17/229,427

(22) Filed: Apr. 13, 2021

(65) Prior Publication Data
US 2021/0228227 A1    Jul. 29, 2021

Related U.S. Application Data

(63) Continuation of application No. 16/149,638, filed on Oct. 2, 2018, now Pat. No. 10,993,736, which is a
(Continued)

(51) Int. Cl.
*A61B 17/3205*   (2006.01)
*A61B 17/00*   (2006.01)
(Continued)

(52) U.S. Cl.
CPC .... *A61B 17/3205* (2013.01); *A61B 17/00234* (2013.01); *A61B 17/320016* (2013.01); *A61B 17/32053* (2013.01); *A61B 17/3478* (2013.01); *A61B 2017/00247* (2013.01); *A61B 2017/3458* (2013.01)

(58) Field of Classification Search
CPC ...... A61B 17/00234; A61B 17/320016; A61B 17/3205; A61B 17/32053; A61B 17/3478; A61B 2017/00247; A61B 2017/00252; A61B 2017/306; A61B 2017/32004; A61B 2017/320056; A61B 2017/320064; A61B 2017/3458

See application file for complete search history.

(56) References Cited

U.S. PATENT DOCUMENTS

| 4,018,228 A | 4/1977 | Goosen |
| 5,702,412 A | 12/1997 | Popov et al. |

(Continued)

FOREIGN PATENT DOCUMENTS

| WO | WO 02/47561 A1 | 6/2002 |
| WO | WO 2018/148456 | 8/2018 |

OTHER PUBLICATIONS

Barry A. Borlaug, The sHunt for better breathing in heart failure with preserved ejection fraction, European Journal of Heart Failure, 2014, 709-11, vol. 16.
(Continued)

*Primary Examiner* — Ryan J. Severson
(74) *Attorney, Agent, or Firm* — John M. Berns

(57) ABSTRACT

A catheter device 10 with a cutting structure or means 16 on the distal portion 14 is disclosed, along with a medical procedure for using the device. The catheter 10 is configured in such a way as to create a permanent interatrial aperture in the heart, including creating a permanent interatrial hole and/or removing tissue.

20 Claims, 23 Drawing Sheets

Related U.S. Application Data continuation of application No. 15/089,547, filed on Apr. 2, 2016, now abandoned, which is a continuation-in-part of application No. 14/738,802, filed on Jun. 12, 2015, now Pat. No. 9,814,483.

(60) Provisional application No. 62/012,212, filed on Jun. 13, 2014.

(51) Int. Cl.
*A61B 17/32* (2006.01)
*A61B 17/34* (2006.01)

(56) References Cited

U.S. PATENT DOCUMENTS

| | | | |
|---|---|---|---|
| 5,893,369 A | 4/1999 | LeMole | |
| 5,910,153 A | 6/1999 | Mayenberger | |
| 6,022,367 A | 2/2000 | Sherts | |
| 6,080,173 A | 6/2000 | Williamson et al. | |
| 6,428,555 B1 | 8/2002 | Koster, Jr. | |
| 6,468,227 B2 | 10/2002 | Zimmon | |
| 6,626,921 B2 | 9/2003 | Blatter et al. | |
| 6,695,859 B1 | 2/2004 | Golden et al. | |
| 6,743,244 B2 | 6/2004 | Blatter et al. | |
| 6,863,677 B2 | 3/2005 | Breznock | |
| 6,893,449 B2 | 5/2005 | Vargas et al. | |
| 7,056,294 B2 | 6/2006 | Khairkhahan et al. | |
| 7,144,405 B2 | 12/2006 | Vargas et al. | |
| 7,771,442 B2 | 8/2010 | Shriver | |
| 7,799,041 B2 | 9/2010 | Beane et al. | |
| 8,043,360 B2 | 10/2011 | McNamara et al. | |
| 8,070,708 B2 | 12/2011 | Rottenberg et al. | |
| 8,091,556 B2 | 1/2012 | Keren et al. | |
| 8,157,860 B2 | 4/2012 | McNamara et al. | |
| 8,172,896 B2 | 5/2012 | McNamara et al. | |
| 8,216,265 B2 | 7/2012 | Haunschild et al. | |
| 8,226,670 B2 | 7/2012 | Beane et al. | |
| 8,235,933 B2 | 8/2012 | Keren et al. | |
| 8,252,042 B2 | 8/2012 | McNamara et al. | |
| 8,328,751 B2 | 12/2012 | Keren et al. | |
| 8,460,372 B2 | 6/2013 | McNamara et al. | |
| 8,597,315 B2 | 12/2013 | Snow et al. | |
| 8,696,611 B2 | 4/2014 | Nitzan et al. | |
| 8,740,962 B2 | 6/2014 | Finch et al. | |
| 8,745,845 B2 | 6/2014 | Finch et al. | |
| 8,752,258 B2 | 6/2014 | Finch et al. | |
| 8,771,302 B2 | 7/2014 | Woolfson et al. | |
| 8,771,305 B2 | 7/2014 | Shriver | |
| 8,801,736 B2 | 8/2014 | Vardi | |
| 8,882,697 B2 | 11/2014 | Celermajer et al. | |
| 8,951,223 B2 | 2/2015 | McNamara et al. | |
| 8,956,377 B2 | 2/2015 | Khalapyan | |
| 9,005,155 B2 | 4/2015 | Sugimoto | |
| 9,034,034 B2 | 5/2015 | Nitzan et al. | |
| 9,205,236 B2 | 12/2015 | McNamara et al. | |
| 9,232,997 B2 | 1/2016 | Sugimoto et al. | |
| 9,277,995 B2 | 3/2016 | Celermajer et al. | |
| 9,358,371 B2 | 6/2016 | McNamara et al. | |
| 9,629,715 B2 | 4/2017 | Nitzan et al. | |
| 9,642,993 B2 | 5/2017 | McNamara et al. | |
| 9,649,480 B2 | 5/2017 | Sugimoto et al. | |
| 9,707,382 B2 | 7/2017 | Nitzan et al. | |
| 9,713,696 B2 | 7/2017 | Yacoby et al. | |
| 9,724,499 B2 | 8/2017 | Rottenberg et al. | |
| 9,757,107 B2 | 9/2017 | McNamara et al. | |
| 9,775,636 B2 | 10/2017 | Fazio et al. | |
| 9,814,483 B2 * | 11/2017 | Vardi | A61B 17/3478 |
| 9,943,670 B2 | 4/2018 | Keren et al. | |
| 9,980,815 B2 | 5/2018 | Nitzan et al. | |
| 10,045,766 B2 | 8/2018 | McNamara et al. | |
| 10,188,375 B2 | 1/2019 | McNamara et al. | |
| 10,639,060 B2 * | 5/2020 | Vardi | A61B 17/32053 |
| 10,993,735 B2 * | 5/2021 | Vardi | A61B 34/73 |
| 10,993,736 B2 * | 5/2021 | Vardi | A61B 17/3205 |
| 11,369,405 B2 * | 6/2022 | Vardi | A61B 17/3478 |
| 2001/0056248 A1 | 12/2001 | Zimmon | |
| 2002/0169377 A1 | 11/2002 | Khairkhahan | |
| 2006/0009715 A1 | 1/2006 | Khairkhahan et al. | |
| 2006/0111733 A1 | 5/2006 | Shriver et al. | |
| 2007/0185513 A1 | 8/2007 | Woolfson | |
| 2010/0010500 A1 | 1/2010 | Beane | |
| 2010/0057192 A1 | 3/2010 | Celermajer | |
| 2010/0121258 A1 | 5/2010 | Shriver | |
| 2010/0298850 A1 | 11/2010 | Snow et al. | |
| 2011/0071623 A1 | 3/2011 | Finch et al. | |
| 2011/0218480 A1 | 9/2011 | Rottenberg et al. | |
| 2011/0218481 A1 | 9/2011 | Rottenberg et al. | |
| 2011/0264128 A1 | 10/2011 | Mauch et al. | |
| 2011/0270239 A1 | 11/2011 | Werneth | |
| 2011/0295183 A1 | 12/2011 | Finch et al. | |
| 2012/0259263 A1 | 10/2012 | Celermajer | |
| 2012/0265296 A1 | 10/2012 | McNamara et al. | |
| 2012/0289882 A1 | 11/2012 | McNamara et al. | |
| 2012/0290062 A1 | 11/2012 | McNamara et al. | |
| 2013/0006281 A1 | 1/2013 | Golden et al. | |
| 2013/0178784 A1 | 7/2013 | McNamara et al. | |
| 2013/0218261 A1 | 8/2013 | Beane | |
| 2013/0267885 A1 | 10/2013 | Celermajer et al. | |
| 2013/0281988 A1 | 10/2013 | Magnin et al. | |
| 2014/0012257 A1 | 1/2014 | Epp. et al. | |
| 2014/0128795 A1 | 5/2014 | Keren et al. | |
| 2014/0128796 A1 | 5/2014 | Keren et al. | |
| 2014/0163449 A1 | 6/2014 | Rottenberg et al. | |
| 2014/0194971 A1 | 7/2014 | McNamara | |
| 2014/0277039 A1 | 9/2014 | Liberatore et al. | |
| 2014/0277043 A1 | 9/2014 | Jenkins et al. | |
| 2014/0277045 A1 | 9/2014 | Fazio et al. | |
| 2014/0277054 A1 | 9/2014 | McNamara et al. | |
| 2015/0359556 A1 * | 12/2015 | Vardi | A61B 17/320016 606/170 |
| 2016/0270810 A1 * | 9/2016 | Vardi | A61B 17/32053 |
| 2018/0064460 A1 * | 3/2018 | Vardi | A61B 17/32053 |
| 2018/0177516 A1 * | 6/2018 | Vardi | A61B 17/320016 |
| 2019/0029705 A1 * | 1/2019 | Vardi | A61B 17/320016 |
| 2021/0228227 A1 * | 7/2021 | Vardi | A61B 17/3478 |
| 2022/0323094 A1 * | 10/2022 | Vardi | A61B 17/32053 |

OTHER PUBLICATIONS

Michael A. Burke et al., Prognostic Importance of Pathophysiologic Markers in Patients With Heart Failure and Preserved Ejection Fraction, Circulation, Heart Failure, Dec. 23, 2013, 288-299, vol. 7.

Rainer Hoffmann, et al., Functional Effect of New Atrial Septal Defect After Percutaneous Mitral Valve Repair Using the MitraClip Device, Am J Cardiol, 2014: 113:1228-1233.

Lourdes R. Prieto, et al., Atrial Septostomy Using a Butterfly Stent in a Patient With Severe Pulmonary Arterial Hypertension, Catheterization and Cardiovascular Interventions, Sep. 12, 2006, 68:642-647.

Paul M. Seib, et al., Blade and Balloon Atrial Septostomy for Left Heart Decompression in Patients with Severe Ventricular Dysfunction on Extracorporeal Membrane Oxygenation, Catheterization and Cardiovascular Interventions, 1999, 46:179-186.

Lars Sondergaard et al., Transcatheter Treatment of Heart Failure with Preserved or Mildly Reduced Ejection Fraction Using a Novel Interatrial Implant to Lower Left Atrial Pressure, European Journal of Heart Failure, Jun. 24, 2014, 16:796-801.

Ignacio J. Amat-Santos et al., Left Atrial Decompression Through Unidirectional Left-to-Right Interatrial Shunt for the Treatment of Left Heart Failure: First-In-Man Experience with the new V-Wave Device, EuroIntervention, May 2014.

David Kaye, et al., Effects of an Interatrial Shunt on Rest and Exercise Hemodynaics: Results of a Computer Simulation in Heart Failure, Journal of Cardiac Failure, 2014, 20:3:212-21.

* cited by examiner

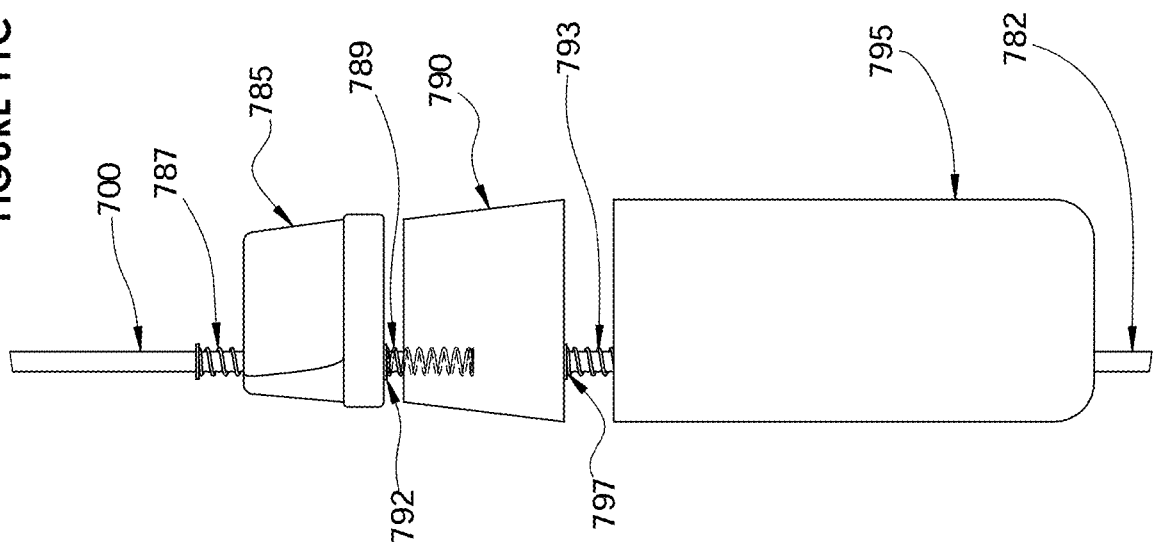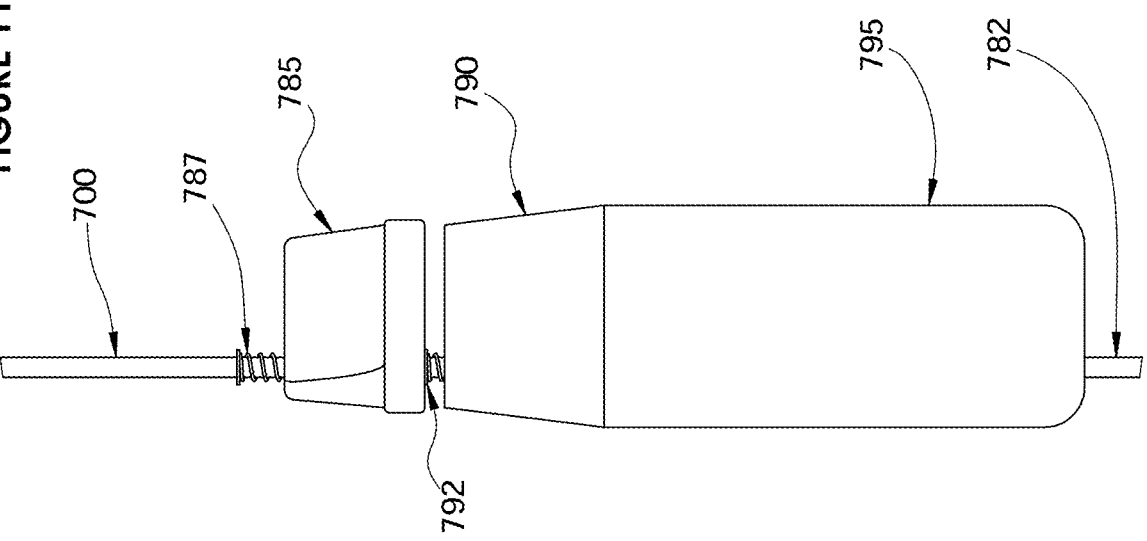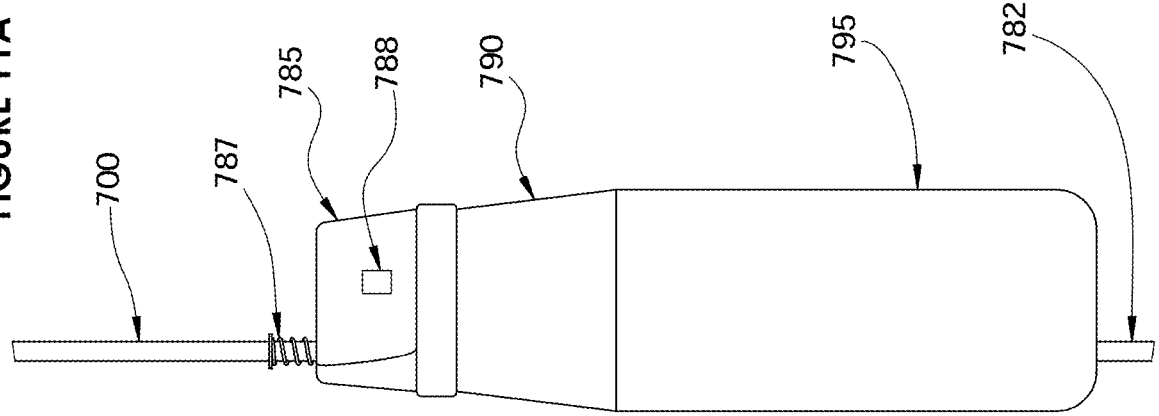

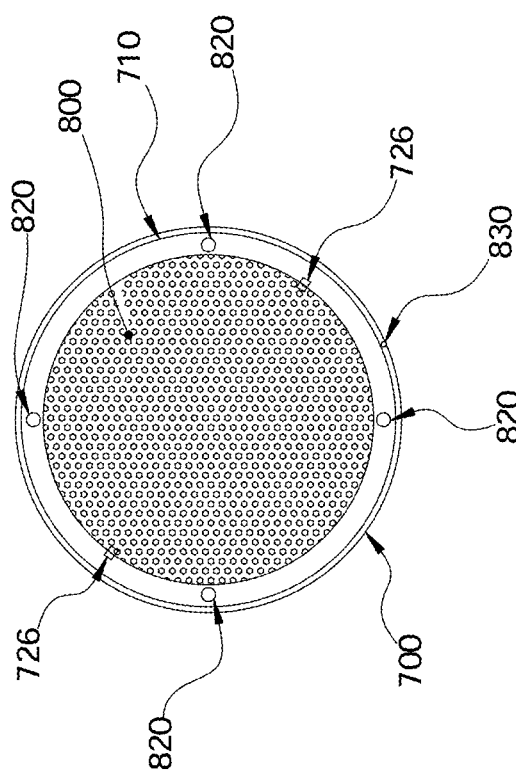
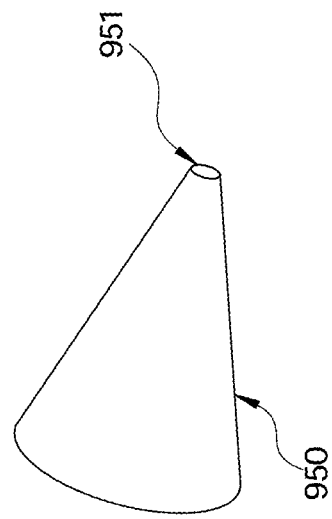
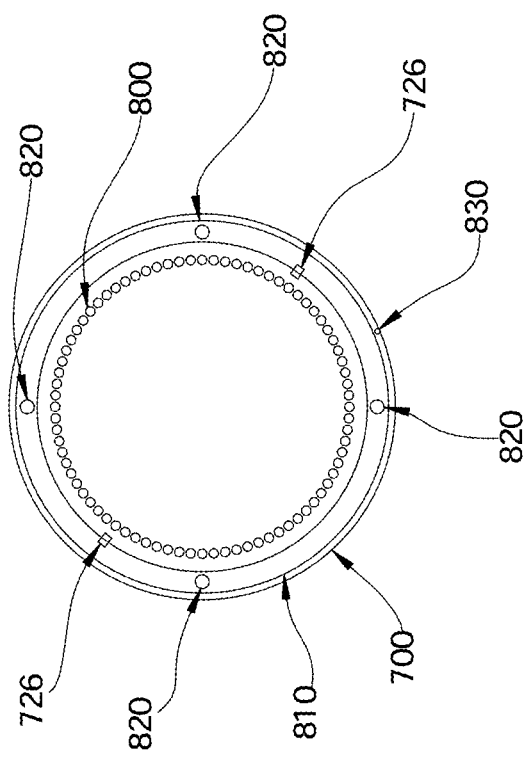
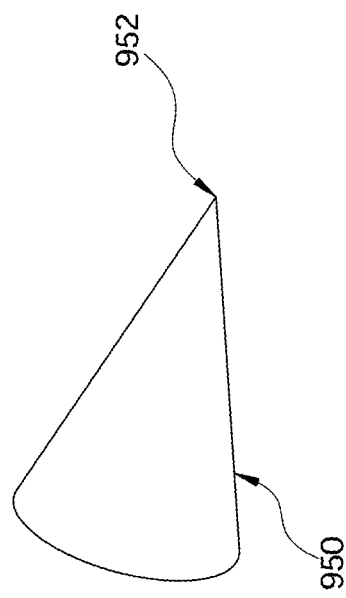
FIGURE 14B
FIGURE 15B
FIGURE 14A
FIGURE 15A

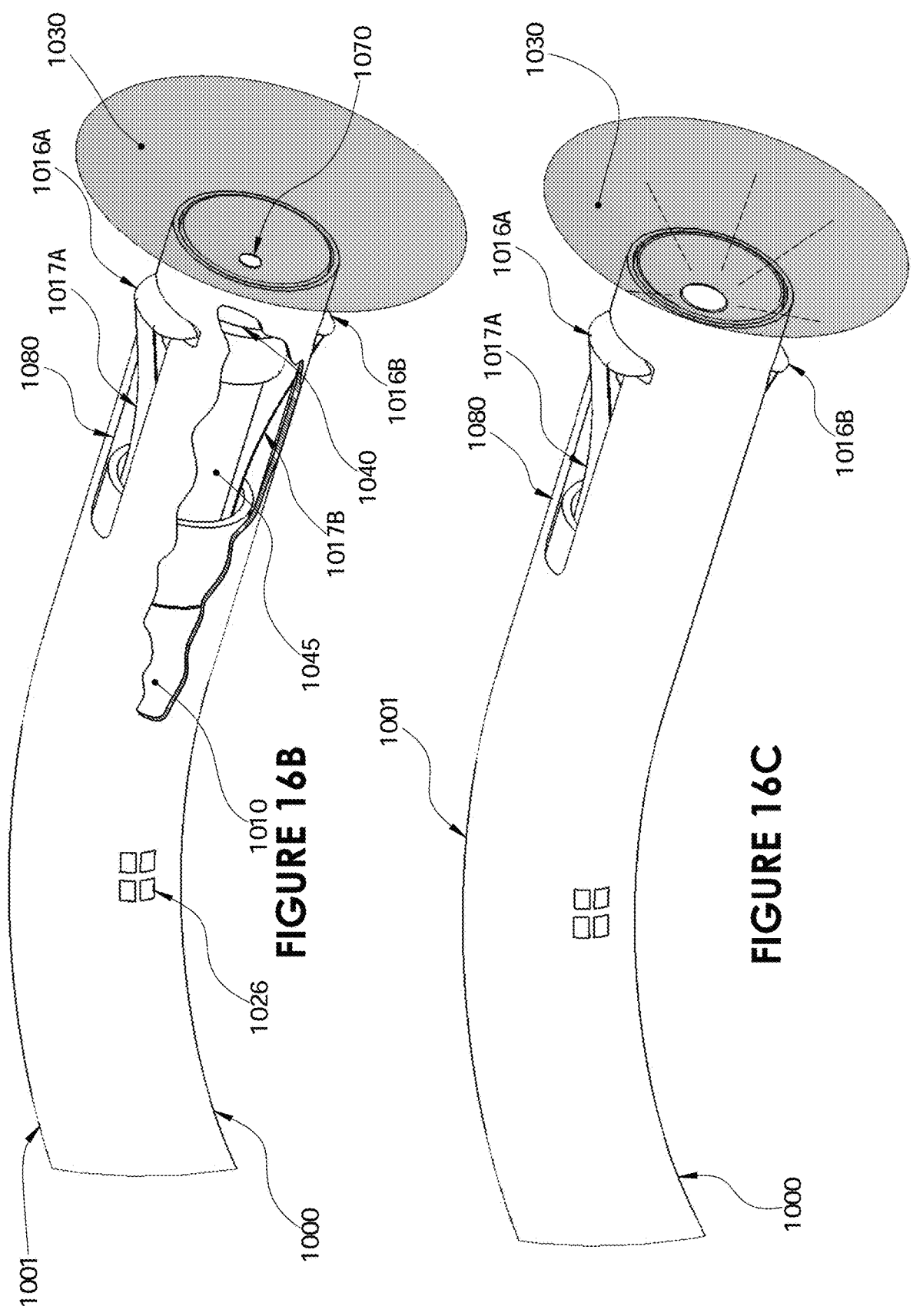

METHOD AND CATHETER FOR CREATING AN INTERATRIAL APERTURE

CROSS REFERENCE TO RELATED APPLICATIONS

This application claims the benefit of priority to U.S. patent application Ser. No. 16/149,638, filed Oct. 2, 2018, which claims priority to U.S. patent application Ser. No. 15/089,547, filed Apr. 2, 2016, which claims priority to U.S. patent application Ser. No. 14/738,802, filed Jun. 12, 2015, now U.S. Pat. No. 9,814,483, which claims priority to U.S. Provisional Application No. 62/012,212 filed Jun. 13, 2014, the entire disclosures of which are hereby incorporated by reference.

BACKGROUND OF THE INVENTION

Field of the Invention

The invention relates to medical devices and methods of medical treatment. The invention relates to a medical device and method of treatment used to create an aperture in the interatrial septum of a heart.

Background Art

There are some medical conditions that are treated by creating an opening between body chambers in order to create a connection between the chambers. The heart has an interatrial septum or wall that separates the left atrium and the right atrium. In certain heart failure patients (e.g., heart failure with preserved ejection fraction (diastolic dysfunction)) there is a need to allow blood flow from the left atrium to the right atrium to reduce left atrial pressure. Likewise, certain other heart diseases and conditions, such as congenital heart diseases and pulmonary hypertension may be treated by making an interatrial opening; however, the goal is to create a right-to-left shunt to reduce the high right-sided pressure.

One procedure uses a balloon to create a hole in the septum. However, it has been found that a hole created in this manner may not stay open and after a period of time may spontaneously close. This renders this particular therapeutic solution temporary.

A few other devices have been proposed in order to overcome the temporary solution of using a balloon. Implanting a stent in the interatrial septum has been used as a treatment for elevated pressure in one atrium by allowing blood to flow through the opening to the other atrium to reduce atrial pressure. A heart surgeon implants the stents in certain predetermined sizes in an effort to control the amount of blood flow between the atria. Thus, one device is to use a stent to keep the hole open. Another device uses a valve inserted into the septum that keeps the hole open and also assists in controlling blood flow. Significant drawbacks to these devices are that they are permanent implants that can promote thrombosis and are potentially subject to infection.

Another major drawback of these devices is that they are not capable of removing a segment of the septum. The benefit of removing a segment of the septum is that aperture will be less likely to close spontaneously. The stents may also become spontaneously dislodged and embolize and cause cardiac damage or blockage of blood flow.

Therefore, it would be desirable to have a medical device that is capable of creating an incision or an opening in the interatrial septum of the heart to alleviate pressure between chambers in the heart that does not suffer from the limitations of prior devices or procedures. It would be advantageous to have a catheter that can create various slits, openings, or apertures in the interatrial septum in a predetermined orientation. It would also be advantageous to have a catheter that may be easily manipulated to remove a section of the interatrial septum to form a permanent aperture that is less likely to spontaneously close.

BRIEF SUMMARY OF THE INVENTION

The present invention solves these needs by providing a medical device that creates a hole in the interatrial septum and/or removes tissue as needed. In one embodiment a medical device assembly includes a sheath that includes an elongated shaft with a first bend region, a central lumen, a distal end with a distal end lumen and a first steering wire, the steering wire having a first position and a second position, wherein at the first position the first bend region is substantially linear, and wherein at the second position the distal end and the distal end lumen of the sheath are substantially perpendicular to an inter atrial septum. The assembly may also include a catheter inside the sheath, the catheter including a shaft having a central lumen. The assembly also includes a shaped blade that includes a blade cutting edge that is oriented at a substantially right angle to the longitudinal axis of the sheath when the sheath is oriented substantially perpendicular to the inter atrial septum, and is adapted to cut a 3 mm or larger durable aperture in the interatrial septum, a tissue articulator having a first setting and a second setting, the tissue articulator being adapted to hold the interatrial septum against the shaped blade for cutting while in the second setting, and an actuator operably connected to the tissue articulator, the actuator having a first position and a second position, wherein when the actuator is in the second position the tissue articulator holds the interatrial septum against the shaped blade.

In another embodiment the assembly includes a marker to identify the catheter location on a visualization system. In another embodiment the articulator is a suction device.

In one embodiment the assembly does not cross the interatrial septum. In particular, while a tissue grabbing element may retain the tissue or enter it, such as a hook, no element such as a guidewire or needle crosses the septum. In another embodiment the articulator is adapted to retain the interatrial septum from only the same side of the interatrial septum as the shaped blade cuts the interatrial septum. The shaped blade can be a circular blade, a square blade, a triangular blade, a sawtoothed blade, a franseen blade, or a polygonal blade.

In another embodiment the assembly also includes a tissue removal device. The articulator can be the tissue removal device. The tissue removal device can be adapted to remove or hold a first tissue portion so that the articulator can hold a second tissue portion against the blade and make a second cut on that second tissue portion. In another embodiment the tissue removal device is a vacuum that removes the first tissue portion.

In one embodiment the assembly further includes an anchor. The anchor can attach to a tissue, such as for example the interatrial septum. Alternatively, the anchor can attach to the patient's exterior or the patient's bedside. In another embodiment a robotic system provides the anchoring mechanism by securely holding the catheter or handle. In another embodiment the assembly further includes an orthogonal guide, the orthogonal guide adapted to hold the shaped blade in an orthogonal position to the interatrial septum.

In another embodiment the medical device assembly includes a sheath that includes an elongated shaft with a first bend region with a first preshaped bend, a central lumen and a distal end with a distal end lumen. The first preshaped bend is adapted to position the distal end and the distal end lumen of the sheath substantially perpendicular to an inter atrial septum. The device further includes a catheter inside the sheath. The catheter includes a shaft with a central lumen, a shaped blade that includes a blade cutting edge that is oriented at a substantially right angle to the longitudinal axis of the sheath when the sheath is oriented substantially perpendicular to the inter atrial septum, and is adapted to cut a 3 mm or larger durable aperture in the interatrial septum. The assembly also includes a tissue articulator with a first setting and a second setting, the tissue articulator being adapted to hold the interatrial septum against the shaped blade for cutting while in the second setting. The assembly may also include an actuator connected to the tissue articulator, the actuator having a first position and a second position, wherein when the actuator is in the second position the tissue articulator holds the interatrial septum against the shaped blade.

In another embodiment the assembly includes a suction opening configured to provide suction in the approximate area of the shaped blade. In another embodiment the tissue articulator is a tapered cone having a proximal face, the proximal face being adapted to retain a tissue.

In another embodiment a method of treating a heart is disclosed. The method includes the steps of inserting a catheter into the right atrium of the heart. In one embodiment the catheter includes a shaft, a distal catheter lumen, a shaped cutting blade arranged around the distal catheter lumen, a tissue articulator, the tissue articulator having a first position and a second position, an actuator connected to the tissue articulator, and a steering mechanism. In one embodiment the catheter acts entirely from the right atrium. Thus, while the catheter is in the right atrium, the physician actuates the actuator to move the tissue articulator into a second position that holds the tissue against the shaped cutting blade, cuts an aperture in the interatrial septum between the right atrium and the left atrium, and removes a cut tissue from the right atrium.

In another embodiment, the method further includes the step of attaching a tissue removal device to a portion of the interatrial septum. In another embodiment the method further includes the step of pulling the attached tissue into a lumen at a distal end of the catheter shaft using suction.

In one embodiment, the medical device includes a catheter with a catheter shaft that has a central lumen and a distal catheter lumen. The catheter also has a shaped blade around the distal catheter lumen. The blade is adapted to cut an area of tissue to create an aperture in a tissue. The catheter also has a tissue articulator, the tissue articulator having a first position and a second position, is configured to move with respect to the shaped blade, and is adapted to hold the tissue against the shaped blade for cutting while in the second position. The catheter also includes an actuator connected to the tissue articulator, the actuator having a first position and a second position, wherein when the actuator is in the second position the tissue articulator holds the tissue against the shaped blade.

In another embodiment the medical device of includes a sheath adapted to protect tissue from the shaped blade before the shaped blade is deployed. The shaped blade may be a circular blade, a square blade, a triangular blade, or a polygonal blade. Likewise, the blade can provide an elongated slit with a small width and a radius on each end—to create a structure that has a small sectional area under low pressure, but increases in area with a high pressure differential. In another embodiment the medical device includes a tissue removal device. The tissue removal device may include a hook, a balloon, or an expandable basket. In one embodiment the distal catheter lumen is larger than the central catheter lumen.

In one embodiment the medical device includes multiple blades on the exterior of the catheter shaft. The blades can be arranged apart from each other circumferentially around the catheter shaft and extending outward from the catheter shaft. Each blade may be attached to the catheter shaft by, for example, a pin and be adapted to expand away from the catheter shaft when actuated, e.g., by moving an actuator.

The medical device may include a first radiopaque marker on the distal end of the catheter. It may also, or in the alternative, include an ultrasound marker on the distal end of the catheter.

The medical device in one embodiment includes a sheath. The sheath may also have a radiopaque marker on the distal end of the sheath. The radiopaque markers may be the same or different and may be configured to identify when the catheter has exited the sheath.

In another embodiment the medical device further includes a suction opening configured to provide suction in the approximate area of the cutting blade.

The tissue articulator can be a tapered cone having a proximal face, the proximal face being adapted to retain a tissue, and may be adapted to fit within the distal lumen of the catheter shaft.

In another embodiment, the medical device includes a tenting device adapted to tent a target tissue into the distal lumen of the catheter such that a larger portion of the target tissue may be cut by the cutting device.

In one embodiment the shaped blade is formed of a memory metal, the memory metal being biased to expand when removed from the catheter or the sheath to provide a cutting surface substantially larger than the diameter of the catheter.

In another embodiment the medical device includes a catheter with a catheter handle, a catheter shaft, the catheter shaft having a central lumen and a distal catheter lumen, a circular blade around the distal catheter lumen, a tissue removal device, a guidewire adapted to pass through the central catheter lumen, and includes a sheath adapted to protect tissue from the circular blade before the circular blade is deployed In another embodiment the invention is a method of treating congestive heart failure including the steps of inserting a catheter into the right atrium of the heart, the catheter including a shaft, a distal catheter lumen, a shaped cutting blade arranged around the distal catheter lumen, a tissue articulator, the tissue articulator having a first position and a second position, an actuator connected to the tissue articulator. The embodiment further includes the steps of crossing the interatrial septum, actuating the actuator to move the tissue articulator into a second position that holds the tissue against the shaped cutting blade, cutting an aperture in the interatrial septum between the right atrium and the left atrium, removing a cut tissue from the right atrium.

In one embodiment the method further includes a step of attaching a tissue removal device to the interatrial septum. In another the method further includes a step of pulling the attached tissue into a lumen at a distal end of the catheter shaft. The method may also include a step of expanding the cutting device to a diameter greater than the diameter of the catheter.

BRIEF DESCRIPTION OF THE DRAWINGS

FIG. 11A is a partial perspective view of a catheter handle constructed according to the present disclosure;
FIG. 11B is a partial perspective view of a catheter handle constructed according to the present disclosure;
FIG. 11C is a partial perspective view of a catheter handle constructed according to the present disclosure;
FIG. 14A is a cross sectional view of the distal end of a catheter constructed according to the present disclosure;
FIG. 14B is a cross sectional view of the distal end of a catheter constructed according to the present disclosure;
FIG. 15A is a partial perspective view of the distal end of a catheter constructed according to the present disclosure;
FIG. 15B is a partial perspective view of the distal end of a catheter constructed according to the present disclosure;
FIG. 16B is a partial perspective view of a catheter constructed according to the present disclosure;
FIG. 16C is a partial perspective view of a catheter constructed according to the present disclosure.

DETAILED DESCRIPTION OF THE PREFERRED EMBODIMENTS

Figure 1:
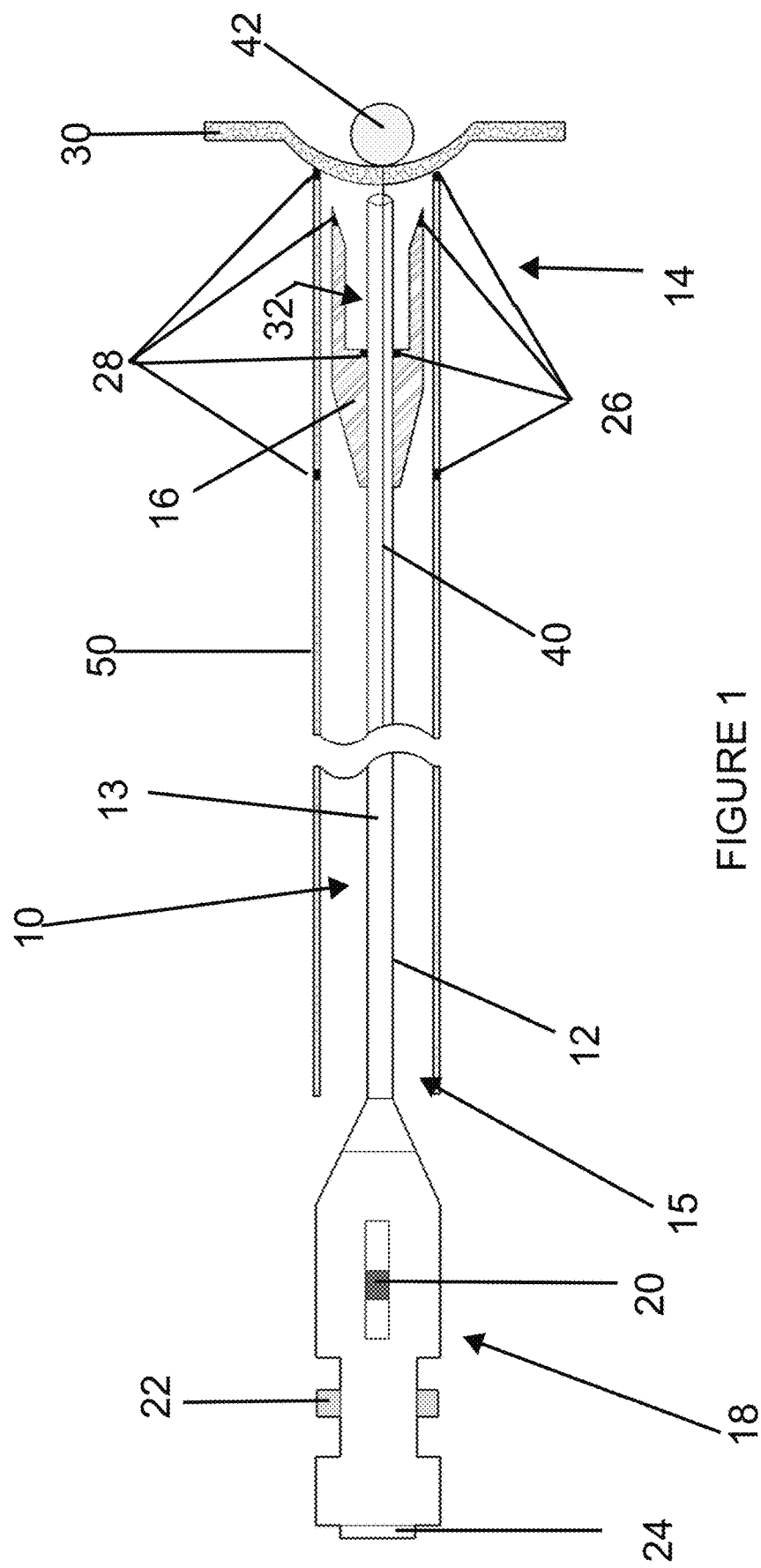
FIG. 1 is a partial perspective view of a catheter constructed according to the present disclosure.

In general, the invention comprises a medical procedure and corresponding medical devices for therapeutic surgical procedures. In particular, the invention comprises a method of creating an aperture between heart chambers for blood flow and devices for creating that aperture. In this context, an aperture is a created space or gap large enough to allow significant blood flow between the two chambers it connects, to treat or improve heart failure, pulmonary hypertension, or similar diseases, without the use of an implanted device.

In order to treat congestive heart failure, it must first be diagnosed. In particular diagnosis may comprise listening to the lungs for signs of congestion, measurement of vital signs, a chest x-ray of the lungs, electrocardiogram (ECG), an echocardiography and other imaging modalities to assess cardiac output, ventricular contraction and filling, atrial size, and cardiac valve function, etc., insertion of a central venous catheter and measurement of pulmonary capillary wedge pressure (PCWP), a blood tests, e.g., to check for chemicals such as brain natriuretic peptide (BNP and N-terminal pro-B-type natriuretic peptide (NT-proBNP), a stress test, cardiac catheterization and/or an MRI or CT scan. In addition, transthoracic echocardiography (TTE) or transeophogeal echocardiography (TEE) may be used to confirm the absence of any current holes between the chambers of the heart.

Once congestive heart failure is diagnosed a course of treatment will be designed. While it is possible to treat congestive heart failure with surgery, implants, or other methods, herein disclosed is a method of advantageously treating congestive heart failure without surgery and without leaving behind an implant.

The disclosed procedure preferably begins with a percutaneous entry into a vein, preferably the femoral vein in the groin region. It is also possible to gain entry via a jugular or subclavian vein or neck vein. Typically a sheath with a guide wire is inserted through the percutaneous entry and maneuvered by the physician to the right atrial chamber. The sheath used in the present invention may be steerable, for example controlled by pull wires which extend from its distal region to a handle at its proximal end, the handle having one or more actuators. Likewise the sheath may be pre-curved or pre-bent such that it will automatically orient towards the interatrial septum once it reaches the right atrium.

Once in the right atrium, the physician will identify the portion of the interatrial septum at which he will create the interatrial aperture. Typically, this will be at the fossa ovalis. Because the fossa ovalis is thinner than the remainder of the interatrial septum, it will be easiest to cut an aperture at its location. To identify the fossa ovalis the physician may employ one or more means of tissue thickness sensing. For example the physician may use an electrode and test for impedance changes, may employ one or more ultrasound methods, or may simply test for tenting. For example, the physician may apply a small amount of pressure to the interatrial septum and search for tenting in the tissue. Once the physician locates the spot where the tissue easily tents, e.g. the fossa ovalis, the physician will deploy the present device to create the aperture. In some embodiments it is desirable to cross into the left atrium. As such, the physician will create a small puncture in the septum using a transseptal device. For example a brockenbrough needle, a BRK needle, or another transseptal device may be used for crossing the septum into the left atrium. Once there, the guidewire is threaded through the interatrial septum puncture and the distal end of the guidewire is left in the left atrium. The proximal end of the guidewire will remain outside of the body, with its entry point at the femoral vein. As with the sheath, the guidewires described herein may be pre-curved or pre-bent such that they will automatically orient towards the interatrial septum once reaching the right atrium.

Depending on the therapeutic catheter that will be used in the latter portion of this procedure it is possible that a guidewire may not be required, and in some cases that the device may not cross into the left atrium at all. In such instances a transseptal device may not be necessary either. If the catheter to be used to form the interatrial aperture is designed to create its own transseptal crossing or create an aperture without crossing the septum, the guidewire or transseptal device may be avoided, potentially saving cost and time.

With the guidewire in place, the sheath may be removed. If so, a surgical catheter and/or a sheath will be provided and directed over the guidewire into the right atrium. Once there the therapy catheter, further to the surgical mechanisms disclosed in detail below, will create a durable interatrial aperture.

During the procedure the physician will monitor the location of the catheter and/or sheath as well as the progress of the cut, the nature of the aperture, or other procedure details via fluoroscopy, MRI, ultrasound, or transesophageal echocardiography, intracardiac echocardiography (ICE) or similar tracking or visualization technology for guidance. Toward this end, it is preferred that the catheter includes radiopaque or ultrasound markers as described in further detail below. Likewise, the physician may monitor the location of the catheter and/or sheath as well as the progress of the cut, the nature of the aperture, or other procedure details via a camera, such as a CCD camera. In the latter case it may be advantageous to apply a hood over the operation region, empty the hood of blood and replace it with saline, such that the procedure may be visually monitored. This hood may also be used, as discussed in detail below, to provide an orthogonal orientation to the cutting blade and the target tissue. Other location systems are possible, including MRI, electroanatomical navigation systems such as EnSite®, Carto®, or MediGuide® systems, along with the corresponding sensors on the introducer 50 and catheter 10.

The interatrial aperture will be created by one of two mechanisms or a combination thereof. First the surgical catheter will create an aperture. The catheter could use a cutting blade or other means disclosed herein to create an aperture or cut pattern in the interatrial septum such that a sufficient flow of blood may occur between the two atria. For example, the catheter may cut an X— pattern aperture in the septum. Doing so leaves flaps that will open and close depending on the pressure differential between the two atria. Likewise the catheter may create a circular or semi-circular hole in the septum. Such openings may have benefit in determining the direction of blood flow in order to maximize left-to-right and minimize right to left flow especially in patients with combined left and right heart failure as occurs in patients with HFrEF. Similarly, an elongated hole such as a 1 mm wide slit with radiused ends may have low csa and shunting with low pressure differential and increased csa and shunting with higher pressure differential. The utility of such a design may have particular value with HFrEF patients.

Second the catheter may remove tissue. For example in creating a shaped aperture the catheter may utilize a cutting blade to cut the tissue from the septum and remove it from the body. Loose tissue removal is critical so that any loose tissue does not remain in the atria, creating a substantial risk of stroke due to embolization.

In either mechanism, the physician preferably engages the target tissue with a distal portion of the device, such as a tissue articulator. The tissue articulator may penetrate into or through the tissue, and then be actuated (e.g., via an actuator on the catheter or sheath handle) to hold the tissue against the cutting blade. Alternatively, the articulator may hold the tissue and the blade may approach it for cutting the tissue. Thus, the articulator works with the blade for one or more purposes, it may hold the tissue in place, guide the blade to the desired portion of the tissue, hold the catheter in place and on target, retain any loose tissue, or create an initial opening in the tissue for the device to pass into.

In a preferred embodiment, the tissue articulator passes through the tissue as the catheter or sheath is advanced. Alternatively, an actuator, (e.g., an actuator on a handle, or simply a movable lumen/guide within the medical device) may be in or moved to a first position that advances or locates the tissue articulator forward away from the cutting blade. This advancement (or a separate advancement) may push the tissue articulator through the tissue. Once the tissue articulator is in place, either by actuation or mere advancement, the actuator is activated to a second position that causes the articulator or blade to engage the tissue. The second position (or a third position) may also pull the tissue into a lumen in the catheter or sheath, tenting it so that a larger aperture may be cut.

For proper utility in patients who need transeptal shunting of blood it is critical that the aperture be "durable" such that it will stay open for a long period of time and even permanently, as defined below. The shunt size can be titrated by measuring the left atrial pressure either at rest or with exercise. Likewise, the doctor can measure oxygen saturation in the right atrium, or cardiac output. The medical device of the present invention preferably includes means to measure pressure and/or oxygen saturation, such as a sensor or via fluid removal for testing.

In one version of the procedure, the device crosses the septum into the left atrium and records the resting pressure (or with exercise). AT this point the durable aperture is cut. Then, the pressure measurement is again performed and it is determined if the aperture is sufficient. One advantage of the present procedure and device is the ability to measure success during the procedure, and adjust the shunt size as needed, rather than waiting until post procedure and having to reenter the patient.

In certain patients it is preferred that the hole be at least 3 to 12 mm, preferably 4 to 10 mm, or 6 to 8 mm, in diameter for the desired clinical benefit. In other patients a higher pressure may indicate that a smaller aperture be formed, e.g., 0.5 to 5 mm, or 2-3 mm. However, such small hole sizes have increased risks of closing, tissue healing, and plugging, and are accordingly unlikely to be durable absent exceptional circumstances. The interatrial shunt lowers LA pressure especially during exercise in heat failure patients. The left-to-right shunting can cause a decrease in left ventricular (LV) CO and an increase in right ventricular CO. The reduction in LA pressure, however, might allow patients to achieve a higher level of exertion leading to higher heart rate and thus an increase in LV CO. Furthermore, increases in RA pressure and pulmonary arterial pressure can occur, but in HF patients, despite the increase in RV CO, a reduction in pulmonary venous pressure can actually occur. The size of the shunt can determine the extent of all these hemodynamic effects, and enable a Qp/Qs ratio sufficient to reduce LA pressure without RV overload. The clinically necessary size will vary from patient to patient. Subsequent to the procedure the physician will monitor the patient at one month, three-month, and six-month exams to determine if the size of the hole has shrunk. While it is anticipated that healing tissue may slightly shrink the aperture on the order of 1 to 2 mm, if the aperture remains open at six months it is considered "permanent" or durable for purposes herein. It is also desirable that the aperture be visible on an echocardiogram so that it can be readily measured. Ultimately, for these patients, safety and a proper balance of blood hemodynamics, oxygenation will be used determine the aperture size, shape and quantity.

The tissue may be removed by a device using, for example, suction or grasping mechanisms. In a preferred embodiment the catheter, e.g., the tissue articulator, will pull the tissue into the blade to positively retain it and keep it from releasing into the heart. In addition to its utility for tissue removal, the suction and grasping mechanisms may also be extremely useful for positioning the device, and retaining the device in the desired position during operation. Additionally, suction may aid in determining that the blade is orthogonal to the tissue, e.g., that it has the proper orientation for cutting. For example, if under light suction in the blade's lumen a seal is formed between the blade and the tissue, the blade may be determined to be at a proper orientation to the tissue for cutting a durable aperture. Likewise, sensors on the grasping mechanism may be able to determine how far into the tissue the grasping mechanism is. If four hooks, for example, all 90 degrees apart, have penetrated the tissue to the same depth, it may be determined that the device is orthogonal to the tissue.

Creating a hole in the heart without leaving behind an implant avoids the need for anticoagulant therapy, lowers the risk of infection, and avoids the use of an implant that may come loose over time. In addition the procedure is substantially simpler than installing and leaving behind an implant. Due to the lack of an implant, there are no risks of MRI compatibility, no risk of device failure or fracture. It is easier to close the aperture if needed absent a device, and the overall total cost of care is lower. No implant means faster and safer crossing of the septum during future catheter based surgical procedures, such as treating atrial fibrillation or ventricular tachycardia. Finally, the procedure is faster and will allow for a more efficient use of hospital facilities and physician time.

There are multiple ways to determine if the aperture is large enough to be efficacious. Subsequent to the procedure the physician may do so by, e.g., examining the aperture on an echocardiogram visually and using doppler, calculating the degree of shunting, performing an exercise tolerance procedure, by measuring the ejection fraction, by measuring the wedge pressure, oxygen saturation, or other means. It is preferred that a clinical evaluation be conducted such as a walking test, to determine the practical effect on the patient. The invention allows for easier adjustment of aperture size compared to similar solutions. In particular, if the aperture size is too small, an additional aperture may be created, or the existing aperture can be expanded. Because certain clinical evaluations can be performed immediately after the patient is first treated, it may be possible in many cases to leave the catheter in place during the evaluation, use the same catheter to create the second aperture or increase the size of the existing aperture, and thereby avoid a second procedure. This determination can be performed by having the patient exercise using upper body exercise device and measuring the LA pressure prior to and during exercise. If the reduction is not sufficient to reduce PCWP then a second hole can be created and the exercise evaluation repeated. This is not possible with the prior art devices.

Also disclosed is a medical device for creating the aperture between the left atrial chamber and the right atrial chamber. The medical devices have dimensional requirements depending on several factors. First, the length of the device will depend on its point of entry. For example, a catheter that will be used in a percutaneous entry at the femoral vein and which must reach to the right atrium will typically be at least 120 cm long and more preferably 140 cm. A catheter that will enter the body at a different location in many cases will be substantially shorter. The more lengthy and torturous the path the catheter must take, the stiffer the catheter body may need to be, and the more likely the catheter will be to require stiffening elements such as a stainless steel or nitinol braid. The need for a stiffer catheter is particularly acute for the present device. It must first take a long path through the body to the right atrium, then turn at a sharp angle to address the interatrial septum, and then project enough force along that turn to push the cutter through the interatrial septum. It is difficult to project that force along the length of the catheter body, which runs from the groin region to the heart, and then successfully get the force to take the turn toward the septum without first pushing the catheter higher inside the heart rather than to the side toward the septum. Accordingly, unlike many prior art surgical catheters, the present device may require a substantially stiffer body, provided by braiding, nitinol stiffening devices, or multiple catheter layers. Another reason for a stiff catheter is, in combination with ridged proximal handle/end fixation (bed rail), the clinician can make fine (submillimeter) movements to the distal tip with respect to the tissue Typically a thinner catheter is preferred, so long as the cutting elements are sufficiently sized to create a large enough interatrial aperture. For example, it would be preferred to have a catheter shaft of nine French however there is always a trade-off between a small diameter device and the need to create a sufficiently sized interatrial aperture. Thus it may be advantageous to have a small diameter shaft for the bulk of the catheter length combined with a somewhat larger distal working end on the catheter or an expandable distal working end that has a small diameter upon insertion to the vein and can be expanded once in the right atrium and then collapse back to a smaller diameter for removal through the vein. On the proximal end of the catheter it is advantageous to have an easily manipulable handle so that the physician can direct the catheter into its desired location and control the cutting device.

With reference to FIG. 1, the catheter 10 comprises an elongated catheter shaft 12 having a distal end 14 and a proximal end 15. Proximal end 15 includes a handle 18. The handle 18 comprises a first actuator 20 and a second actuator 22. Handle 18 further includes a fluid port 24 and an electrical connection (not shown). Catheter 10 may further include pull wires attached to an actuator for actuating distal elements, moving a lumen or shaft, steering, or the like. Catheter 10 may be pre-curved or pre-bent such that it will automatically orient towards the interatrial septum once it reaches the right atrium.

It may further include irrigation ports and the like. Catheter 10 further includes radiopaque markers 26 in a designed pattern that allows the physician to determine the location and orientation of the catheter 10 in the patient and the orientation of the different components of the device relatively to each other. Catheter 10 may further include ultrasound markers 28 again in a designed pattern such that the physician may locate the catheter 10 in the patient on ultrasound imaging.

The elongated catheter shaft 12 is preferably hollow, having a lumen 13 that has the ability to pass a guidewire 40 through it. Catheter 10 is designed to work in conjunction with an introducer 50. Introducer 50 may either extend the entire length from the percutaneous incision to the left atrium of the heart, or may only cover a portion of catheter 10.

The distal end 14 of catheter 10 comprises a cutting means 16. In a first embodiment the cutting means 16 is a razor like member formed of steel or another suitable metal or material adapted to cut a thin tissue. Toward this end the cutting means may be very thin so that it cleanly and easily pierces the thin tissue. In those embodiments where cutting means 16 has a sharp edge exposed at the end of the catheter 10, it is it is preferred that the introducer 50 cover and protect the vein and other tissue from the cutting means 16 until the catheter 10 is delivered in place and actuated by the physician to cut the target tissue. In other embodiments a cone (not pictured) or other distal element may cover or sit flush with the cutting blade 16 so that the blade is protected until actuation.

The cutting means 16 may be a serrated blade which will allow for a lower cutting force. Likewise the cutting means 16 may comprise a vibrating blade to likewise allow for a lower cutting force.

The introducer 50 is typically a hollow sheath. Introducer 50 may include braiding along the outer cylinder to provide stiffening. Introducer 50 may further include a handle at the proximal end, an actuator, and pull wires attached to the actuator for steering, irrigation ports and the like. In particular, pull wires may be strongly advantageous. Unlike prior art devices which create a hole by energy sources or by implanting a device, the present device may find that significant pressure on the cutting blade 16 is necessary. Accordingly, in a preferred embodiment the sheath wall, and/or the catheter wall are braided or reinforced to provide a stiffer device.

Likewise, because the pressure must be transmitted from the length of the introducer or catheter, that pressure will initially push the cutting edge and the entire catheter along rather than through the septum. For example, in a femoral vein entry procedure, the catheter is initially pushed upwards rather than towards the left atrium. Providing stability and steerability in either the introducer or the catheter may greatly reduce this upward pressure and redirect the force towards the interatrial septum 30 to provide a proper cut.

Likewise, providing anchoring means or stabilizing means can prevent the catheter and the cutting blade from shifting and allow a clean cut in the desired location. Thus, in one embodiment the assembly further includes an anchor. The anchor can be an in vivo, such as a component at the end of the catheter that hold the catheter in place. For example, hooks, corkscrews, or a forceps may hold the tissue tightly. Alternatively, the balloon, pigtail, or other tissue retention means described herein may serve as an anchor.

In another embodiment the anchoring mechanism is outside the body. Thus, the anchor can attach to the patient's exterior or the patient's bedside and hold the proximal portion of the catheter securely, e.g., a handle brace that attaches to the patient's bedside. In another embodiment a robotic system provides the anchoring mechanism by securely holding the catheter or handle. Of course, multiple anchoring means may be employed. An anchor is important because very precise control of the catheter and the cutting means are important for safe and successful procedures. Placing the cutting means in the wrong location or making it at the wrong angle results in a much more difficult cut, or a less safe cut as the cutting means may perforate the atrial wall on the other side of the septum. Thus, it is advantageous to have movement control down to the 1 mm level. Of course, providing a visualization system that has a similar resolution provides a synergistic effect with having a high degree of movement control.

In another embodiment the assembly further includes an orthogonal guide, the orthogonal guide adapted to hold the shaped blade in an orthogonal position to the interatrial septum.

Introducer 50 further includes radiopaque markers 26 in a designed pattern that allows the physician to determine the location and orientation of the introducer 50 in the patient. Introducer 50 may further include ultrasound markers 28 again in a designed pattern such that the physician may locate the introducer 50 in the patient on ultrasound imaging. Preferably, the radiopaque markers 26 and ultrasound markers 28 on the catheter and introducer are distinguishable from each other and accordingly the physician is able to determine which markers are on the catheter in which markers are on the introducer readily such that the physician is able to determine the spatial relationship of the two devices, the catheter 10 and the introducer 50.

This spatial relationship allows the physician is to determine when the catheter 10 exits the introducer 50 and the cutting mechanism 16 is active, as well as determine the location and orientations of the devices at all times.

Ideally, in operation the introducer 50 is positioned next to or near a target tissue 30. Specifically the introducer 50 is located near the interatrial septum. The introducer 50 may be so located through a physician's experience touch and feel, or using the markers 26, 28 in conjunction with imaging system. Other location systems are possible, including MRI, electroanatomical navigation systems such as EnSite®, Carto®, or MediGuide® systems, along with the corresponding sensors on the introducer 50 and catheter 10. The sensors 26, 28, may advantageously be located at the tip of the sheath or the catheter. In this embodiment the sensors may identify on a visualization system when the sheath is orthogonal to the tissue 30. Likewise, electrodes, pressure sensors, fiber optics, a camera, or the like may sense the tissue contact or proximity, and may thus identify when the sheath is in contact with the tissue, and also when it is orthogonal to the tissue. In such a case it may be advantageous to have two such sensors 180 degrees apart, or preferably 4 or more sensors 90 degrees apart.

While proper alignment of the catheter or sheath is discussed above, and is important in most embodiments, it is understood that in those embodiments the alignment of the sheath with the tissue is important primarily to align the cutter with the tissue so that the shape, location, and size of the aperture can be controlled. However, it is most critical that the blade be aligned properly with the tissue, and in come embodiments the face of the blade may not be orthogonal to the sheath or catheter. In fact, in one embodiment the blade is at a 45 degree angle to the longitudinal axis of the catheter. As such, the catheter (or sheath, guidewire) need not be bent at an orthogonal angle to the tissue, but indeed may remain straighter as the blade itself will provide the proper orientation. Of course, the adjustment of the angle to fit the needs of the cut and the device is expected. In other embodiments the tissue is brought into alignment with the cutter, that is the tissue is held by the tissue retention device and turned to face the cutter.

Once the introducer is located next to or near the target tissue 30 the catheter 10 is advanced past the end of or to the end of the introducer 50 and placed in contact with the tissue 30. Preferably using the unique markers 26, 28 the physician can tell on the visualization system when the catheter has exited the introducer or has contacted the tissue. Likewise, the catheter 10 may include sensors (not shown) that identify when it contacts the tissue, such as a force sensor, fiber optics, a camera, and electrode using impedance sensing, mapping systems, ultrasound, or the like. In a first embodiment, the circular cutter 16 is advanced into the tissue 30 to cut a circular aperture in the tissue. In an alternative embodiment the introducer 50 is not utilized and the catheter itself is steered into position near tissue 30, and is advanced to cut the aperture.

In one embodiment, once the introducer is in place a transeptal crossing system is used to cross the fossa. Then once across the crossing system is typically replaced with a guidewire. The guidewire 40 remains in position across the interatrial septum and guides either the introducer 50, the catheter 10, or both into position. Guidewire 40 may comprise a retention means on its distal end. Alternatively, guidewire 40 or the retention means may be a part of catheter 10. For example guidewire 40 may include a balloon 42, a pigtail (not shown), an expandable nitinol basket (not shown), a disk or expandable disk (not shown) or similar means. In operation the guidewire 40 is passed through the interatrial septum. Once across, balloon 42 is inflated (or the pigtail secured or the nitinol basket or the disk expanded) and the guidewire is pulled proximally towards catheter 10 to secure the tissue against catheter 10 and cutter 16. Likewise a pigtail, hook or helical means can be utilized to secure the tissue against catheter 10. Multiple means may be used, including a balloon 42 to push the tissue and a hook to retain any loose or dislodged tissue.

While the balloon, pigtail, or similar means are shown as being on the distal portion of guidewire 40, they may also be on the distal portion of the catheter 10. For example a thinner, distal portion of catheter 10 may be passed through the interatrial septum 30 to allow the balloon 42, or pigtail to secure the tissue 30. The distal portion of the catheter with the articulator, e.g., balloon 42, pigtail, basket, or disk may ride over a guidewire, or may forego a guidewire entirely. In such an embodiment the catheter 10 may not need lumen 13, or may find alternative usage for it, such as irrigation or suction. Of course a lumen 13 for a guidewire 40 may still use the lumen 13 for irrigation and suction as well.

In an embodiment the articulator (balloon 42, pigtail, basket, or disk) will pull the tissue of the interatrial septum into a lumen 32 of catheter 10 such that the tissue is tented, preferably into the catheter's lumen (as shown). Once the tissue is tented the cutter 16 will cut the tissue 30 resulting in a larger aperture due to the tenting. Tenting the tissue has several advantages. First in many cases it will allow for a larger aperture size combined with a smaller catheter size. Likewise it may give the physician a degree of control over the size the aperture. For example if the physician desires a smaller aperture for a particular patient, he may wish to reduce the amount of tenting or keep it to a minimum. If the physician desires a larger aperture for the patient he will increase the amount of tenting pulling the tissue further into the lumen 32 creating a larger aperture when the cutting means 16 is applied.

While the above description describes guidewire 40 as a separate device, it is also contemplated that catheter 10 may comprise a lumen in its center containing the guidewire 40. In this embodiment guidewire 40 is first advanced across the interatrial septum, either by itself, piercing the septum, or over a pre-existing guidewire placed earlier in the procedure. The guidewire 40 may be actuated by the first or second actuator 20, 22 on handle 11, manually by the physician, or by an actuator on a separate handle.

In one embodiment the handle 11 comprises a sliding actuator that advances the guidewire distally or withdraws it approximately in a one-to-one ratio between the movement of the guidewire and the movement of the actuator on the handle. In this situation once the catheter is advanced to the interatrial septum and the guidewire 40 is advanced across the septum, the balloon is inflated, and pulled back against the tissue 30 by actuation or by withdrawing the entire device. At this point the actuator 20 is moved proximally to pull the tissue into the cutter 16 creating the aperture in the tissue 30.

Because the guidewire may include a pigtail or hook, the tissue cut from the interatrial septum to complete the aperture is positively retained the inside the catheter 10 and is withdrawn from the body with the catheter 10. While the guidewire has been described as having either a balloon or pigtail, other articulation and tissue retention devices are contemplated. In particular a disc device can be utilized (not shown). The disc device may include one disc that is navigated to the distal side of tissue 30, or may include a disc on each side of the tissue 30. The two discs may be actuated to secure the tissue between them. The disc may be expandable having a small diameter when crossing the septum and a larger diameter when securing the tissue. Cutter 16 may ride over the disc(s), pulling them into lumen 32 to cut the tissue which then remains retained between the two discs and is removed from the body.

After the tissue 30 is cut the balloon 42 is deflated and it is retracted back into the catheter 10. Likewise, if the device utilizes a pigtail or discs they are withdrawn into or to the catheter after the tissue is cut. Likewise catheter 10 may utilize a suction device (not shown) to remove any tissue that is cut or loosened from the atrial septum. In one embodiment the tissue is then removed from the body while the catheter 10 is left in place. Accordingly, suction may be employed to remove the tissue through the lumen. Alternatively, the articulator may be on a separate catheter (not shown) contained inside catheter 10. This separate catheter may be withdrawn with the tissue. It may then be cleaned and replaced, or replaced by a second, similar device, so that a second cut may be made safely.

The cutter 16 is preferably a shaped blade 16 located around the distal catheter lumen 32. In a first embodiment, shaped blade 16 is circular in shape and has on its distal end a razor like member formed of steel or another suitable metal or material. In a related embodiment the cutter 16 includes saw teeth for cutting through the tissue 30. In another embodiment cutter 16 comprises rotary blade 16 and is capable of spinning or rotating to cut or form an incision. The rotary blade 16 may comprise a blade capable of spinning in relation to the catheter, or may comprise a distal cam action on the catheter shaft. Suction or another tissue holding mechanism is preferably employed with a rotating blade to hold the tissue in place while the cut is completed.

In other embodiments the cutter may be triangular in shape, square, or another polygonal shape such as an octagon, such that when forced through the tissue 30 the shaped blade 16 creates an aperture by cutting out an area of the tissue creating a hole, preferably a shaped hole. Notably, the shape of the hole may not match the blade precisely, e.g., an octagonal blade may create a circular hole, and tenting as described herein may substantially alter the shape of the hole, e.g., a circular blade may create an oblong aperture due to uneven tenting due to many factors, including inconsistent tissue elasticity or thickness. Likewise, the blade can provide an elongated slit with a small width and a radius on each end—to create a structure that has a small sectional area under low pressure, but increases in area with a high pressure differential.

Figure 1A:
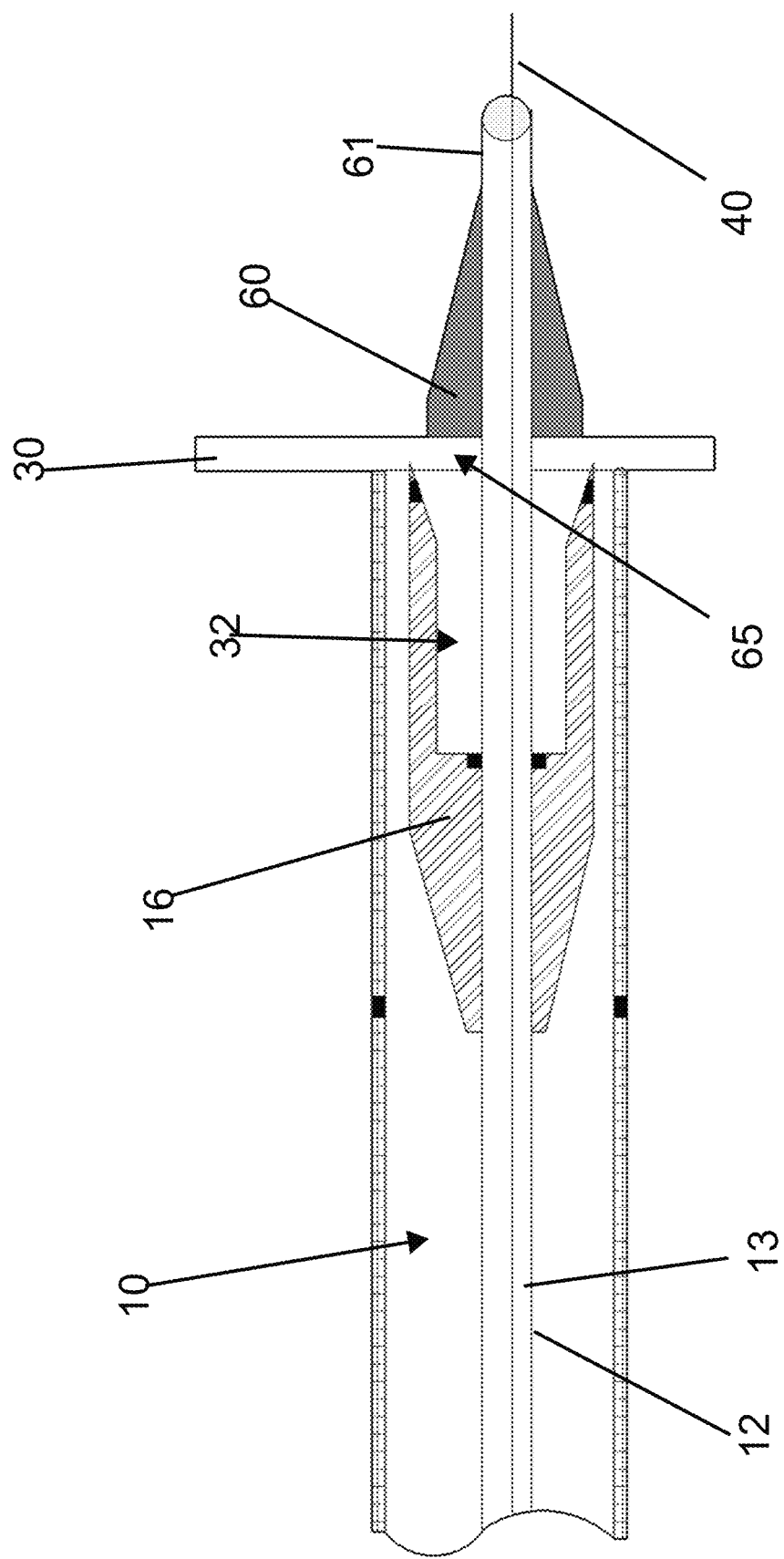
FIG. 1A is a partial perspective view of a catheter and a retention mechanism inserted into a target tissue.

As shown in FIG. 1A, in another embodiment catheter 10 includes shaft 12, lumen 13, distal lumen 32 cutting blade 16 as well as a tissue articulator 60, shown in a conical shape. Tissue articulator 60 is actuatable along the lumen 13. The tissue articulator 60 may be actuated for one of a couple purposes, including grabbing tissue, penetrating tissue, tenting tissue, with the cutting blade 16 cutting tissue, or retaining tissue. The tissue articulator 60 may be actuated multiple times for the same or different purposes. It may, for example, be actuated once to penetrate the septum 30. It (or the blade 16) may then be actuated to retain the tissue, e.g., against the blade, and then actuated a third time for cutting.

The actuation may take one of several forms. An actuator on the handle may be used. Likewise, the tissue articulator 60 may ride on a guidewire or a catheter that is slidable relative to catheter 10 or cutting means 16. In such a case the actuator is the catheter shaft and it may be slid back and forth as needed.

The tapered cone 60 in one embodiment is the tissue articulator 60, and is attached to a stainless steel tube 61 that comprises the outer diameter of lumen 13. The tapered cone 60 and the cutting blade 16 are both of a sufficient diameter to cut an aperture of the desired size. For example at its widest point the tapered cone 60 may be 6 mm wide. In operation the tapered cone 60 rides over a guidewire 40 that runs through a lumen 13 to the left atrium. The tapered cone 60 is forced through the atrial septum 30. As the tissue in the septum is elastic it will stretch over the tapered cone as it passes through and then will partially recover to fit in the space 65 between the tapered cone 60 and the cutting blade 16. The tissue may also have some tearing present. While the space 65 may be a longer space, which may allow for more tissue to be gathered into lumen 32, in one embodiment space 65 is a short narrow segment that only leaves enough of a longitudinal gap for the tissue 30 to fit between the distal tip of the cutting blade 16 and the cone 60, e.g., 2 mm. The tapered cone 60 is then actuated and pulled proximally into the lumen 32. Because the tapered cone 60 fits precisely within the lumen 32 it pulls into the lumen even if the catheter is at an angle or is bent. This action pulls the tissue 30 into the cutting blade 16, cutting an aperture in the interatrial septum. The tissue 30 is captured within the lumen 32 and held in place by the withdrawn tapered cone 60 and removed from the body.

The tapered cone 60 may have a drug coating for one or more purposes. For example, it may have a hydrophilic coating to reduce tearing as it passes through the interatrial septum 30. A slippery tapered cone 60 will reduce tenting due to friction as it passes through the tissue. Likewise the tapered cone 60 may have a drug coating that will slow fibroblast proliferation and migration as well as the secretion of extracellular matrices, e.g. Pacelitaxel. Likewise, the cutting blade 16 may include one or more of these coatings.

Figure 2:
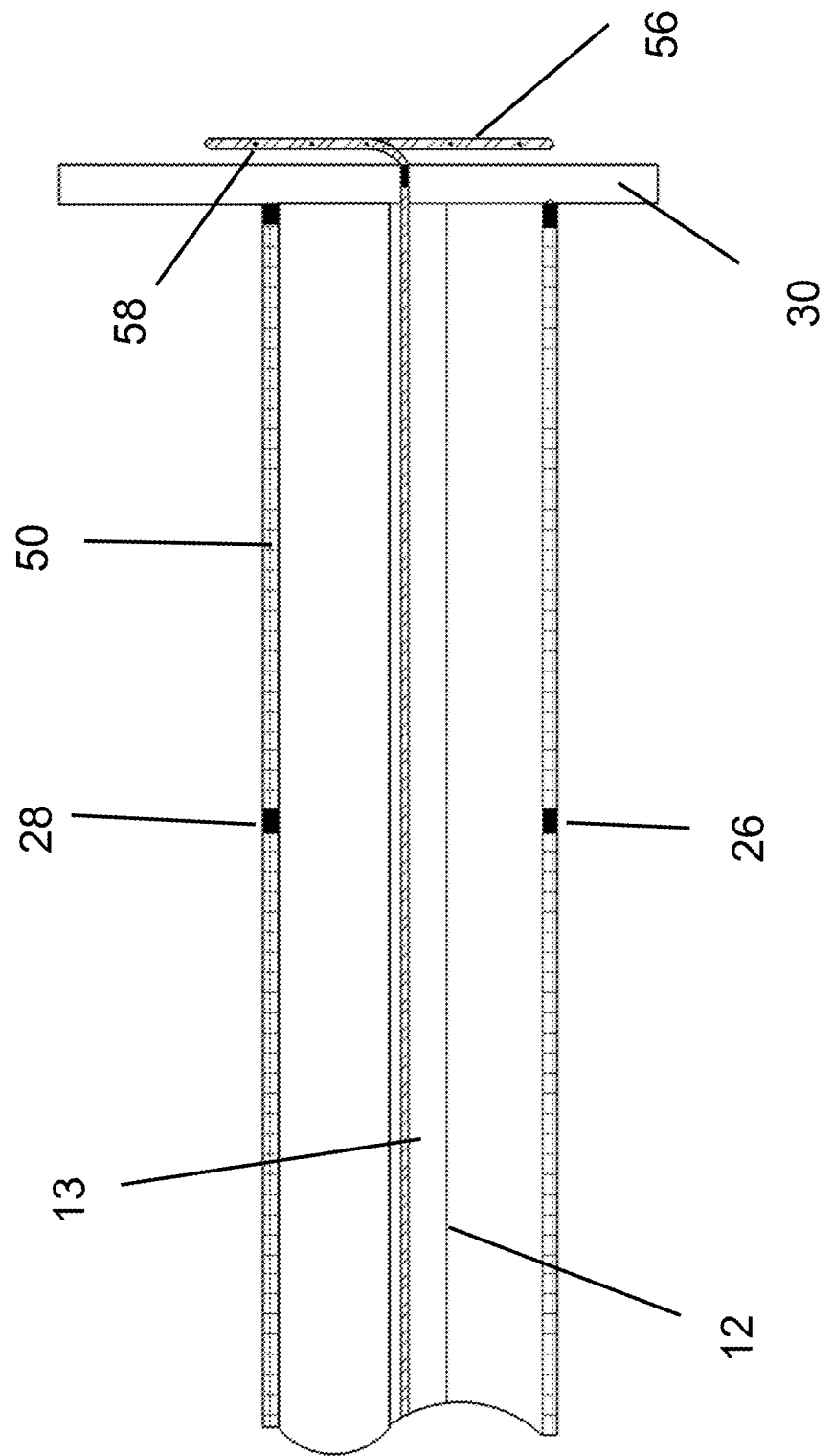
FIG. 2 is a partial perspective view of a catheter constructed according to the present disclosure.

As shown in FIG. 2, in another embodiment cutter 56 is formed of a shape memory metal so that when it is fully retracted and inside catheter 10 it takes a more linear shape. However, when cutter 56 exits the catheter it assumes one of a number shape of shapes. For instance in a first embodiment cutter 56 exits the catheter 10 and assumes a circular shape that is orthogonal to catheter 10, as shown in FIG. 2. Thus when pressed against the tissue from the distal side (from the left atrium) the cutter 56 forms a circular loop against the tissue and cuts a circular hole. Cutter 56 may retain a straight shape while on the proximal side of the interatrial septum, and may be forced through the septum where it assumes a circular shape on the distal side of the septum. It is pulled back against the tissue cutting the aperture. As can be appreciated, once the hole is cut, the blade 56 may be pulled back into the catheter 10 and removed from the heart. The cutter 56 may include tissue retention devices as disclosed herein to retain the tissue as the cutting is performed. Likewise, suction may be employed to retain the tissue. Alternatively, the retention devices may be on the distal end of the catheter 10, or on the articulator. The catheter 10 may have irrigation or suction ports 58 on the cutter 56. Cutter 56 may cut from either side of the tissue 30, the proximal or distal side. As may be appreciated, cutter 56 may be a shaped blade in a number of different shapes, including a star, circle, square, triangle, or another polygon.

Figure 3:
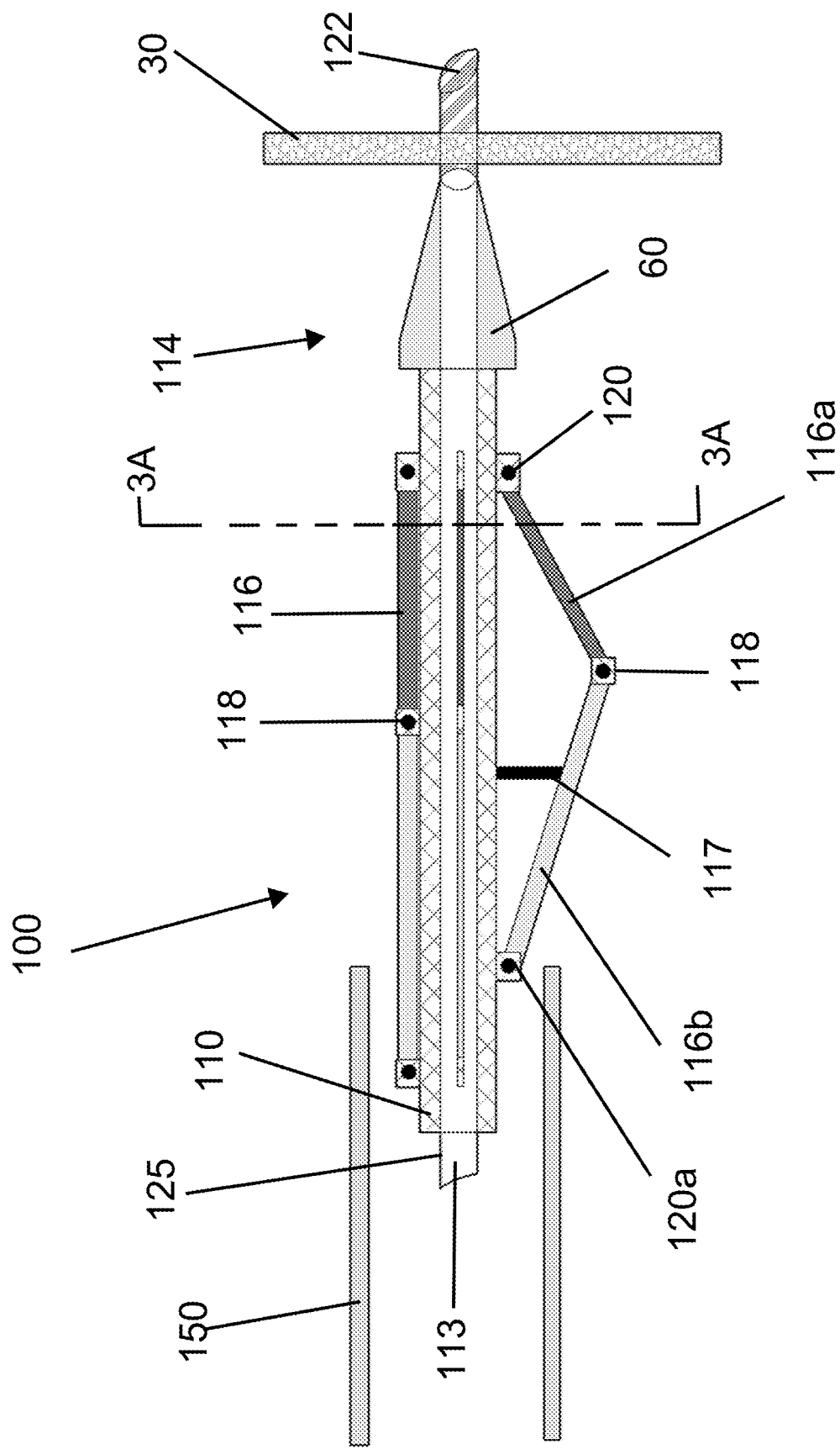
FIG. 3 is a partial perspective view of a catheter constructed according to the present disclosure.
Figure 3A:
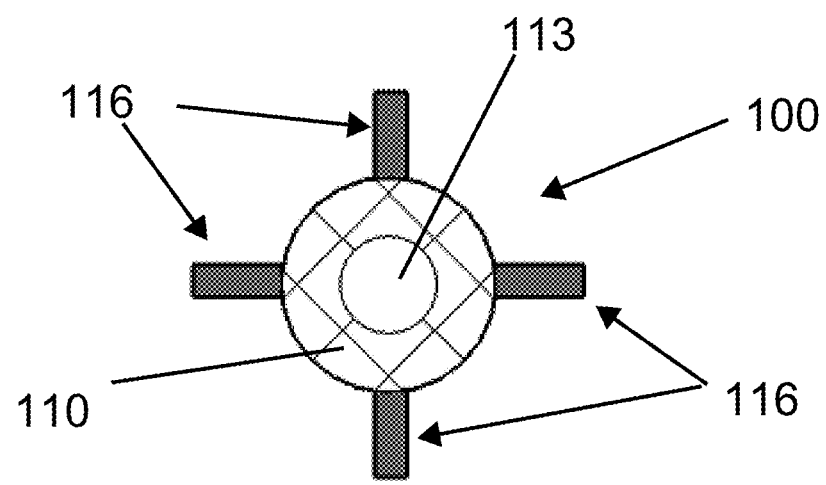
FIG. 3a is a cross sectional view of the catheter of FIG. 3 taken along line 3A on FIG. 3.

While in embodiments catheter 10 creates a circular aperture in the interatrial septum, in an alternative embodiment, as shown in FIG. 3, catheter 100 is designed to create a patterned cut in tissue 30 that will provide a durable aperture between the two atria. In particular catheter 100 comprises shaft 110 with a distal end 114. The distal end 114 comprises blades 116. As shown in FIG. 3*a*, a cross-section of the distal end of the catheter 100 of FIG. 3, the distal end 114 of catheter shaft 110 may comprise four blades 116 arranged approximately 90° apart around the circumference of the catheter 100.

In use, the catheter 100 is inserted into the right atrium while inside sheath 150. Sheath 150 protects the surrounding vein and other tissue from blades 116 until the catheter 100 is in place to create the aperture. There are two broad mechanisms of action. First when catheter 100 is placed against the interatrial septum tissue 30 the introducer 150 may be actuated and withdrawn allowing blades 116 to open. At this point the catheter 100 is actuated or pushed through the interatrial septum 30 and the blades 116 create a patterned cut in the tissue. In the case of four blades the pattern cut appears as an X. The four flaps of tissue that are created will provide a durable aperture.

The physician may also push the introducer 150 up against the interatrial septum 30. The catheter 100 with the blades 116 still retracted may be pushed through the interatrial septum 30. As it passes through the septum, the catheter 100 exits the introducer 150 allowing the blades 116 to deploy. The catheter 100 is then pulled back in a proximal direction towards the right atrium cutting the tissue in the desired pattern. As the catheter 100 is pulled back in the proximal direction and after it has created the desired cut it will reenter the sheath 150 retracting the blades for removal from the body.

It is contemplated that a combination of the two embodiments of FIGS. 1 and 3 is also possible such that a first cutting mechanism 16 will create a hole in the interatrial septum tissue 30 and a second cutting mechanism 116 will create additional cuts and a flap system. The hole and the flaps together to create a durable aperture between the two atria. Likewise, a tapered cone 60 (FIG. 3) may create a small circular hole as it passes through the septum and be followed by the blades cutting a patterned flap system. Such a device may be useful to create an elongated hole such as a slit with radiused ends. This aperture structure may provide a low degree of shunting while the atria are at a low pressure differential and increased shunting when the atria are at a higher pressure differential. The utility of such a design may have particular value with HFrEF patients. The radiusing prevents the aperture from healing over, while the nature of the slit allows for different blood flow under differing pressures.

With reference to FIG. 3, the blades 116 may be extended by any combination of a biasing arm 117, pivots 118, springs (not shown) or biasing materials such as nitinol. In such a case the blades will typically automatically extend when there are no restrictions on it, e.g., as the catheter exits the catheter sheath or after the catheter has pushed through the interatrial septum to the left atrium. In addition it may be advantageous to have the blades automatically fold in based on contact from one direction and automatically extend when that contact is removed. Thus for example the blades may extend based on contact from a distal side e.g. as the catheter pushes into the interatrial septum the contact with the tissue pushes a distal blade portion 116a in the proximal direction, causing the blade mechanism to swing out from the catheter shaft 110. The blades may then automatically withdraw back into the catheter as the catheter is pulled back through the interatrial septum and the catheter blades are contacted from the proximal side by the tissue, or vice versa. Likewise, a combination of biasing or contact may alternately open or close the blades. For example the blades may be biased to open if there are no restrictions, but may be closed using contact with the tissue or introducer as it is withdrawn.

Likewise the blades 116 may be extended via an actuator on a handle. The blades 116 may be attached via pivot pins 120 to the catheter. The blades 116 may comprise multiple blade sections 116a and 116b that pivot around pivots 118, and blade sections 116a, 116b, may slide on a slidable pivot pin 120a or may be secured. The blade sections 116a, 116b may have equivalent lengths, or may be different.

Even if the blades 116 are designed so that no portion of the tissue is intentionally removed from the slits as cut, it can be desirable to employ suction through a lumen 113 in the catheter 100 such that any tissue dislodged during the cutting process is safely removed.

While the blades 116 are illustrated with both ends attached to catheter 100, it is equally possible to have only one blade end attached to the catheter 100 and the other end effectively free or biased into position by arm 117, a spring, or a biased construction.

While four blades are pictured, it is within the scope of this embodiment to use other numbers of blades. In particular three blades to five blades would provide a similar result.

Likewise, a catheter with two blades could be utilized to provide a first cut along one axis and then be rotated 90° to provide a second cut along a second axis. Thus after the two cuts a similar X shaped incision in the transatrial septum would be provided. Similarly a catheter with a single blade could be utilized to provide four cuts 90° apart each and again provide an X shaped incision. As can be seen the desired cut pattern can be created by either providing a catheter with blades pre-existing in the desired pattern, or by providing multiple cuts with one or more blades. While embodiments above have been described with catheter blades equidistant from each other, it is also contemplated that the catheter blades 116 may be arranged in a non-equidistant pattern around the catheter if in the judgment of physician a different pattern is preferred.

Blades 116 can be provided in a number of different shapes. For example catheter 100 could have two diamond shaped blades (not shown) on its distal end. The blades can be permanently diamond shaped or could be collapsible. In the event the blades are parallel to each other and on opposite sides of the catheter the incision in the interatrial septum will resemble an H with a hole at the middle (the hole being caused by the catheter itself). Other shapes are also possible. For example the blades could angle towards each other at the top of the catheter and away from each other at the bottom such that the incision in the interatrial septum will resemble in A with a hole in the middle.

Likewise catheter 100 may include a semicircular shaped blade (not shown). In particular the catheter 100 includes a hollow lumen at its distal end. The cutting blade 116 comprises a semicircular shaped blade that can be rotated. In operation the blade is rotated or extended out of the catheter. The cutting blade 116 is then rotated to cut a circular hole in the interatrial septum. The cutting blade 116 is then rotated back into the lumen in catheter 100.

The catheter 100 may further comprise a stainless steel tube 125 with a BRK or other needle 122 on the end for piercing the interatrial septum 30. The stainless steel tube 125 may be actuated manually or via an actuator on handle to pierce the interatrial septum. Once across it is possible to use a tissue articulator such as cone 60 to increase the diameter of the hole or to work in combination with the cutting blades 116 to hold the tissue in place.

In a similar embodiment, cutting blades 116 comprise a swing or support arm at the distal end of the catheter 100. When the catheter exits a sheath, or when the swing arm is actuated for release, the swing arm will rotate from being parallel to the longitudinal axis of the catheter to an orthogonal position. A razor wire is connected between the extended support arm and the body of the catheter 110 proximally of the distal end where the swing arm is attached. As the catheter is pulled back through the tissue the razor wire will create an incision in the tissue. As can be contemplated, as above multiple cutting blades 116 utilizing a razor wire are possible, and specifically four razor wire support arm combinations would create a similar X pattern incision in tissue 30.

Figure 3B:
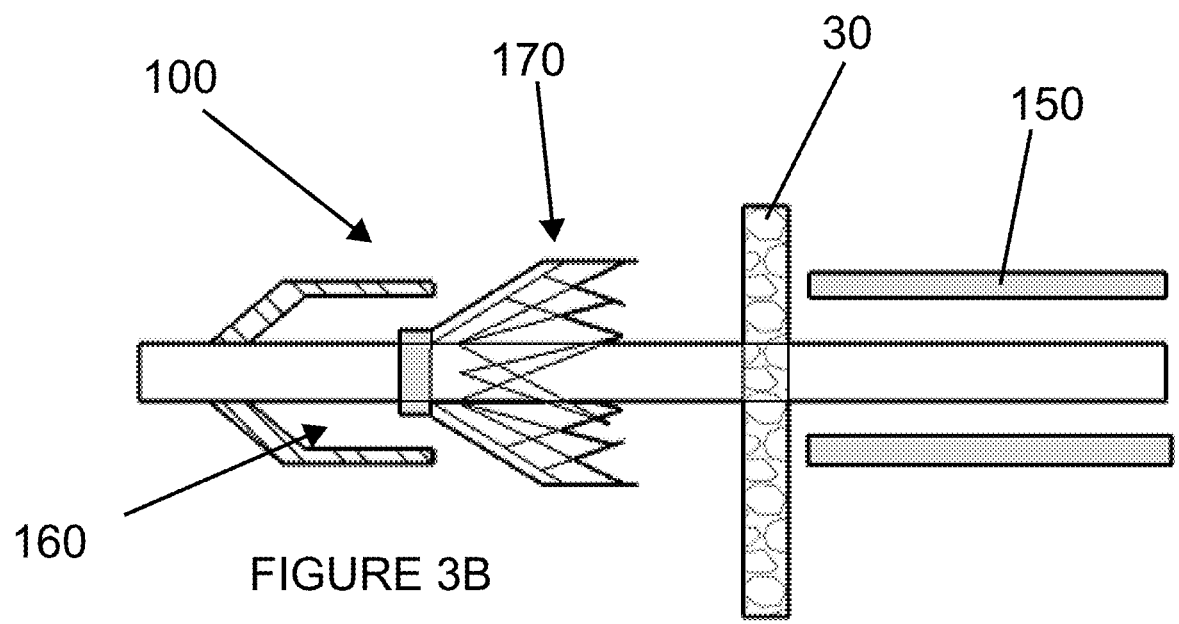
FIG. 3B is a partial perspective view of a catheter constructed according to the present disclosure.

With reference to FIG. 3B, in a further embodiment catheter 100 is pushed through the interatrial septum 30 to the distal side. Catheter 100 includes a lumen 160. Lumen 160 is closed in the distal direction as shown, but is open in the proximal direction. Nestled within lumen 160 is a nitinol basket. Upon actuation the nitinol basket 170 is withdrawn proximally. In a first embodiment, as the nitinol basket 170 exits the lumen 160 it expands substantially forming a much wider basket. The proximal edges of the basket are sharp and accordingly may be drawn into and through the tissue both cutting the tissue to create the aperture, and retaining the tissue for removal. After the aperture is created, the catheter is actuated a second time and the nitinol cutter 170 is pushed back into the lumen 160 causing it to close back up for removal from the body.

In a second embodiment, as the nitinol basket 170 exits the lumen 160 it expands substantially forming a much wider basket to serve as a tissue articulator to retain the tissue or to hold the tissue into a cutting means. As depicted, the proximal edges of the basket may be sharp and accordingly may be drawn into the tissue to hold it and bias it into the cutting means (not shown). The basket 170 may also lack sharp edges and may simply bias or retain the tissue, for example forming a spherical basket 170. After the aperture is created, the catheter is actuated a second time and the nitinol basket 170 is pushed back into the lumen 160 causing it to close back up for removal from the body.

Figure 4:
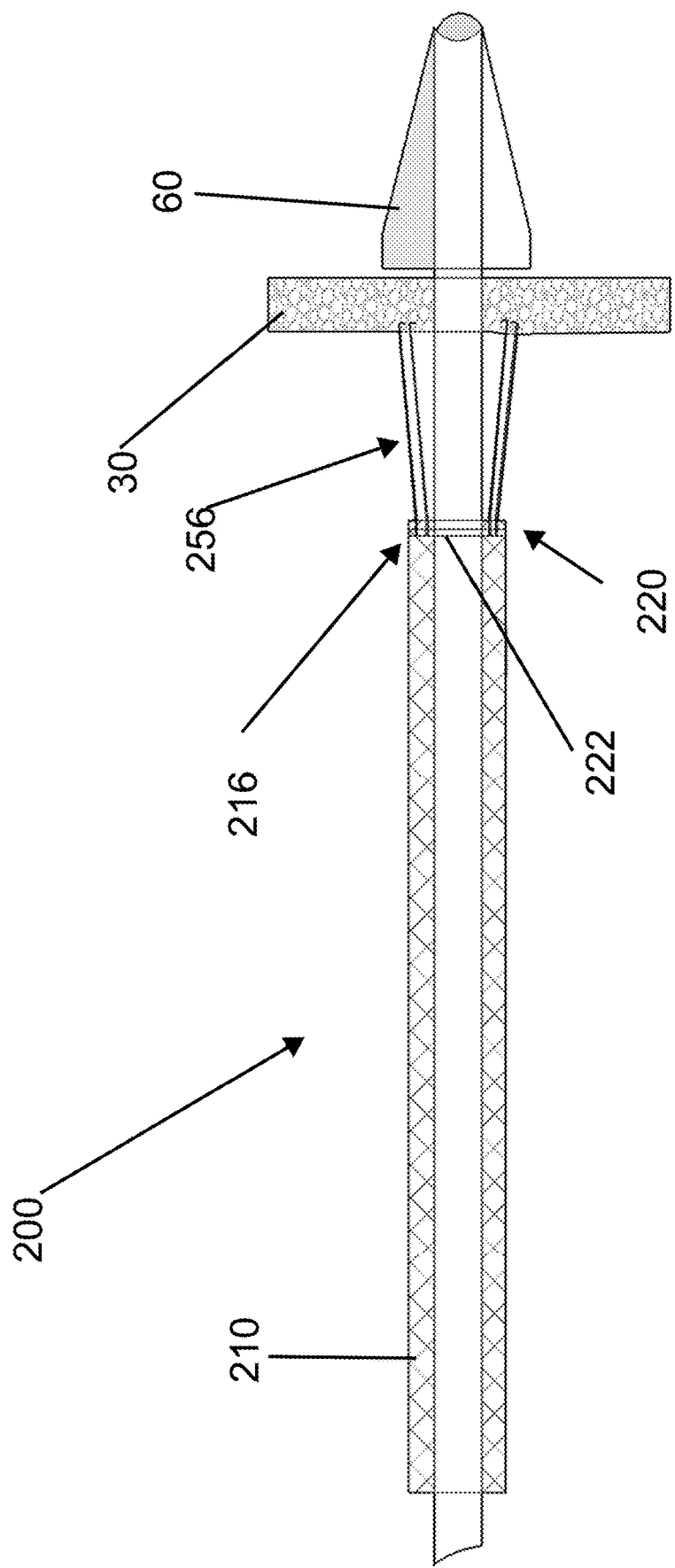
FIG. 4 is a partial perspective view of a catheter constructed according to the present disclosure.

Referring to FIG. 4, in another embodiment of the catheter 200, the catheter 200 comprises an elongated hollow catheter shaft 210 having an interior lumen in which one or more hooks 256 are positioned. The catheter 200 further comprises a distal end 220 with a lumen 222. The hooks 256 are extended out of the catheter shaft 210 and lumen 222 and into the tissue of the interatrial septum 30. Once the hooks 256 firmly grasp the tissue, the hooks 256 are drawn back into lumen 222 to positively retain the tissue 30. While four hooks are shown in FIG. 4, the number of hooks may vary and in particular embodiments with one hook to four hooks are contemplated.

As shown in FIG. 4, when the tissue 30 is grasped by hooks 256 and withdrawn into the lumen 222 the cutting device 216 may be employed to cut the aperture into the tented tissue 30. FIG. 4 depicts the hooks 256 as orienting towards the center of the catheter's central axis. However it is also contemplated that the hooks may be oriented away from the axis of the catheter in another embodiment. Likewise hooks 256 are shown as a long thin rod with a short hook on the end. However, in another embodiment the two hooks more resemble the long grasping arms of a sturdy pliers.

Tissue 30 may be grasped by hooks 256. Alternatively, tissue 30 may be grasped by one or more corkscrew elements (not shown), adhesive, a barbed insert, suction, or the like. Of course, a combination of grasping mechanisms may be effective.

Figure 5:
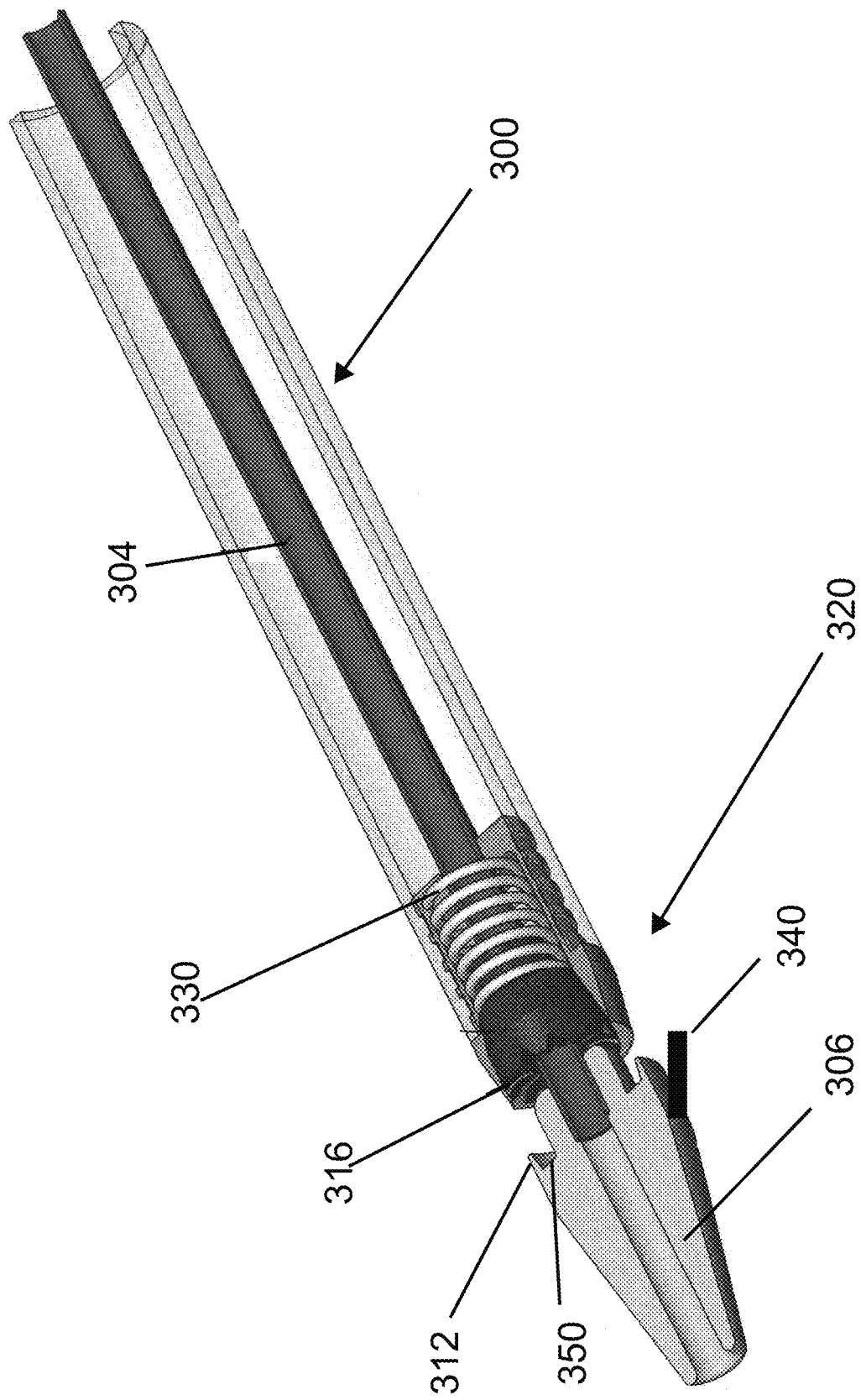
FIG. 5 is a cutaway partial perspective view of a catheter constructed according to the present disclosure.

In a further embodiment, illustrated in FIG. 5, the catheter 300 comprises an elongated hollow catheter 300 having a lumen 304 in which a hooking device 306 is positioned. The catheter further comprises a distal end 320 and a blade 316. The hooking device 306 has barbs 312 that are used to grab or hook into the interatrial septum 30. The hooking device 306 is used pull the septum toward the blade 316 to cut an aperture in the septum. The blade 316 may be actuated or pushed through tissue 30 via spring 330. As with above embodiments, the hooking device 306 may retract inside a cutting blade 316. However, as depicted in FIG. 5, the hooking device may ride over the outside of cutting device 316, e.g., by barbs 312 riding over the outside of cutting blade 316, and cutting blade 316 sitting flush inside the barbs or the cone 306.

Hooking device 306 may include self-expanding arms 340 or portions that may, once the hooking device is passed through the target tissue 30 to the distal side, expand to grab a wider portion of tissue 30. Such an arrangement allows the hooking device to begin as a smaller diameter device that will more easily navigate through the veins to the interatrial septum, but then be expanded to a larger device that will attach to a larger segment of the interatrial septum to create a larger aperture. Thus, the hooking device 306 may allow the operator the ability to make an aperture that is larger than the OD of the catheter device. Self-expanding arms 340 may comprise an additional grabbing or hooking mechanism, or may comprise a blade to provide a larger aperture.

The hooking device 306 may operate in different manners. First, it may merely penetrate into but not through the tissue and via teeth (not shown) pull the tissue into the lumen 304 of the catheter 300. Preferably however a conically shaped hooking device 306 penetrates through the septum entirely, and is withdrawn back to the tissue such that its proximal face 350 grabs the tissue and pulls it into the lumen of the catheter 300. At this point the tissue is brought in contact with the cutting device 316. The cutting device 316 may comprise a shaped cutting device as disclosed above. In addition cutting device 316 may comprise a semicircular blade. The semicircular blade 316 may be rotated such that as it is rotated it will create a circular hole in the tissue. The advantage of a semicircular blade over a fully circular blade is that less force will be required for the cutting action. The disadvantage is that the blade must be rotated, or the entire catheter be rotated, to create the desired cut. In the event the physician does not wish to remove tissue from the interatrial septum a semicircular blade may be utilized to create a flap by not rotating 360°.

While FIG. 5 shows the cutting device 316 on the distal portion of the catheter shaft 300, the cutting device 316 may instead be on the proximal portion of hooking device 306. Likewise there may be two cutting devices 316: one on the distal end of the catheter shaft 300, and one on the proximal portion of the hooking device 306. As they are drawn together they will cut the tissue via a scissoring action.

Figure 6:
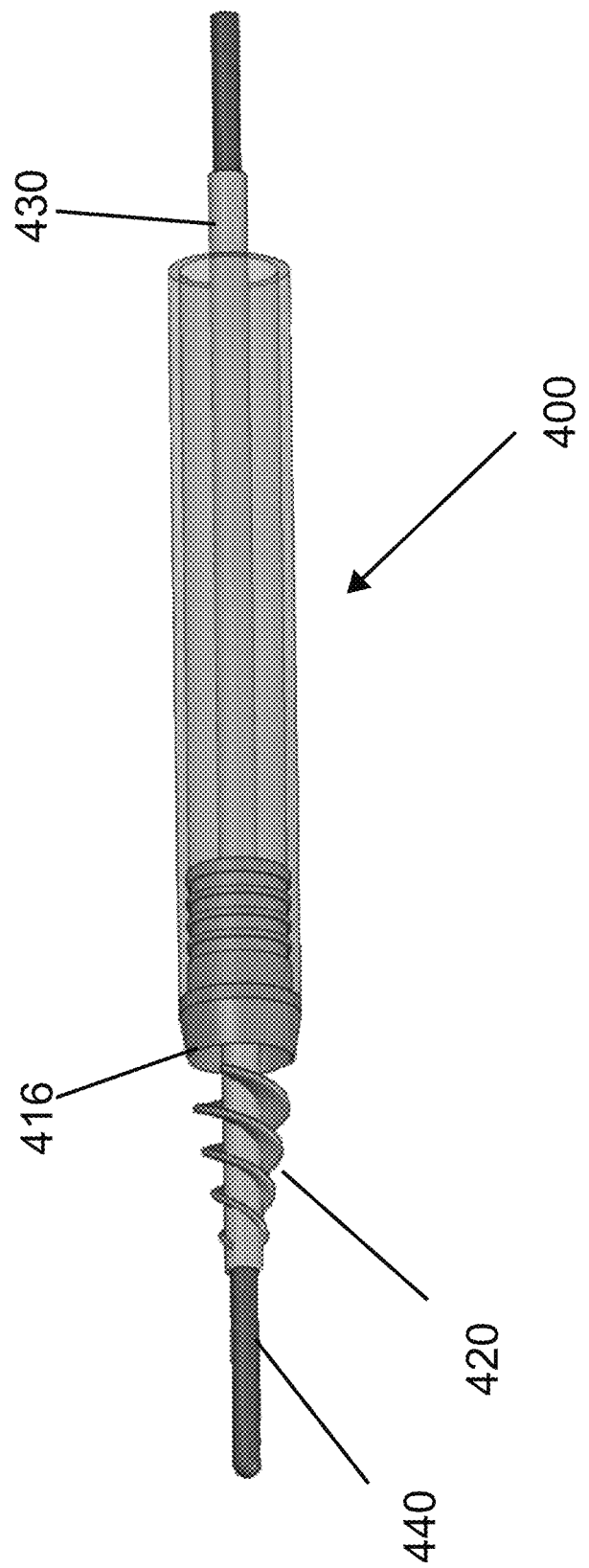
FIG. 6 is a partial perspective view of a catheter constructed according to the present disclosure.

With reference to FIG. 6 the catheter 400 may comprise an auger 420. The auger 420 may include a lumen 430 for riding over a guidewire 440. In use the guidewire 440 crosses the septum into the left atrium. The auger 420 is rotated to likewise cross the septum. Because of the spiral design of the auger it does not create as large of a tear or perforation in the septum 30 because only one radius of the auger is in contact with the septum at any given time. However once the auger is in the left atrium, it may be pulled back to pull the septum 30 into cutter 416.

Figure 7:
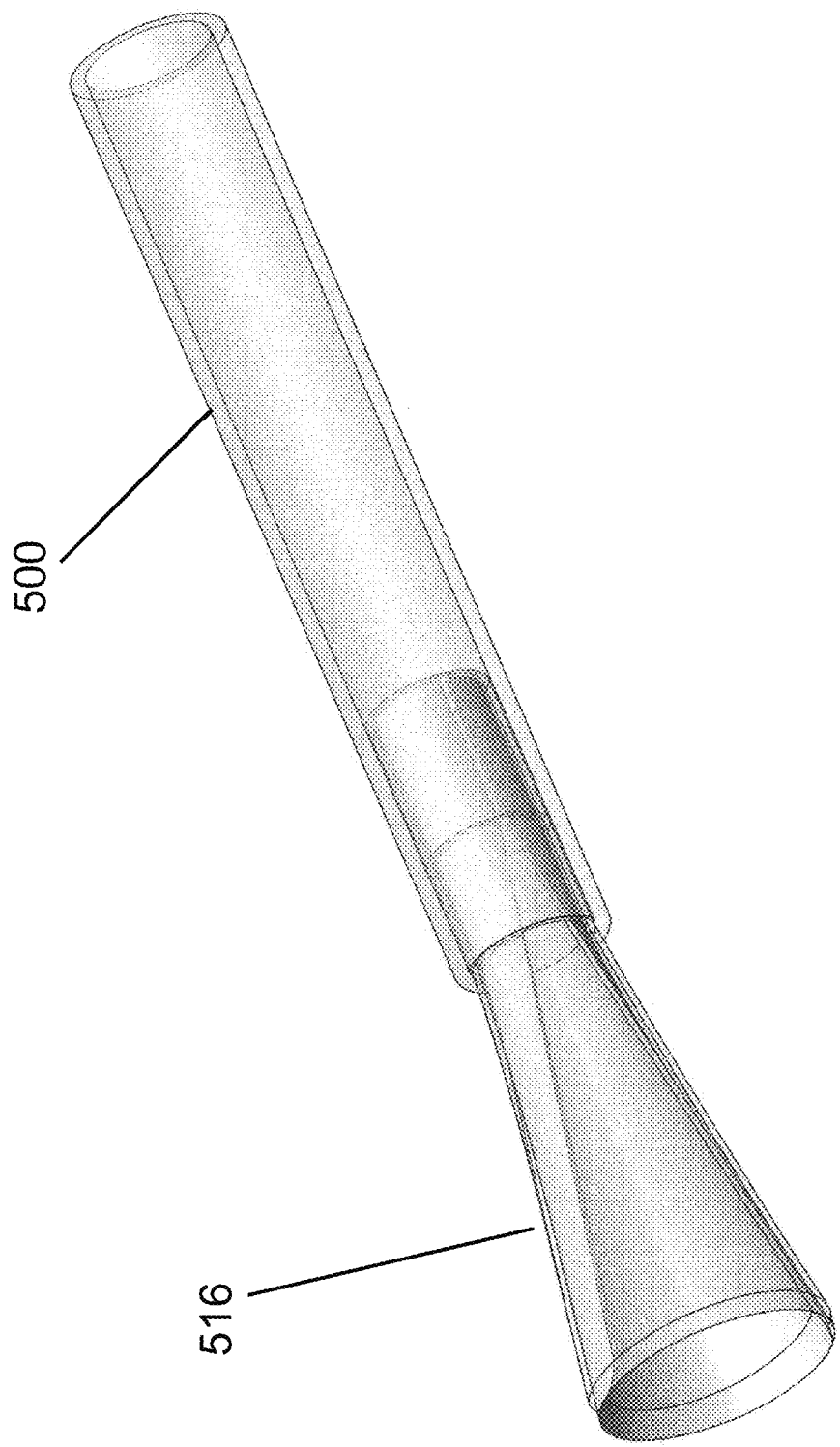
FIG. 7 is a partial perspective view of a catheter constructed according to the present disclosure.

The cutting device may take alternative forms. Similar to the semicircular blade, the blade may take the form of a coiled blade (not shown). The coiled blade may be contained within the lumen of the catheter. Once deployed out of the catheter and uncoiled the blade is used to cut a hole in the septum as above. The coil may take several forms. For instance the coiled blade may take the form of an auger (not shown). Likewise the coiled blade may take the form of a coiled rolled sheet as shown in FIG. 7. Both such forms may give the physician discretion as to how large of an aperture he wishes to create in the interatrial septum. For instance a blade formed into a coiled rolled sheet 516 may, as it exits the catheter further and further, continually take on a larger and larger diameter. Thus for a small aperture the physician may only extend the coiled rolled sheet a short distance out of the catheter 500 and as such the coiled rolled sheet will only create a aperture approximately the diameter of the catheter itself. However if a larger aperture is desired the coiled rolled sheet will be removed further and further out of the catheter as shown in FIG. 7 and allowed to unroll into a larger circular shape. Thus the created aperture will be much larger. In one embodiment suction is employed with the coiled rolled sheet to hold the tissue in place.

While FIG. 7 depicts the coiled rolled sheet 516 as exiting the catheter 500, it is contemplated that the coiled rolled sheet may be coiled around the exterior of catheter 500, and may unfurl as it exits an introducer (not shown).

Because the coiled rolled sheet is capable of creating different sized apertures, it is possible for the physician to provide a progressive enlargement of the aperture during the procedure. For example the physician can create a first aperture at a first size, monitor the ejection fraction for example, or the pressure in the two atria, and determine that a larger aperture is required. The physician would then adapt the size of the cutting mechanism and create a second, larger aperture in the same place as the first aperture was. In the alternative, the physician could simply create a first aperture in a second location that is substantially the same size as the first aperture using the original size cutting means.

Figure 8A:
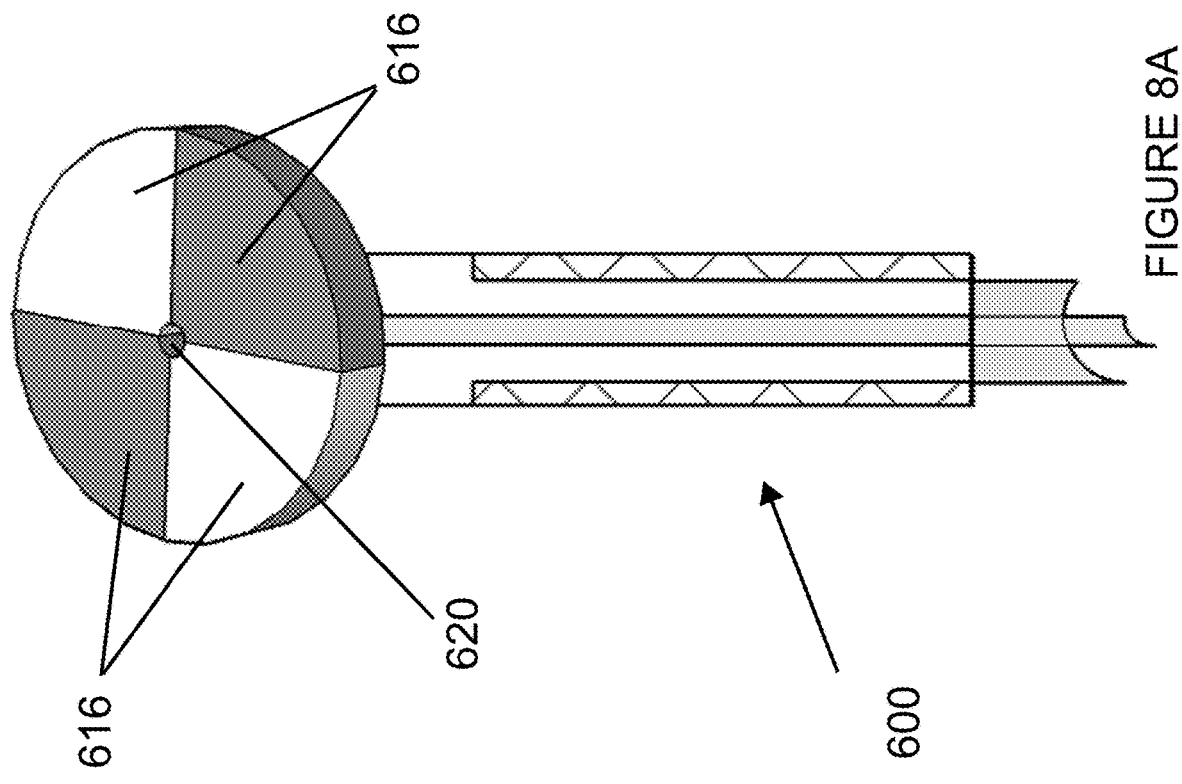
FIG. 8A is a partial perspective view of a catheter constructed according to the present disclosure.
Figure 8:
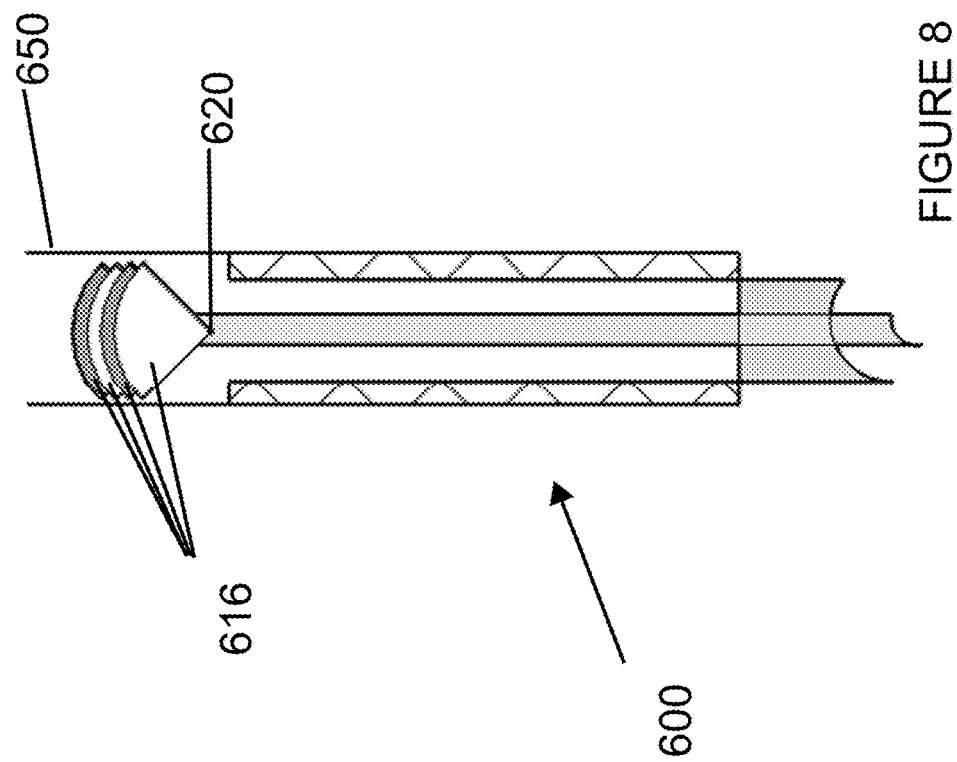
FIG. 8 is a partial perspective view of a catheter constructed according to the present disclosure.

With reference to FIGS. 8 and 8a, the catheter 600 may comprise multiple angled cutting arms 616. Each cutting arm is attached to the catheter shaft 610 by via a hinge 620. While the cutting arms 616 remain within the sheath 650 they are aligned with each other to present a smaller cross-section. However once deployed out of the sheath they rotate on the hinge to form an overlapping cutting surface in a desired shape, e.g., a circular shape as shown in FIG. 8a. While the multiple cutting arms 616 are depicted in a leaf shape that opens into the four quarters of a circle, the cutting arms 616 may take multiple forms. For example while the cutting arms are depicted as being oriented perpendicularly to the longitudinal axis of catheter 600, the cutting arms 616 may be oriented parallel to the longitudinal axis of catheter 600, and as such when open would present a similar cutting edge to the coiled rolled sheet 516 depicted in FIG. 7.

Figure 9A:
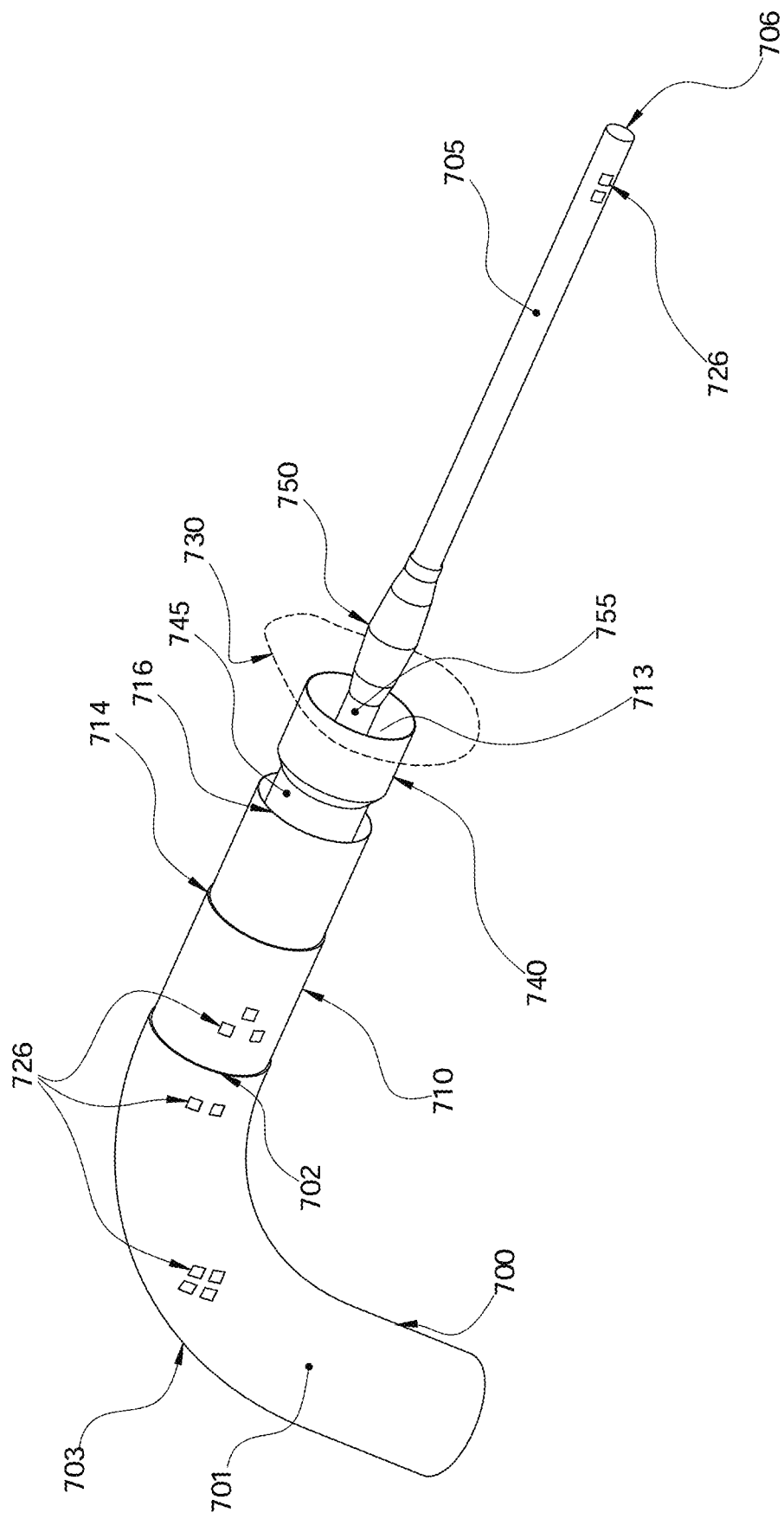
FIG. 9A is a partial perspective view of a catheter constructed according to the present disclosure.
Figure 9B:
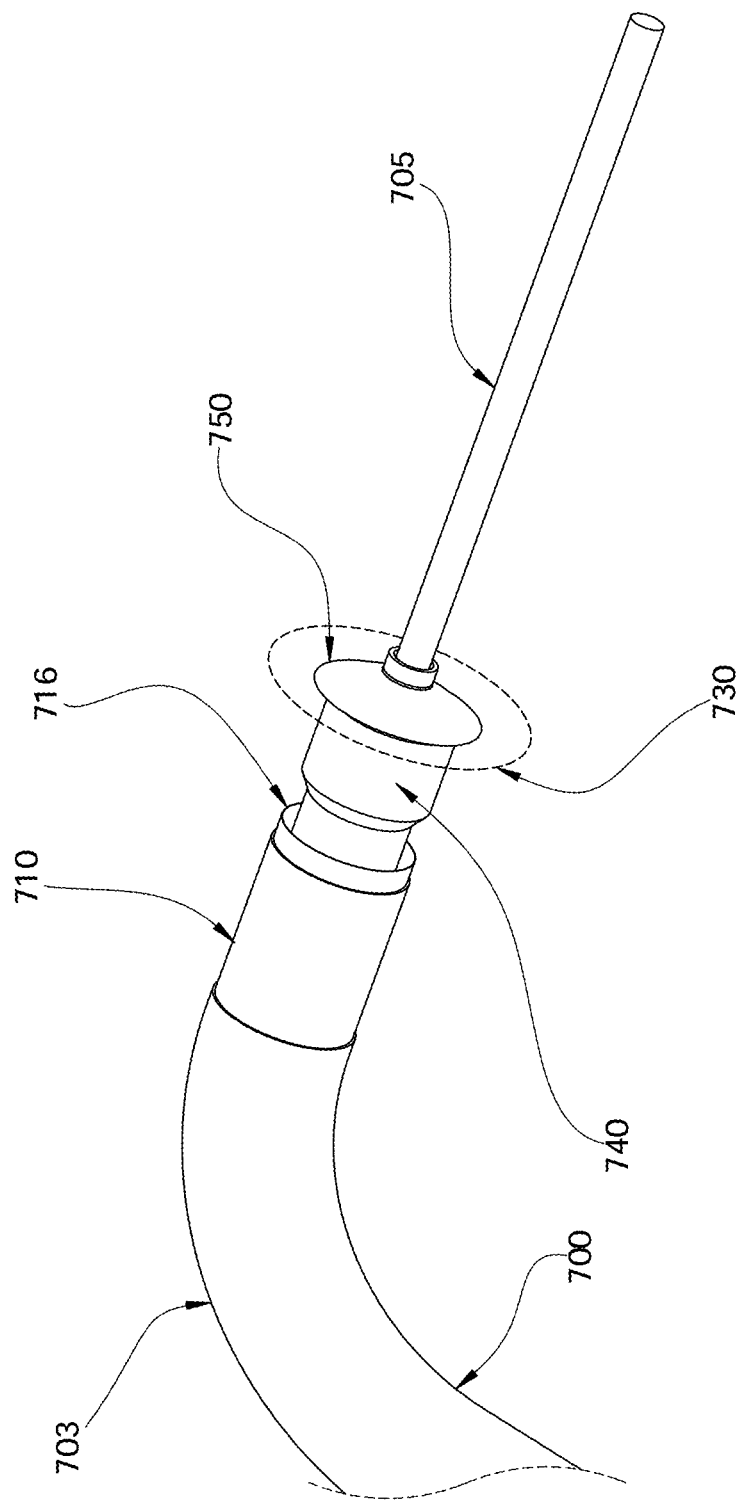
FIG. 9B is a partial perspective view of a catheter constructed according to the present disclosure.
Figure 9C:
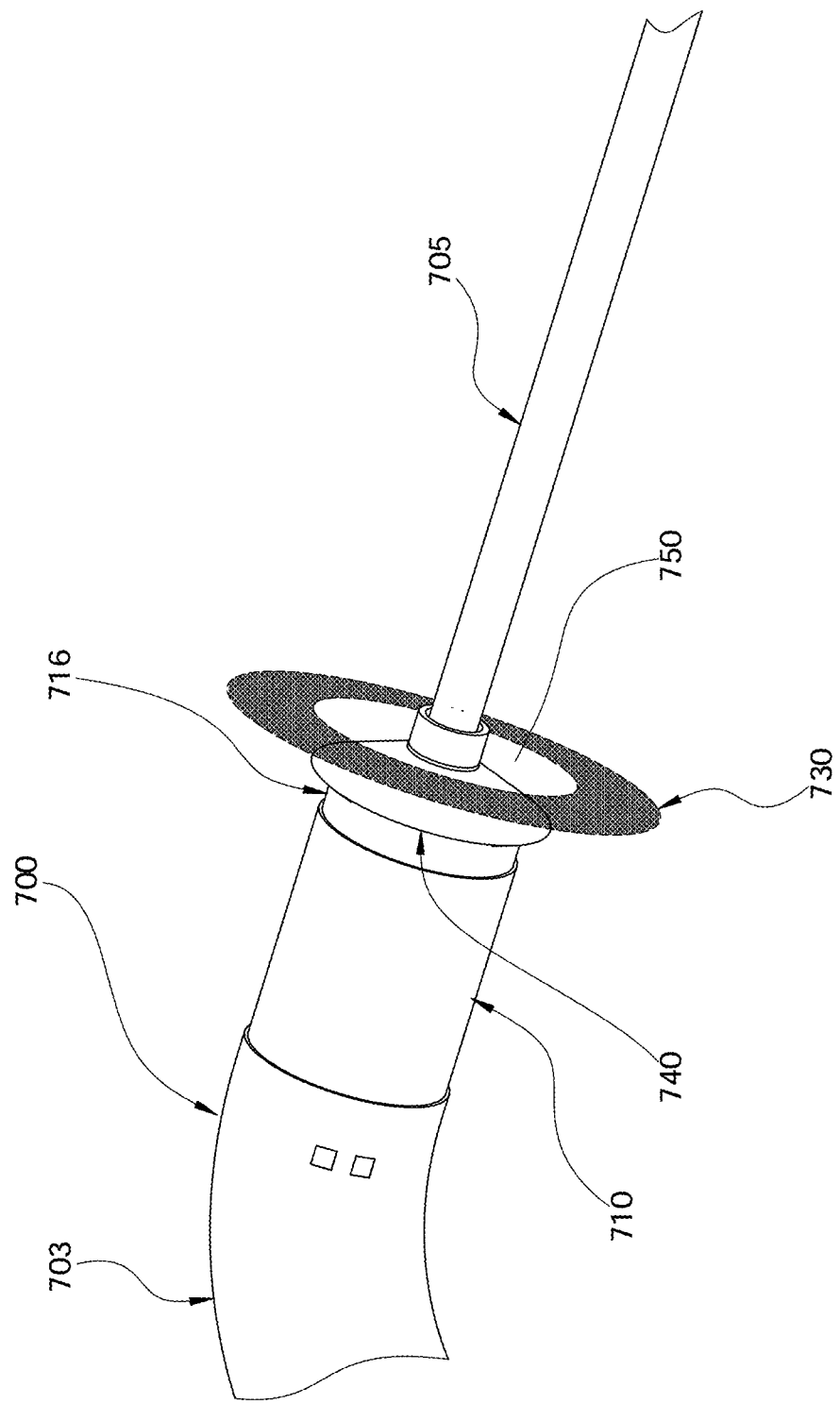
FIG. 9C is a partial perspective view of a catheter constructed according to the present disclosure.

With reference to FIGS. 9A-C, a medical device assembly includes a sheath 700, a catheter 710, and a guidewire 705. While the following description describes the sheath 700, catheter 710 and guidewire 705 as separate devices, it is understood that they equally can be a single device, be integrally connected (but preferably laterally moveable relative to each other), and be controlled by the same or different proximal handles and electrical connections. In particular, the attributes of the sheath 700 and catheter 710 may be advantageously combined. Likewise, the sheath, catheter, or guidewire may be omitted. While at least one of the devices will need to traverse the length of the body from the entry point to the atrium, it is contemplated that the other devices may be shorter. For example, the sheath may traverse from the percutaneous entry point to the right atrium. The catheter may only traverse from one side of the right atrium to the other, for example, and as such be substantially shorter.

Sheath 700 comprises an elongated catheter shaft 701 having a distal end 702 and a proximal end (not shown). The proximal end includes a handle (not shown). The handle may comprise actuators, such as a first actuator, a second actuator, and a third actuator (not shown). It is understood that in the case of multiple handle units on different portions of the assembly, any one of the actuators discussed in the following may be on different handles connected to any of the three components (sheath, catheter, guidewire). The handle(s) may further include fluid port(s) and electrical connection(s) (not shown). Sheath 700 and/or catheter 710 may further include pull wires attached to an actuator for actuating distal elements, moving a lumen or shaft, steering, or the like. Sheath 700 and/or catheter 710 may further include irrigation ports and the like.

Sheath 700 and/or catheter 710 further include markers 726 designed to allow the physician to determine the location and orientation of the sheath 700 and catheter 710 in the patient and the orientation of the different components of the device relatively to each other. For instance, sheath 700 may have radiopaque markers 726 at a bend 703 in a pattern that identifies the bend region. Sheath 700 may then have further radiopaque markers 726 at its distal end 702, again in a distinct pattern that is the same or different from the pattern at bend 703. Likewise catheter 710 may have radiopaque markers 726 at its distal end. Because the catheter 710's radiopaque markers are differently patterned than the sheath 700's radiopaque markers, the physician will be able to quickly and easily identify when the catheter 710 exits the sheath 700. Finally, guidewire 705 may have radiopaque markers 726 so that the guidewire may be quickly identified by fluoroscopy as well. Preferably, the radiopaque markers 726 (or other markers) on the catheter, sheath and guidewire are distinguishable from each other and accordingly the physician is able to determine the spatial relationship of the three components. In one example, spot electrodes may be used and provide a pattern. In another example, an electro-anatomical mapping system is programmed or provided with the specifics of the three components. The specific electrodes, magnetic coils, or other electrodes are identified to the mapping system, e.g., through an EEPROM in the catheter or otherwise, and as the system identifies a specific electrode or coil (e.g., by the current passed through the electrode or coil and to the other components of the mapping system). The mapping system may then clearly and visually identify the location of the three components for the physician.

Advantageously, the sensors may enable the operator to create an electro anatomical map of the right atrium and left atrium. This map can include details such as tissue thickness, especially in the fossa ovalis or the septum. The maps can also be created or supplemented by fluoroscopy, or an imported map such as a CT scan, MRI, live external modalities like TTE, TEE, or information from live on-board catheter sensors, like OCT, ultrasound, CCD camera visuals, for example, to understand the surface morphology, tissue thicknesses, tissue compliance, location of PFO/flap, etc. These live modalities maybe also used independently. For example, the live on-board catheter sensor(s) may be an OCR sensor for imaging the tissue to be cut. This design might also incorporate a live on-board catheter sensor, which is an electrode to keep cutting away from nerve, SA node artery, or for impedance tissue thickness measurements, as examples.

Sheath 700, guidewire 705 and catheter 710 may alternatively or further include ultrasound markers (not shown) or hyper-echogenic markers, again preferably in designed patterns as described above such that the physician may locate the components in the patient on ultrasound imaging. In an alternative embodiment, in place or in addition to radiopaque markers 726, the sheath 700, guidewire 705, and catheter 710 may have electrodes (not shown) that are locatable on an electroanatomical mapping system such as the EnSite™ electroanatomical mapping system. Alternatively, the sheath 700, guidewire 705, and catheter 710 may have magnetic coils locatable on the Carto™ or MediGuide™ mapping systems.

The elongated shaft 701 is preferably hollow, having a lumen 713 that has the ability to pass the catheter 710 and guidewire 705 through it. The catheter 710 is designed to work in conjunction with sheath 700. Sheath 700 may either extend the entire length from the percutaneous incision to the left atrium of the heart, or may only cover a portion of catheter 710.

To achieve a consistent aperture of the shape desired by the physician, it is desirable that the cutting blade enter the tissue 730 perpendicularly to the tissue 730. Unlike that taught in the prior art devices, where the angle of tissue approach is not addressed, the inventors herein have found that the more squarely the cutting blade 716 addresses the tissue 730, the more predictable the size of the aperture and the quality of the aperture. Accordingly, the sheath 700 and the catheter 710 are designed to provide the operator with the ability to provide a right angle approach to the tissue. In another embodiment, the distal plane of the cutter is orthogonal to the plane of the tissue being cut. That is, the entire face of the cutting blade cuts the face of the tissue substantially simultaneously. Because of tissue irregularity it is noted that the blade does not exactly contact the tissue simultaneously. Likewise, the blade may be a sawtoothed or Franseen blade, and may not be capable of a perfectly simultaneous cut, but rather a substantially simultaneous cut where each section of the blade cuts at the same time.

The ideal location for creating the aperture is across the thinnest tissue of the fossa, because it is the easiest to cut. However, if the fossa is crossed without controlling the angle of the crossing the circular blade may cut a hole that is not circular and not the expected size. Also, a shallow angle can lead to the cutter inadvertently cutting unintended tissues, like the atrial wall, causing a safety issue. Finally, after a device, such as a guidewire or catheter crosses the septum, and the angle, side force, or side bias is not controlled by adjusting the angle of the device, the device can inadvertently tear or stretch the tissue. If the tear or stretch is significant enough it will impact the resulting shape of the aperture, and in the worst case the tear will stretch into the location of the cut such that the blade is not cutting any tissue in the location of the tear.

In one such embodiment, sheath 700 extends to the steering/bend 703. In this embodiment the sheath 700 may terminate before the bend 703, and as such the medical assembly is preferably steered/bent by pull wires or biasing in catheter 710. However, in another embodiment, the sheath 700 terminates distally of bend 703. Pull wires or biasing in the sheath 700 enable it to make a sufficient turn to orient catheter 710 toward the interatrial septum 730 and thus the sheath exit and orientation provide an orthogonal guide to the catheter. While in one embodiment the catheter 710 does not have its own biasing or pull wires, in another embodiment the catheter 710 may be separately steerable or biased, and thus provide for the orthogonal approach. Pull wires provide the advantage of minute adjustments to the specific anatomy of the patient, and allow for greater flexibility in the device. One device may be used for nearly all patients and still provide a proper approach angle.

In another embodiment the catheter is controlled b steering the distal tip with a magnetic field. Remote magnetic navigation operates by, for example, using two large magnets placed on either side of the patient, and alterations in the magnetic field produced by the magnets deflects the tips of catheters within the patient to the desired direction. The physician operates the catheter with screen and a joystick. The catheter itself is advanced by the joystick, instead of the physician's hands. Likewise, while a physician may operate the medical devices disclosed herein by hand, the devices may be robotically driven. As with magnetic navigation, the physician operates the catheter with a screen and a joystick. In another embodiment, providing a biasing agent such as a nitinol wire to provide a preformed bend provides the advantage of having a less expensive manufacturing process and a simpler device. However, multiple bend sizes may need to be manufactured.

In another embodiment, the sheath 700 may have a first preformed bend, and the catheter 710 may have a second preformed bend. The first and second preformed bends work together to allow the operator to direct the cutting blade 716 to the septum at a right angle. Likewise, the catheter 710 may have multiple preformed bends. For example, a catheter 710 may have a first and second catheter preformed bend, such that for a smaller atrium only the first bend exits the sheath 700, and with the sheath's orientation, the first bend directs the distal end of the catheter to where the fossa ovalis typically sits for a small heart with smaller chambers. For a larger heart, however, as the catheter 710 must exit farther out of the sheath 700 the second catheter bend also exits, and realigns the distal end of the catheter toward where the fossa ovalis typically sits for a larger heart. Likewise, the assembly may include a removable stiffener, that can be deployed to adjust the distal tip's location to provide a right angle approach to tissue 730.

The sheath 700 and the catheter 710 may include braiding to provide stiffening. Unlike prior art devices which create a hole by energy sources or by implanting a device, the present device may find that significant pressure is necessary to create the aperture. Because the pressure must be transmitted from the length of the sheath or catheter, that pressure will initially push the cutting edge and the entire catheter along rather than through the septum. For example, in a femoral vein entry procedure, the catheter is initially pushed upwards rather than towards the left atrium. Accordingly, unlike the prior art the applicants have discovered that providing stability and steerability in either the sheath or the catheter may greatly reduce this upward pressure and redirect the force towards the interatrial septum 730 to provide a proper cut.

Toward this end, sheath 700 is used to create bend 703 and direct the catheter 710 to the septum 730. Sheath 700 terminates just distally of the bend 703. At this point, in one embodiment the sheath 700 is held in place as catheter 710 is advanced out of the sheath 700 to the septum 730. Because the sheath 700 is sufficiently stiff, it resists the upward pressure and directs the catheter force toward the interatrial septum 730. Together or in place of the sheath, the device contemplates providing anchoring means or stabilizing means (not shown) to prevent the catheter and the cutting blade from shifting and thus allowing a clean cut in the desired location. Sheath 700 and catheter 710 may further include irrigation ports (not shown).

The distal end 714 of catheter 710 comprises a cutting means 716. In a first embodiment the cutting means 716 is a razor like member formed of steel or another suitable metal or material adapted to cut a thin tissue. Toward this end the cutting means may be very thin so that it cleanly and easily pierces the thin tissue. In those embodiments where cutting means 716 has a sharp edge at the end of the catheter 710, it is preferred that the sheath 700, catheter 710, proximal capture component 740, or distal capture component 750 cover and protect the vein and other tissue from the cutting means 716 until the catheter 710 is delivered in place and actuated by the physician to cut the target tissue. In other embodiments a cone (not pictured) or other distal element may cover or sit flush with the cutting blade 716 so that the blade is protected until actuation. The cutting means may be actuated by the advancement of a cutting means shaft (not shown) that sits within a lumen of catheter 710. It may also be advanced by action of a pull wire, or via a twisting action driving a screw attached to the blade forward.

The cutter 716 in one embodiment is a shaped blade 716 located around the distal catheter lumen 713. In a first embodiment, shown in FIG. 9A, shaped blade 716 is circular in shape and has on its distal end a razor like member formed of steel or another suitable metal or material. In a related embodiment the cutter 716 includes saw teeth for cutting through the tissue 730. In another embodiment cutter 716 comprises rotary blade 716 and is capable of spinning or rotating to cut or form an incision. For example, if the blade is driven forward via a rotary action, that rotary action may be accomplished by the screw mechanism above. The rotary blade 716 may comprise a blade capable of spinning in relation to the catheter shaft, or may comprise a distal cam action on the catheter shaft. Suction or another tissue holding mechanism is preferably employed with a rotating blade to hold the tissue in place while the cut is completed.

In other embodiments the cutter may be triangular in shape, square, or another polygonal shape such as an octagon, such that when forced through the tissue 730 the shaped blade 716 creates an aperture by cutting out an area of the tissue creating a hole, preferably a shaped hole. Notably, the shape of the hole may not match the blade precisely, e.g., an octagonal blade may create a circular hole, and tenting as described herein may substantially alter the shape of the hole, e.g., a circular blade may create an oblong aperture due to uneven tenting due to many factors, including inconsistent tissue elasticity or thickness.

Figure 10B:
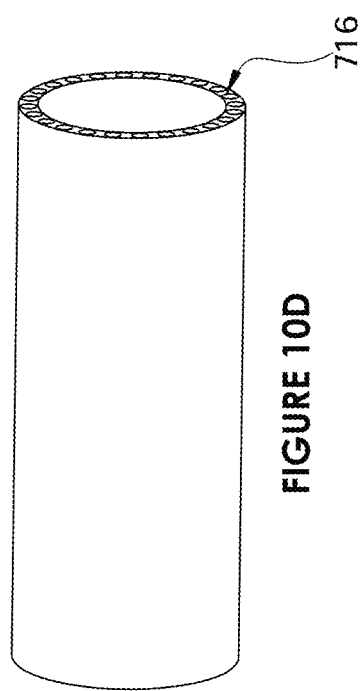
FIG. 10B is a partial perspective view of a cutter constructed according to the present disclosure.
Figure 10A:
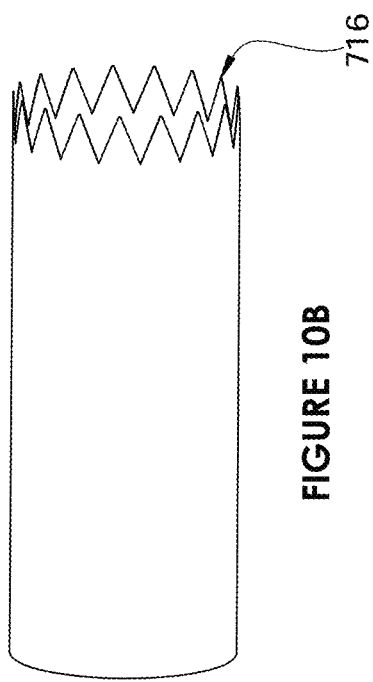
FIG. 10A is a partial perspective view of a cutter constructed according to the present disclosure.

As shown in FIG. 10A, cutting blade 716 may be an angled hypodermic blade. The cutting blade may have a lancet point. As only a portion cuts at any one moment, the pressure required to create the aperture is greatly reduced. As shown in FIG. 10B, cutting blade 716 may be a saw blade (pictured) or may also be a Franseen blade. As shown in FIGS. 10A and 10B, such blades may have a hollow lumen. When employed to cut the aperture, the lumen may be placed under a vacuum to remove any and all debris removed from the tissue 730. The cutting means 716 may be a serrated blade which will allow for a lower cutting force. Likewise the cutting means 716 may comprise a vibrating or impulse blade to likewise allow for a lower cutting force.

Regardless of the tissue removal or retention means, it is advantageous to include a tissue collection device. For example, the catheter may include a lumen or compartment at the distal end to retain the tissue. Likewise, under suction the device may include a tissue trap, such that fluid, blood, or other material may pass, but tissue is retained in the trap. The physician then may monitor the trap to determine that the tissue removed from the septum has been captured, and is not still in the heart. Such a monitoring may be automatically provided, or may be manual by the physician. It is advantageous if such monitoring can be conducted before the catheter is removed from the patient, and as such in one embodiment the trap is exterior to the body and readily accessible by the physician. In another embodiment, the trap is automatically monitored by a sensor, such as an electrode, visual examination, pressure sensor, or the like for the presence and volume of tissue.

Additional cutting means can include a harmonic scalpel, an RF cutter, a high pressure fluid jet, or a laser. The devices can cut by rotation, a high density ring of points, or a low density ring of point that causes perforation in the tissue that can later be separated.

In one embodiment, shown in FIG. 9A the guidewire 705 is first positioned across the septum 730. Guidewire 705 can pierce the septum itself using a sharp tip 706 to cut a small hole in septum 730. Alternatively a separate device, such as a BRK needle (not shown), may be used to pierce the septum. Guidewire 705 may ride over or inside the needle to cross through septum 730.

In one embodiment, once the sheath is in place a transseptal crossing system is used to cross the fossa. Then once across the crossing system is typically replaced with a guidewire. The guidewire 705 remains in position across the interatrial septum and guides either the sheath 700, the catheter 710, or both into position. Guidewire 705 may comprise a retention means on its distal end. In an alternative embodiment, the transeptal crossing system is entirely separate and can cross the septum and position the guidewire before sheath 700 is inserted into the body.

Riding over the top of guidewire 705, the cutting means 716 is positioned next to or near the interatrial septum. The cutting means 716 may be so located through a physician's experience touch and feel, or using the markers, or in conjunction with imaging system.

Once the cutting means 716 or the catheter 710 are located next to or near the target tissue 730 the catheter 710 and/or the cutting means 716 are advanced past the end of or to the end of the sheath and placed in contact with the tissue 730. Preferably using the unique markers the physician can tell on the visualization system when the catheter has exited the sheath 700 or has contacted the tissue. Likewise, the catheter 710 or the cutting means 716 may include sensors (not shown) that identify when it contacts the tissue, at what angle it contacts the tissue, the thickness of the tissue, whether it is through or not through a PFO or a flap, if the cutting is complete, the quality of the cut edge, and the like. Such sensors can include a force sensor, fiber optics, a camera, and electrode using impedance sensing, mapping systems, ultrasound, or the like. In a first embodiment, the circular cutter 716 is advanced into the tissue 730 to cut a circular aperture in the tissue. In an alternative embodiment the sheath 700 is not utilized and the catheter 710 itself is steered into position near tissue 730, and the cutting means 716 is advanced to cut the aperture.

It is preferred that one of the first, second, or third actuators be utilized to advance the catheter 710 out of the sheath 700. It is likewise preferred that an actuator be utilized to advance cutting means 716 out of catheter 710. However, either can be manually advanced without an actuator as well.

In another embodiment the medical device assembly includes a tissue capture component. For example, as shown in FIG. 9A, the assembly may include a distal capture component 750 designed to cross the septum to the distal side. The distal capture component may be attached to the guidewire 705, the sheath 700, or the catheter 710. It may also be attached to a distal capture catheter 755. As such, distal capture catheter 755 may have a lumen and ride over the guidewire 705, but inside a lumen of catheter 710. Such a lumen may be just large enough to fit over a 0.035" guidewire. Distal capture catheter 755 may be advanced by an actuator, or have its own handle.

Once on the distal side of septum 730, the distal capture component may be expanded as shown in FIG. 9B, and brought into contact with the tissue 730. For example, the distal capture component 750 may comprise an expandable balloon or a nitinol basket. The nitinol basket can be comprised of nitinol strands that, when released from confinement (in catheter 710, or the lumen of another element) expand into a circular capture element. The expanded nitinol basket may be flat, e.g., oriented largely parallel to the tissue 730, or it may be 3 dimensional, e.g., resembling a 3 dimensional diamond shape, such that when withdrawn it provides tissue tenting. In some embodiments the distal capture component 750 may pierce and hold the tissue. In some embodiments the tissue capture component 750 is larger than the cutting blade 716. In others, the capture component 750 is smaller than the cutting blade 716. In still others it is substantially the same size as the cutting blade 716, e.g., 6 mm.

In another embodiment the medical device assembly may include a proximal capture component 740 designed to remain at least partially on the proximal side of the septum 730. The proximal capture component may be attached to the guidewire 705, the sheath 700, or the catheter 710. It may also be attached to a proximal capture catheter 745. As such, proximal capture catheter 745 may ride over the guidewire 705, but inside a lumen of catheter 710. proximal capture catheter 745 may be advanced by an actuator, or have its own handle.

In another embodiment, shown in FIGS. 9A-C, the assembly includes both proximal and distal tissue capture components, 740, 750. In this embodiment the tissue capture components may be attached to the same or a different catheter or guidewire. In operation (FIG. 9B) the tissue capture components are brought together to hold the tissue between them, both retaining the tissue in place for the cutting blade 716, and also capturing the tissue for removal (FIG. 9C).

Figure 9D:
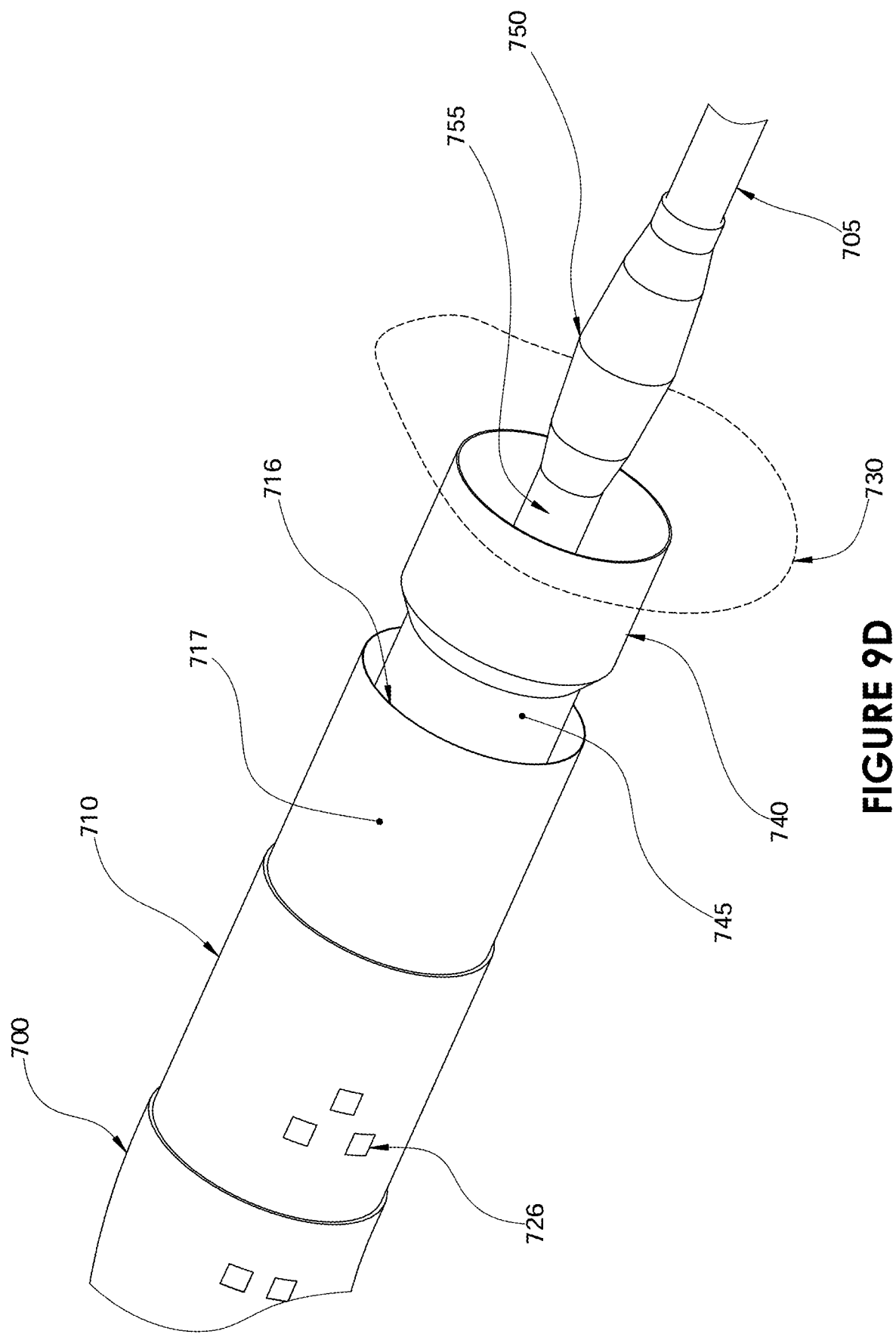
FIG. 9D is a partial perspective view of a catheter constructed according to the present disclosure.

FIG. 9D illustrates an exemplary device made of a distal capture component 750 on the end of a distal capture component shaft 755. The distal capture component 750 and distal capture component shaft 755 have a lumen to accommodate guidewire 705. The proximal capture component 740 is on a proximal capture component shaft 745, and both have a lumen large enough for the distal capture component shaft 755. The cutter 716 and the cutter shaft 717 both have lumens for the proximal capture component shaft 745. All three catheter shafts are assembled as shown and preferably can be advanced together or independently with respect to the other. In use the distal capture component 750 is advanced over a guidewire 705 already across the septum and placed so the proximal edge of this distal capture component 750 is touching the Left Atrial (LA) side of the septal tissue to be removed. Next the proximal capture component 740 is advanced to the Right Atrial (RA) side of this same septal tissue, such that the tissue to be cut and removed is trapped or captured with substantial force between the distal capture component 750 and the proximal capture component 740. The captured tissue then will not stretch as the cutter is advanced. Next the cutter 716 is advanced by advancing the cutter shaft 717 until the tissue captured between the distal capture component and proximal capture component is completely cut from surrounding tissue.

Alternatively, the cutter blade 716 and cutter blade shaft 717 can be advanced over the guidewire and dilator into the RA prior to advancement of the capture components. In some embodiments it will be advantageous to control tissue capture forces for safety and effectiveness. In these cases a sensor 770, and or a strain or force sensor 780 can be attached to the capture components. In a preferred embodiment the force sensor 780 is able to determine how much force is applied to the respective shafts, e.g., force sensor 780 determines how much force is applied to the proximal capture component shaft 745, while force sensor 781 determines how much force is applied to distal capture component shaft 755. By measuring these respective forces the operator is able to determine how firmly the tissue 730 is held between the components. Likewise, in embodiments with only one tissue capture component, the force sensor can identify how firmly that capture component holds the tissue. In the event that the tissue is not firmly held, the operator will be able adjust the positioning, remove the device and reapply it, or the like. Above all, the sensors on the capture component shaft can give the operator an indication of the safety of the operation. If the tissue is not affirmatively held, there is a risk it can break free creating a risk of stroke due to embolization. Accordingly, knowing how well tissue 730 is held by the tissue retention device(s) is critical.

In addition to or in the alternative to force sensors (780, 781) the device may comprise a sensor 770 on the proximal capture component shaft 745, and sensor 771 on the capture component shaft 755. Of course, sensors 770, 771 may be located on the capture components themselves as well. Sensors 770, 771 may be used for one or more purposes, including determining the location of the shafts or components, visualizing the tissue, visualizing the procedure, sensing the impedance of the tissue, sensing the proximity of another sensor or component, and the like. Examples of such sensors include magnets, electromagnetic coils, electrodes, optical strain sensors, electrical strain sensors, cameras, fiber optics, ultrasound, pressure sensors and similar sensors. Likewise, markers such as radiopaque markers or ultrasound markers may be employed on the shafts or components.

There are three broad mechanisms for bringing the tissue capture components 740, 750 together. First, the distal mechanism 750 may be actuated to move proximally into the proximal mechanism 740. Doing so may tent the tissue or bring it into a lumen on the catheter 710 or the proximal mechanism. The tissue may also be retained in a flat configuration (as shown). Second, the proximal mechanism 740 may be actuated to move proximally into the distal mechanism 750. Doing so may tent the tissue or bring it into a lumen on the catheter 710 or the distal mechanism. Finally, the two tissue capture mechanisms 740, 750 may be moved together, e.g., by a double bushing or double basket, to meet at the septum 730, which in some cases may remain in place. Depending on the shape of the mechanism, the tissue may remain flat (FIG. 9b) or may be tented (not shown).

In another embodiment, the components can be spring loaded in a way that consistently applies the same amount of force. For example, the movement of the tissue capture components 740, 750 and the cutting blade 716 may be controlled from one or more handle mechanisms. With reference to FIG. 11A, the handle 780 may have multiple portions 785, 790, 795 that are linearly connected and axially movable along a central handle spindle 782. In a first handle 780 (FIG. 11A) setting the tissue capture components 740, 750 and the cutting blade 716 are contained within the catheter 710. When properly positioned by the tissue 730, a first actuation may occur. In so doing a first handle portion 785 (or actuator) is moved distally as shown in FIG. 11B. The first handle 780 includes a first handle portion stop 787 that controls how far forward the first handle portion 785 may advance. In an alternative embodiment, there may be a stop on the tissue capture component shaft 755, on the guidewire 705, the tissue capture component shaft 745, or the catheter 710 that separately controls the advancement of the first tissue capture component 755. In advancing the first handle portion 785, the distal tissue capture component crosses the tissue 730 by riding over the guidewire through the hole created earlier (FIG. 9A). In one embodiment, upon actuation of actuator 788 the distal capture component 750 is expanded (FIG. 9B).

As shown in FIGS. 11B and 11C, a second handle portion 790 is then moved distally by the operator, which in turn moves the proximal tissue capture component 740 in the distal direction. The first handle 780 may include a stop 792 to control how far the proximal tissue capture component moves, or as above a stop may be included in the distal end of the assembly. The handle or the distal end of the assembly may further include springs 789 or 793 to control the level of tension placed on the two tissue capture components. For example, spring 789 may bias the distal tissue capture component in the proximal direction, while spring 793 may bias the proximal tissue capture component in the distal direction, providing a preset level of force to capture the tissue between the two devices.

Finally, when the tissue is adequately held in place, the third handle portion 795 is then moved distally by the operator, which in turn moves the cutting edge 716 in the distal direction. The first handle 780 may include a stop 797 to control how far the cutting edge 716 moves, or as above a stop may be included in the distal end of the assembly. When the procedure is finished, the operator may then reverse the movement of the handle portions, such that either together or in turn each component is withdrawn into catheter 710. Because tissue capture is critical, it is advantageous if the first and second tissue capture components are withdrawn together, holding the tissue in place.

Because the handle 780 controls how far the various components move, there is a greatly reduced risk of perforations in the left atrium, the procedure is faster, and less stressful for the operator. The handle 780 may further include buttons or actuators that automate the movement of the handle portions.

In another embodiment, once the two capture mechanisms are in place, they are preferably held in place by a closure means. For example, the two capture mechanisms may have respective magnets that are strong enough to hold the capture mechanisms together absent operator input. Likewise, electromagnetic force could be utilized. Alternatively, a locking mechanism may be employed, either at the capture mechanisms (such as a friction lock, or a twist lock) or at the proximal end of the catheter, such as on a handle or actuator.

Figure 12A:
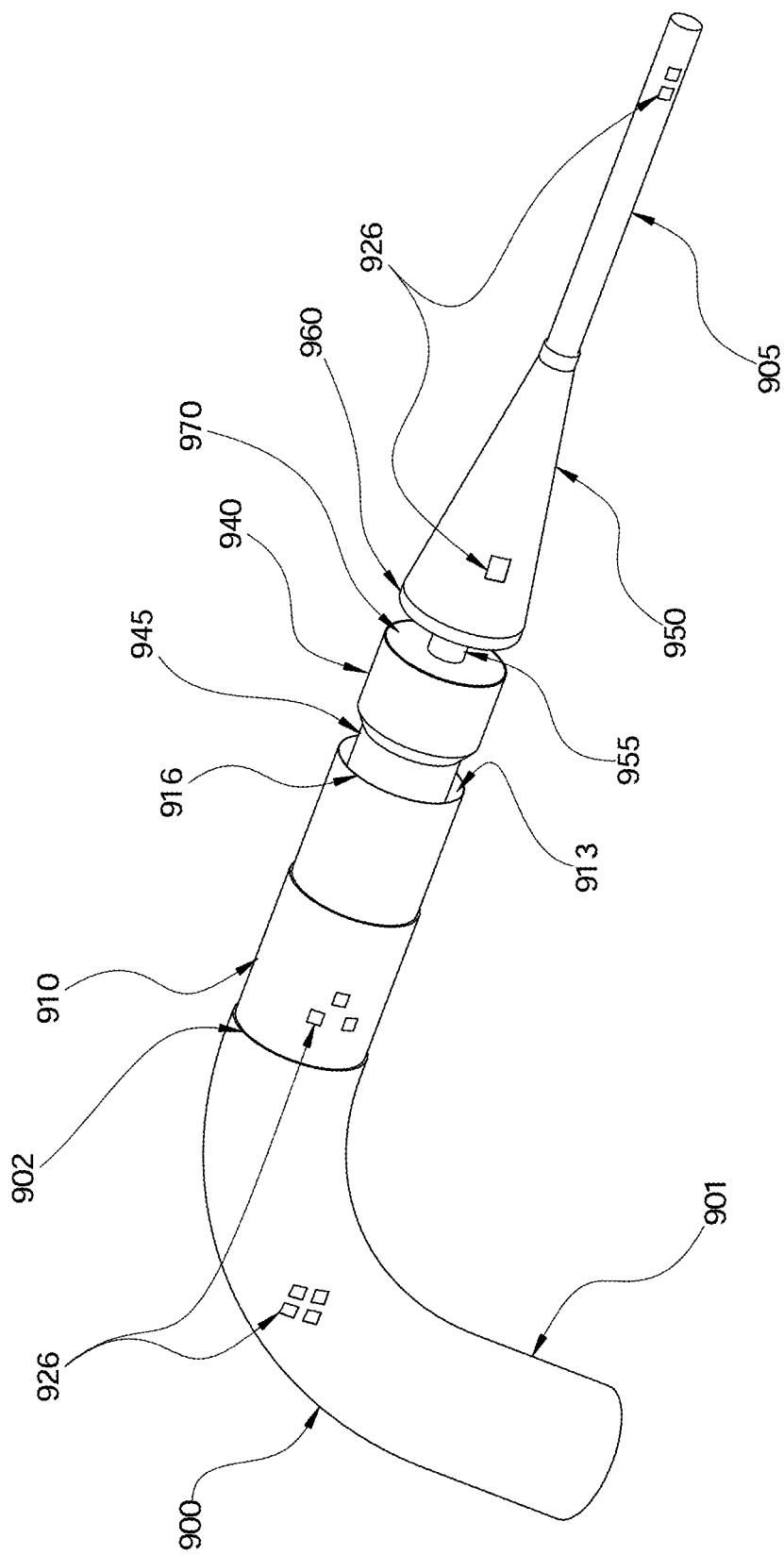
FIG. 12A is a partial perspective view of a catheter constructed according to the present disclosure.
Figure 12D:
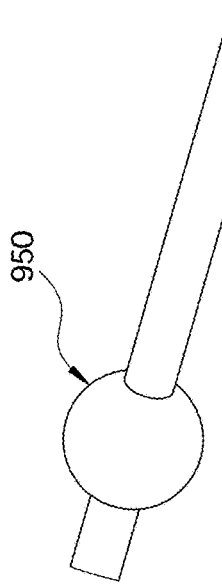
FIG. 12D is a partial perspective view of the distal end of a catheter constructed according to the present disclosure.
Figure 12C:
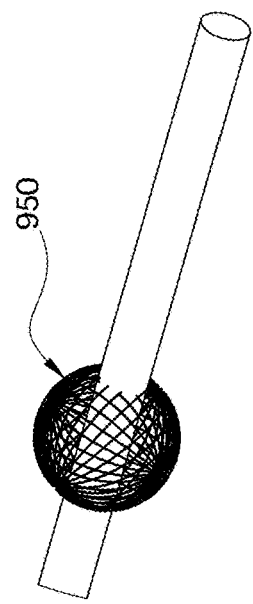
FIG. 12C is a partial perspective view of the distal end of a catheter constructed according to the present disclosure.
Figure 12B:
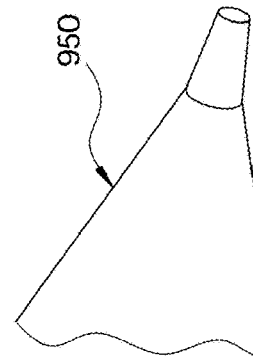
FIG. 12B is a partial perspective view of the distal end of a catheter constructed according to the present disclosure.
Figure 12F:
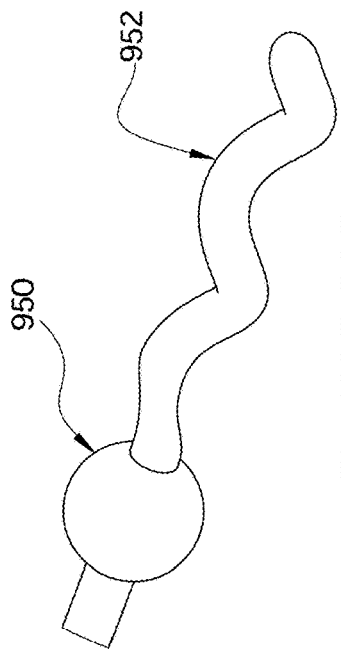
FIG. 12F is a partial perspective view of the distal end of a catheter constructed according to the present disclosure.
Figure 12E:
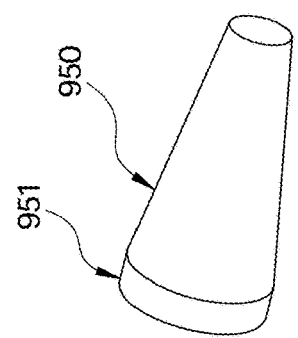
FIG. 12E is a partial perspective view of the distal end of a catheter constructed according to the present disclosure.

Because the distal capture component 750 must cross the septum it is likely to inflict some damage on the tissue. There can be a tradeoff between inflicting minimal damage to the tissue, but yet supporting the cutting action and providing sufficient capture force so the tissue is safely removed. To minimize damage to the tissue the distal capture component may be made of a tapered cone as shown in FIG. 12A, a double tapered cone as shown in FIG. 12b, an expandable metal frame like the nitinol design shown in FIG. 12c, or an expandable balloon design as shown in FIG. 12d. The distal capture component 950 may be designed so that it has a tight fit with the cutter 916, or act as a back-stop for the cutter 916, both facilitating the cutting action. The distal capture component 950 may also be designed to hold a cutter 951 on its proximal end, as seen in FIG. 12e, such that a proximal and distal cutter act in concert to cut the tissue. The device design may also contain a cutter mounted only to the distal capture component. The distal capture component 950 may also be designed with an auger 420 (see FIG. 6) or cork screw 952 (FIG. 120 type configuration to reduce septum tissue tearing while crossing.

Figure 12I:
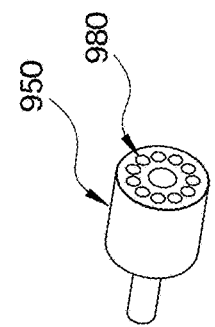
FIG. 12I is a partial perspective view of the distal end of a catheter constructed according to the present disclosure.
Figure 12H:
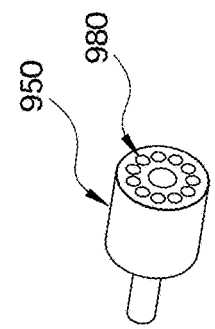
FIG. 12H is a partial perspective view of the distal end of a catheter constructed according to the present disclosure.
Figure 12G:
FIG. 12G is a partial perspective view of the distal end of a catheter constructed according to the present disclosure.

The proximal capture component 940 is designed to fit with the distal capture component 950 so that it provides a high capture force of the tissue, especially at its outer circumference. Interface features of both of these components may be designed with high capture force, roughening surfaces or barbs (12h), edges to the surfaces (12g), and vacuum ports (12i) as seen in FIGS. 12h-i. As detailed above, the capture components may also comprise a balloon, a pigtail (not shown), an expandable nitinol basket (not shown), an disk or expandable disk (not shown) or similar means. In some embodiments a single capture mechanism can hold both proximal and distal sides of the tissue. A balloon for example may be narrow in the middle and broad at both ends, essentially surrounding the tissue it passes through. An Auger can have surfaces on both sides of the tissue as well, for example.

In an embodiment one or more tissue capture components will pull the tissue of the interatrial septum into a lumen 713 of catheter 710 such that the tissue is tented, preferably into the catheter's lumen or into a lumen on the distal capture mechanism 750. Once the tissue is tented the cutter 716 will cut the tissue 730 resulting in a larger aperture due to the tenting. Tenting the tissue has several advantages. First in many cases it will allow for a larger aperture size combined with a smaller catheter size. Likewise it may give the physician a degree of control over the size the aperture. For example if the physician desires a smaller aperture for a particular patient, he may wish to reduce the amount of tenting or keep it to a minimum. If the physician desires a larger aperture for the patient he will increase the amount of tenting pulling the tissue further into the lumen 713 creating a larger aperture when the cutting means 716 is applied.

In another embodiment the guidewire may include a tissue capture component, such as a pigtail or hook. The tissue cut from the interatrial septum to complete the aperture is positively retained by the guidewire and pulled inside the catheter 710 when the guidewire is withdrawn from the body and into catheter 710. While the guidewire has been described as having either a balloon or pigtail, other articulation and tissue retention devices are contemplated. In particular a disc device can be utilized. The disc device may include one disc that is navigated to the distal side of tissue 730, or may include a disc on each side of the tissue 730. The two discs may be actuated to secure the tissue between them. The disc may be expandable having a small diameter when crossing the septum and a larger diameter when securing the tissue. Cutter 716 may ride over the discs, pulling them into lumen 713, to cut the tissue which then remains retained between the two discs and is removed from the body.

Figure 13:
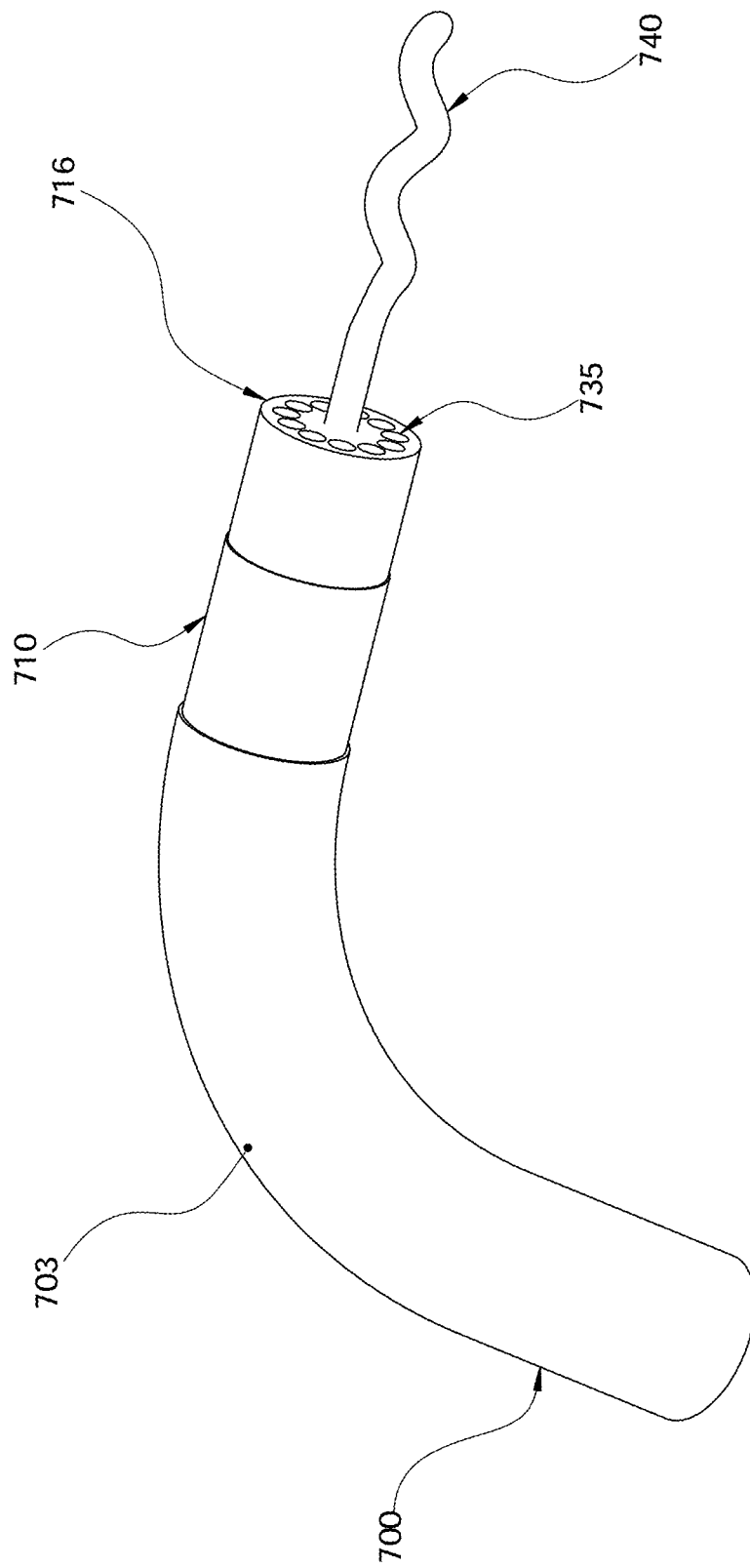
FIG. 13 is a partial perspective view of a catheter constructed according to the present disclosure.

In one embodiment the assembly may not cross the tissue 730. As shown in FIG. 13, this assembly omits the guidewire 705 and could optionally omit the sheath 700, though in embodiments the sheath 700 still provides stability and anchoring as discussed above.

In this embodiment the distal end of catheter 710 is delivered or directed to the tissue 730 as discussed above. A proximal tissue retention means 740 may be employed to grab the tissue from the proximal side. For example, a corkscrew device 740 may be engaged with the tissue such that it holds the tissue in place. Other mechanisms are contemplated, including hooks, forceps, barbs, adhesives, and suction. For example, catheter 710 may employ one or more suction ports 735 to apply suction to the tissue 730. Suction ports 735 may be arranged on opposite sides (e.g., every 180 degrees), every 90 degrees, in a ring of ports, or in a continuous circle inside of or outside of the cutting mechanism 716. In this embodiment the suction is employed to remove any tissue or debris that comes loose during the procedure, ensuring that no embolic material escapes.

In some embodiments ultrasound or similar can be applied to the blade to reduce the force to cut tissue. This may be especially advantageous for cutting through fibrous tissue. Also, an ultrasonic pressure reduction, or vacuum assistance, within the lumen of the cutter can be used to help pull tissue into the blade.

Figure 10D:
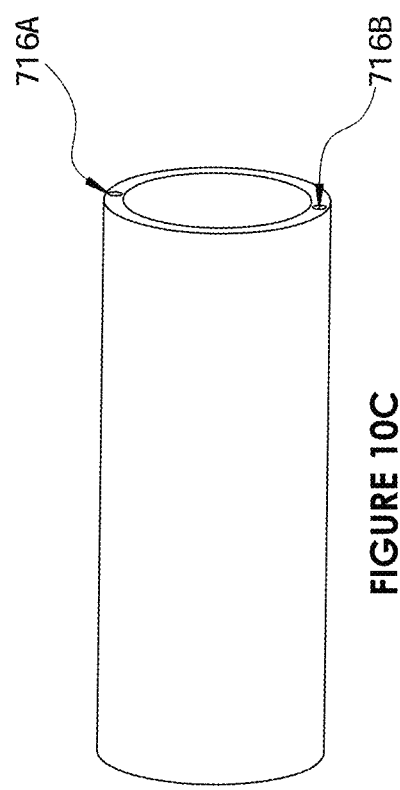
FIG. 10D is a partial perspective view of a cutter constructed according to the present disclosure.
Figure 10C:
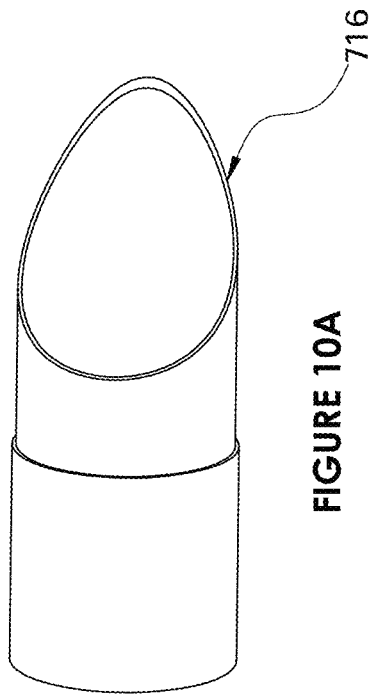
FIG. 10C is a partial perspective view of a cutter constructed according to the present disclosure.

An energy source cutter may also reduce cutting forces. These include a laser or RF cutter with multiple emitters 716a, b (as shown in FIG. 10C) or rotating (as shown in FIG. 10D) designs. A photoselective laser or holmium laser, for example, could be used to ablate all septal tissue needed to create the hole, so no tissue is left for removal. As shown in FIG. 14a, the distal portion of catheter 710 may consist of a pattern of fiber optic cables 800. As shown in FIG. 14A, the pattern may be round, or it may be another pattern, e.g., a line, and x shape, a square, or other. As shown in FIG. 14B, the fiber optic cables 800 may saturate the distal portion of catheter 710.

The fiber optic cables 800 terminate at a proximal end where they are operationally connected to a laser system, e.g., an Excimer Laser System, to provide laser energy for photoablation of the tissue, using light to break down, vaporize, or remove the tissue 730. Preferably the distal end of the catheter 710 includes radiopaque markers 726 and a visualization system for visualizing when the tissue has been vaporized.

In one embodiment, the distal portion of the sheath 700 (or the catheter 710) further comprises a suction means 820 to hold a hood 810 tightly to the tissue 730, and over the fiber optic cables 800. In operation the suction means 820 removes the blood from between the fiber optic cables 800 and the tissue. Preferably, the embodiment includes irrigation ports 830 to provide saline to replace the blood.

Similarly, the distal portion of catheter 710 may comprise an electrode designed to provide pulsed plasma RF energy to the tissue 730. Such an electrode may be a unipolar or a bipolar designs, and one electrode could be on each side of the tissue 730. In the alternative, an aperture could be cut in tissue 730 using a design similar to FIG. 10d, but with a fluid jet as a cutter.

In another embodiment, as shown in FIG. 12A, a medical device assembly includes a sheath 900, a catheter 910, and a guidewire 905. While the following description describes the sheath 900, catheter 910 and guidewire 905 as separate devices, it is understood that they equally can be a single device, be integrally connected (but preferably laterally moveable relative to each other), and be controlled by the same or different proximal handles and electrical connections. In particular, the attributes of the sheath 900 and catheter 910 may be advantageously combined. Likewise, the sheath, catheter, or guidewire may be omitted.

Sheath 900 comprises an elongated catheter shaft 901 having a distal end 902 and a proximal end (not shown). The proximal end includes a handle (not shown). The handle may comprise actuators, such as a first actuator, a second actuator, and a third actuator. It is understood that in the case of multiple handle units on different portions of the assembly, any one of the actuators discussed in the following may be on different handles connected to any of the three components (sheath, catheter, guidewire). The handle(s) may further include a fluid port(s) and electrical connection(s) (not shown). Sheath 900 and/or catheter 910 may further include pull wires attached to an actuator for actuating distal elements, moving a lumen or shaft, steering, or the like. Sheath 900 and/or catheter 910 may further include irrigation ports and the like.

Sheath 900, guidewire 905, and/or catheter 910 further include markers 926, 928 as discussed above with respect to FIGS. 9a-d. In another embodiment, spot electrodes may be used and provide a pattern. In another embodiment, an electroanatomical mapping system is programmed or provided with the specifics of the three components. The specific electrodes, magnetic coils, or other electrodes are identified to the mapping system, e.g., through an EEPROM in the catheter or otherwise, and as the system identifies a specific electrode or coil (e.g., by the current passed through the electrode or coil and to the other components of the mapping system). The mapping system may then clearly and visually identify the location of the three components for the physician.

Sheath 900, guidewire 905 and catheter 910 may alternatively or further include ultrasound markers (not shown) again preferably in designed patterns as described above such that the physician may locate the components in the patient on ultrasound imaging. In an alternative embodiment, in place or in addition to radiopaque markers 926, the sheath 900, guidewire 905, and catheter 910 may have electrodes (not shown) that are locatable on an electroanatomical mapping system such as the EnSite™ electroanatomical mapping system. Alternatively, the sheath 900, guidewire 905, and catheter 910 may have magnetic coils locatable on the Carto™ or MediGuide™ mapping systems.

The elongated shaft 901 is preferably hollow, having a lumen 913 that has the ability to pass the catheter 910 and guidewire 905 through it. The catheter 910 is designed to work in conjunction with sheath 900. Sheath 900 may either extend the entire length from the percutaneous incision to the left atrium of the heart, or may only cover a portion of catheter 710.

As discussed above, the sheath 900 and the catheter 910 are designed to provide the operator with the ability to provide a right angle approach to the tissue. In one such embodiment, in the manner discussed above, sheath 900 extends to the steering/bend 903. In this embodiment the sheath 900 may terminate before the bend 903, and as such the medical assembly is preferably steered/bent by pull wires in catheter 910. However, in another embodiment, the sheath 900 terminates distally of bend 903. Pull wires or biasing in the sheath 900 enable it to make a sufficient turn to orient catheter 910 toward the interatrial septum. While in one embodiment the catheter 910 does not have its own biasing or pull wires, in another embodiment the catheter 910 may be separately steerable or biased.

On the other hand, providing a biasing agent such as a nitinol wire to provide a preformed bend provides the advantage of having a less expensive manufacturing process and a simpler device. However, multiple bend sizes may need to be manufactured.

In another embodiment, the sheath 900 may have a first preformed bend, and the catheter 910 may have a second preformed bend. The first and second preformed bends work together to allow the operator to direct the cutting blade 916 to the septum at a right angle. Likewise, the catheter 910 may have multiple preformed bends. The sheath 900 and the catheter 910 may include braiding to provide stiffening. Sheath 900 and catheter 910 may further include irrigation ports (not shown).

The distal end of catheter 910 comprises a distal tissue capture dilator 950. Distal tissue capture dilator is shown as a conical dilator, but may take on the shape and characteristics of the dilators shown in FIGS. 12A and 12b-f. In one embodiment, distal tissue capture dilator 950 comprises a cutting blade on its proximal portion. In another embodiment, distal tissue capture dilator 950 comprises a cutting blade 952 on its distal portion for punching a hole through the tissue (FIG. 15A). Distal tissue capture dilator 950 may also have a lumen 951 through it for a guidewire, 905 as shown in FIG. 15B.

The distal capture component 950 may be attached to the guidewire 905, the sheath 900, or the catheter 910. It may also be attached to a distal capture catheter 955 as shown. As such, distal capture catheter 955 may have a lumen and ride over the guidewire 905, but inside a lumen of catheter 910. Distal capture catheter 955 may be advanced by an actuator, or have its own handle.

Once on the distal side of septum, the distal capture component may be expanded as shown in FIG. 5, and brought into contact with the tissue. In some embodiments the distal capture component 950 may pierce and hold the tissue. In some embodiments the tissue capture component 950 is larger than the cutting blade 916, e.g., has a larger diameter. In others, the capture component 950 is smaller than the cutting blade 916, e.g., has a smaller diameter. In still others it is substantially the same diameter as the cutting blade 916, e.g., 6 mm.

In another embodiment the medical device assembly may include a proximal capture component 940 designed to remain at least partially on the proximal side of the septum. The proximal capture component may be attached to the guidewire 905, the sheath 900, or the catheter 910. It may also be attached to a proximal capture catheter 945. As such, proximal capture catheter 945 may ride over the guidewire 905, but inside a lumen of catheter 910. proximal capture catheter 945 may be advanced by an actuator, or have its own handle.

In another embodiment, shown in FIG. 12, the assembly includes both proximal and distal tissue capture components, 940, 950. In this embodiment the tissue capture components may be attached to the same or a different catheter or guidewire. In operation the tissue capture components may be at a fixed distance from each other, such that after distal tissue capture component 950 passes through the tissue, the elasticity of the tissue causes it to close completely or partially around the distal tissue capture shaft 955. In another embodiment, the tissue capture components 940, 950 are relatively slidable, and the gap between them is closed so that the tissue is securely held between them, both retaining the tissue in place for the cutting blade 716, and also capturing the tissue for removal (FIG. 9c).

FIG. 12A illustrates an exemplary device made of a distal capture component 950 on the end of a distal capture component shaft 955. The distal capture component 950 and distal capture component shaft 955 have a lumen to accommodate guidewire 905. The proximal capture component 940 is on a proximal capture component shaft 945, and both have a lumen large enough for the distal capture component shaft 955. The cutter 916 and the cutter shaft 917 both have lumens for the proximal capture component shaft 945. All three catheter shafts are assembled as shown and preferably can be advanced together or independently with respect to the other. In use the distal capture component 950 is advanced over a guidewire 905 already across the septum and placed so the proximal edge of this distal capture component 750 is touching the Left Atrial (LA) side of the septal tissue to be removed. Next the proximal capture component 940 is advanced to the Right Atrial (RA) side of this same septal tissue, such that the tissue to be cut and removed is trapped or captured with substantial force between the distal capture component 950 and the proximal capture component 740. The captured tissue then will not stretch as the cutter is advanced. Next the cutter 916 is advanced by advancing the cutter shaft 917 until the tissue captured between the distal capture component and proximal capture component is completely cut from surrounding tissue. In an alternative embodiment, cutting edge 960 and cutter 916 operate together with a scissor action to cut the tissue. In another embodiment, cutter 916 is absent and cutting edge 960 cuts the tissue.

In a first embodiment the cutting means 916 is a razor like member formed of steel or another suitable metal or material adapted to cut a thin tissue. Cutting means 916 can take any form discussed herein, including the forms disclosed in FIGS. 10A-D, a shaped blade, a saw blade, a rotary blade or the like.

Once the cutting means 916 or the catheter 910 are located next to or near the target tissue the catheter 910 and/or the cutting means 916 are advanced past the end of or to the end of the sheath and placed in contact with the tissue. Preferably using the unique markers the physician can tell on the visualization system when the catheter has exited the sheath 900 or has contacted the tissue. Likewise, the catheter 910, the dilator 950, the proximal tissue capture component 740, their respective catheter shafts, and the cutting means 916 may include sensors (not shown) that identify when it contacts the tissue, such as a force sensor, fiber optics, a camera, and electrode using impedance sensing, mapping systems, ultrasound, or the like. In a first embodiment, the circular cutter 916 is advanced into the tissue to cut a circular aperture in the tissue. In an alternative embodiment the sheath 900 is not utilized and the catheter 910 itself is steered into position near tissue, and the cutting means 916 is advanced to cut the aperture.

It is preferred that one of the first, second, or third actuators be utilized to advance the catheter 910 out of the sheath 900. It is likewise preferred that an actuator be utilized to advance cutting means 916 out of catheter 910. However, the catheter 910 can be manually advanced without an actuator as well.

In some embodiments it will be advantageous to control tissue capture forces for safety and effectiveness. In these cases a sensor 970, and or a strain or force sensor can be attached to the capture components. In a preferred embodiment the force sensor 970 is able to determine how much force is applied to the respective shafts, e.g., one or more force sensor(s) 970 determines how much force is applied to the proximal capture component shaft 945, while another force sensor determines how much force is applied to distal capture component shaft. By measuring these respective forces the operator is able to determine how firmly the tissue is held between the components. Likewise, in embodiments with only one tissue capture component, the force sensor can identify how firmly that capture component holds the tissue.

Sensors may be used for one or more purposes, including determining the location of the shafts or components, visualizing the tissue, visualizing the procedure, sensing the impedance of the tissue, sensing the proximity of another sensor or component, and the like. Examples of such sensors include magnets, electromagnetic coils, electrodes, optical strain sensors, electrical strain sensors, cameras, fiber optics, ultrasound, and similar sensors. Likewise, markers such as radiopaque markers or ultrasound markers may be employed on the shafts or components.

There are three broad mechanisms for bringing the tissue capture components 940, 950 together, as discussed above and incorporated here. In another embodiment, the components can be spring loaded in a way that consistently applies the same amount of force, as also discussed above in connection with FIGS. 11a-c. Because the handle controls how far the various components move, there is a greatly reduced risk of perforations in the left atrium, the procedure is faster, and less stressful for the operator. In another embodiment, once the two capture mechanisms are in place, they are preferably held in place by a closure means. For example, the two capture mechanisms may have respective magnets that are strong enough to hold the capture mechanisms together absent operator input. Likewise, electromagnetic force could be utilized. Alternatively, a locking mechanism may be employed, either at the capture mechanisms (such as a friction lock, or a twist lock) or at the proximal end of the catheter, such as on a handle or actuator.

Because the distal capture component 950 must cross the septum it is likely to inflict some damage on the tissue. There can be a tradeoff between inflicting minimal damage to the tissue, but yet supporting the cutting action and providing sufficient capture force so the tissue is safely removed. To minimize damage to the tissue the distal capture component may be made of a tapered cone as shown in FIG. 12A, a double tapered cone as shown in FIG. 12b, an expandable metal frame like the nitinol design shown in FIG. 12c, or an expandable balloon design as shown in FIG. 12d. The distal capture component 1 may be designed so that it has a tight fit with the cutter 916, or act as a back-stop for the cutter 916, both facilitating the cutting action. The distal capture component 950 may also be designed to hold a cutter 951 on its proximal end, as seen in FIG. 12e, such that a proximal and distal cutter act in concert to cut the tissue. The device design may also contain a cutter mounted only to the distal capture component. The distal capture component 950 may also be designed with an auger 420 (see FIG. 6) or cork screw (FIG. 12f) type configuration to reduce septum tissue tearing while crossing.

In the embodiment shown in FIG. 12A, the proximal capture component 940 is designed to fit with the distal capture component 950 so that it provides a high capture force of the tissue, especially at its outer circumference. Interface features of both of these components may be designed with high capture force, roughening surfaces or barbs (12h), edges to the surfaces (12g), and vacuum ports (12i) as seen in FIGS. 12h-i. As detailed above, the capture components may also comprise a balloon, a pigtail (not shown), an expandable nitinol basket (not shown), an disk or expandable disk (not shown) or similar means. In some embodiments a single capture mechanism can hold both proximal and distal sides of the tissue. A balloon for example may be narrow in the middle and broad at both ends, essentially surrounding the tissue it passes through. An Auger can have surfaces on both sides of the tissue as well, for example.

In an embodiment one or more tissue capture components will pull the tissue of the interatrial septum into a lumen 913 of catheter 910 such that the tissue is tented, preferably into the catheter's lumen or into a lumen on the distal capture mechanism 950. Once the tissue is tented the cutter 916 will cut the tissue resulting in a larger aperture due to the tenting. Tenting the tissue has several advantages. First in many cases it will allow for a larger aperture size combined with a smaller catheter size. Likewise it may give the physician a degree of control over the size the aperture. For example if the physician desires a smaller aperture for a particular patient, he may wish to reduce the amount of tenting or keep it to a minimum. If the physician desires a larger aperture for the patient he will increase the amount of tenting pulling the tissue further into the lumen 913 creating a larger aperture when the cutting means 916 is applied.

Figure 16A:
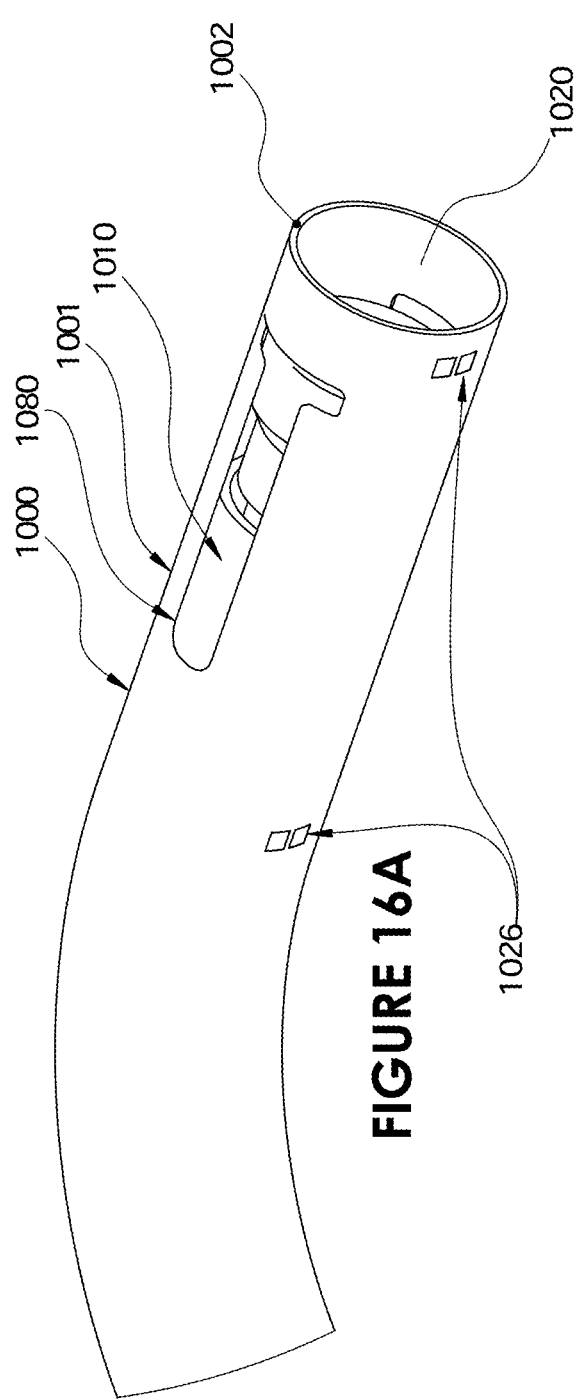
FIG. 16A is a partial perspective view of a catheter constructed according to the present disclosure.

In another embodiment, shown in FIGS. 16a-c, a medical device assembly includes a sheath 1000 that comprises an elongated catheter shaft 1001 having a distal end 1002 and a proximal end (not shown). The proximal end includes a handle (not shown). The handle may comprise actuators, such as a first actuator, a second actuator, and a third actuator. It is understood that in the case of multiple handle units on different portions of the assembly, any one of the actuators discussed in the following may be on different handles connected to any of the three components (sheath, catheter, guidewire). Likewise, one or more elements may not have a handle, such as the guidewire. The handle(s) may further include a fluid port(s) and electrical connection(s) (not shown). Sheath 1000 may include an inner catheter 1010 may further include pull wires attached to an actuator for actuating distal elements, moving a lumen or shaft, steering, or the like. Sheath 1000 and/or catheter 1010 may further include irrigation ports and the like. While a guidewire is not pictured, and in one embodiment is not used, in another embodiment a guidewire (not shown) may be used to guide the catheter to the tissue.

Sheath 1000, and/or catheter 1010 further include markers 1026 as discussed above with respect to FIGS. 9a-d. In another embodiment, spot or ring electrodes may be used and provide a pattern. In another embodiment, an electroanatomical mapping system is programmed or provided with the specifics of the three components. The specific electrodes, magnetic coils, or other electrodes are identified to the mapping system, e.g., through an EEPROM in the catheter or otherwise, and as the system identifies a specific electrode or coil (e.g., by the current passed through the electrode or coil and to the other components of the mapping system). The mapping system may then clearly and visually identify the location of the three components for the physician.

Sheath 1000 and catheter 1010 may alternatively or further include ultrasound markers (not shown) again preferably in designed patterns as described above such that the physician may locate the components in the patient on ultrasound imaging. In an alternative embodiment, in place or in addition to radiopaque markers 1026, the sheath 1000, and catheter 1010 may have electrodes (not shown) that are locatable on an electroanatomical mapping system such as the EnSite™ electroanatomical mapping system. Alternatively, the sheath 1000 and catheter 1010 may have magnetic coils locatable on the Carto™ or MediGuide™ mapping systems.

The elongated shaft 1001 is preferably hollow, having a lumen that has the ability to pass the catheter 1010 through it. The catheter 1010 is designed to work in conjunction with sheath 1000. Sheath 1000 may either extend the entire length from the percutaneous incision to the left atrium of the heart, or may only cover a portion of catheter 1010.

To achieve a consistent aperture of the shape desired by the physician, it is desirable that the cutting blade enter the tissue 1030 (FIG. 16b) perpendicularly to the tissue 1030. Unlike that taught in the prior art devices, where the angle of tissue approach is not addressed, the inventors herein have found that the more squarely the cutting blade 1016 or blades 1016a, b, addresses the tissue 1030, the more predictable the size of the aperture and the quality of the aperture. In addition, the cut is safer as the blade is less likely to encounter unintended tissue on the septum or the atrial wall. Accordingly, the sheath 1000 and the catheter 1010 are designed to provide the operator with the ability to provide a right angle approach to the tissue.

In one such embodiment, sheath 1000 extends to a bend (not shown). In this embodiment the sheath 1000 may terminate before the bend, and as such the medical assembly is preferably steered/bent by one or more pull wires or fibers in catheter 1010, or by a push wire, preshaped rod, or similar means. However, in another embodiment, the sheath 1000 terminates distally of the bend.

In one particular embodiment depicted in FIGS. 16*a-c*, it is especially advantageous for the sheath 1000 to travel to the tissue 1030 as the actuation of the cutting mechanism 1016 may be controlled by movement of the sheath.

Pull wires or biasing in the sheath 1000 enable it to make a sufficient turn to orient catheter 1010 toward the interatrial septum. While in one embodiment the catheter 1010 does not have its own biasing or pull wires, in another embodiment the catheter 1010 may be separately steerable or biased.

On the other hand, providing a biasing agent such as a nitinol wire to provide a preformed bend provides the advantage of having a less expensive manufacturing process and a simpler device. However, multiple bend sizes may need to be manufactured.

In another embodiment, the sheath 1000 may have a first preformed bend, and the catheter 1010 may have a second preformed bend. The first and second preformed bends work together to allow the operator to direct the cutting blade 1016 to the septum at a right angle. Likewise, the catheter 1010 may have multiple preformed bends. The sheath 1000 and the catheter 1010 may include braiding to provide stiffening. Sheath 1000 and catheter 1010 may further include irrigation ports (not shown). Together or in place of the sheath, the device contemplates providing anchoring means or stabilizing means (not shown) to prevent the catheter and the cutting blade from shifting and thus allowing a clean cut in the desired location.

In a first embodiment the cutting means 1016 is a razor like member formed of steel or another suitable metal or material adapted to cut a thin tissue. Cutting means 1016 can take any form discussed herein, including the forms disclosed in FIGS. 10A-D, a shaped blade, a saw blade, a rotary blade or the like.

In another embodiment, the cutting means 1016 comprises twin blades 1016*a,b*. Cutting blades 1016*a,b* are connected to catheter 1010 by flexible members 1017*a,b*. For example, flexible members 1017*a,b* could be a leaf spring. Preferably the flexible members 1017*a,b* bias the cutting blades 1016*a,b* toward the central axis of catheter 1010. The distal most and radially inner most edge of the cutting blades 1016*a,b* are sharpened for cutting tissue. Cutting blades 1016*a,b* may include additional cutting features, such as teeth, vibration, rotation and the like, as discussed above. Additionally, while two cutting blades are pictured, other numbers are contemplated, particularly 1, 3, and 4 blades. The cutter could have a collet design instead of cutters, or a circular blade.

While the sheath 1000 assembly navigates through the body to the surgical site, the flexible members 1017*a,b*, and the cutting blades 1016*a,b* are folded into the lumen 1020 of the catheter 1010. As such they do not present an impediment to the motion of the catheter through the vasculature. When the catheter is properly positioned at the tissue 1030, the proximal tissue capture mechanism 1040 is advanced forward, as discussed above. Originally located behind cutting blades 1016*a,b*, the tissue capture mechanism was fully out of the way of these blades, and accordingly they were folded into the lumen 1020 of the catheter 1010. However, when it is moved distally, proximal tissue capture mechanism forces the blades 1016*a,b* radially outward. For example, blade 1016*a* is forced radially outward through cutout 1080.

Tissue capture mechanism 1040 may comprise any tissue capture mechanism discussed herein. In one embodiment the blades 1016 are the tissue capture mechanism in that they are adapted to grab the tissue to be cut. It can be advantageous to have a locking mechanism to hold the blades 1016*a, b*, in locked and closed state once the tissue has been cut so that the blades 1016 would also function as a tissue removal mechanism. For example, a handle may have an actuator for moving the blades, and this actuator may include a lock to lock the blades in place so that they may not be inadvertently opened to release the tissue.

Figure 16D:
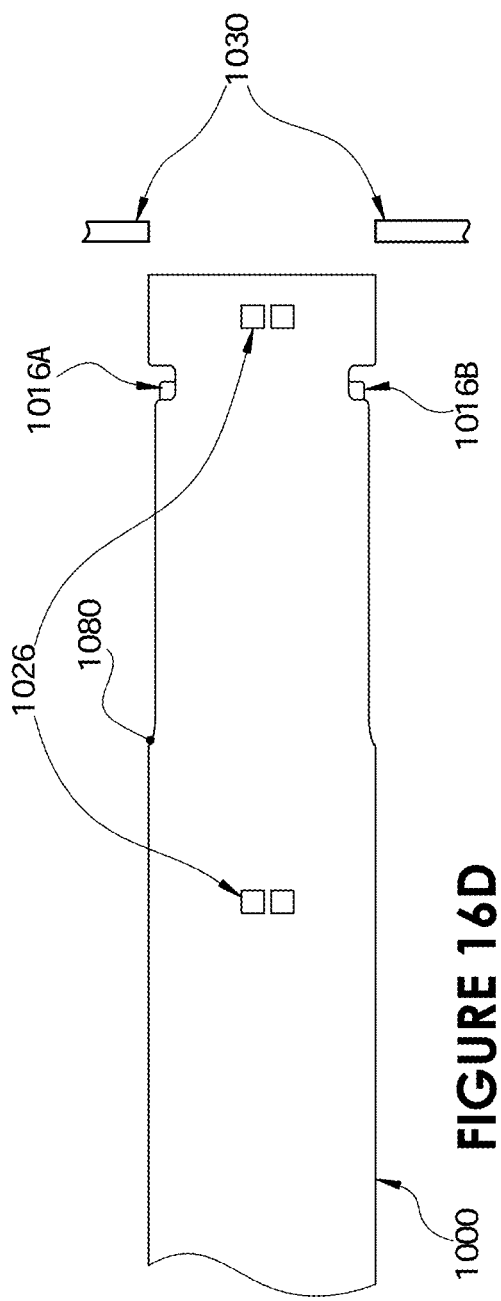
FIG. 16D is a partial perspective view of the distal end of a catheter constructed according to the present disclosure.

In a preferred embodiment, tissue capture mechanism 1040 comprises a lumen 1070 that conveys suction to the tissue 1030. When the operator identifies that the distal end of the assembly is in contact with the desired portion of the tissue (and preferably at a right angle thereto), the suction may be activated. The tissue 1030 is pulled into the lumen 1020. At this point, in one embodiment the tissue capture mechanism is withdrawn proximally pulling the tissue into the lumen (and tenting the tissue, allowing an increased aperture size). As the proximal tissue capture mechanism passes the blades 1016*a,b*, it releases them from the radially outward position. They will close on, and cut the tissue 1030, leaving an aperture in tissue 1030 (FIG. 16*d*).

In an alternative embodiment, when the tissue is in place and subject to suction, the operator pulls back on the shaft. The blades at this point open as they are biased or normally open and are only held in place by the shaft during insertion to the body. Once the shaft is pulled back the tissue is then pulled into the blades with the suction. Once the tissue is inside the blades the shaft is advanced to close the blades, cutting the tissue as well as retaining it. In the alternative, the suction may not be applied prior to shaft pullback, but may first be applied after the blades are open.

In this embodiment the distal end of shaft 1080 is advanced to close the blades as the shaft slides distally, cutting the tissue. The shaft then remains forward, either locked in position or held in position by friction or the doctor, such that the tissue is captured and cannot be accidentally released.

While FIG. 16*b* depicts a central lumen to provide the suction, in another embodiment multiple lumens—for example in a roughly circular pattern—grab the tissue.

While in the above embodiment the tissue is retained with suction, other tissue capture mechanisms are contemplated, such as a forceps, a barb, an auger, hooks, a corkscrew. Of course, multiple tissue retention means may be utilized, such as suction with an auger to hold a location steady, hooks, a corkscrew, or the like. The initial capture may be additionally secured with additional grasping jaws, a collet, or similar means.

Preferably using unique markers or sensors on the different components of this assembly, the physician can tell on a visualization system when the blades have exited the sheath, the tissue retention mechanism has contacted the tissue, the mechanism has withdrawn into the catheter with the tissue, and the blades have closed cutting the tissue. Likewise, the assembly components may include sensors (not shown) that identify when they contacts the tissue, such as a force sensor, fiber optics, a camera, and electrode using impedance sensing, mapping systems, ultrasound, or the like. In another embodiment the blades have respective sensors that identify when they have contacted the tissue retention mechanism, and when they have contacted each other completing a cut.

While the sheath 1000 and catheter 1010 assembly is straightforward to operate without handles and actuators, in one embodiment one or more handles have one or more actuators to control the steering of the assembly, the advancement of the proximal tissue capture mechanism, or the operation of the blades. For example, the blades may remain in an open position even after the tissue capture mechanism 1040 passes proximally, and only close upon actuation by the operator. The actuation may provide additional force to increase the cutting mechanism's effectiveness. Likewise, the cutting mechanism may be assisted by a mutual attraction (e.g., magnetic or electromagnetic) or repulsion. Additionally, the actuation can be utilized to help control the size of the aperture, in that the farther the tissue is drawn into the lumen, the larger the aperture will be. Once closed, the cutting mechanism may help retain the tissue in the catheter.

Because this embodiment need not cross the septum and can remain entirely in the right atrial side, the procedure is simpler, faster, and does not need as many expensive medical devices. In addition, as the procedure is entirely in the right atrium, irrigation is not required to avoid thrombus in the catheter. The absence of a perforating needle eliminates the risk of a perforation to the left atrial wall. It also has the advantage that it can readily provide a second aperture, as the tissue from the first aperture will not interfere with the action of the device.

Figure 17A:
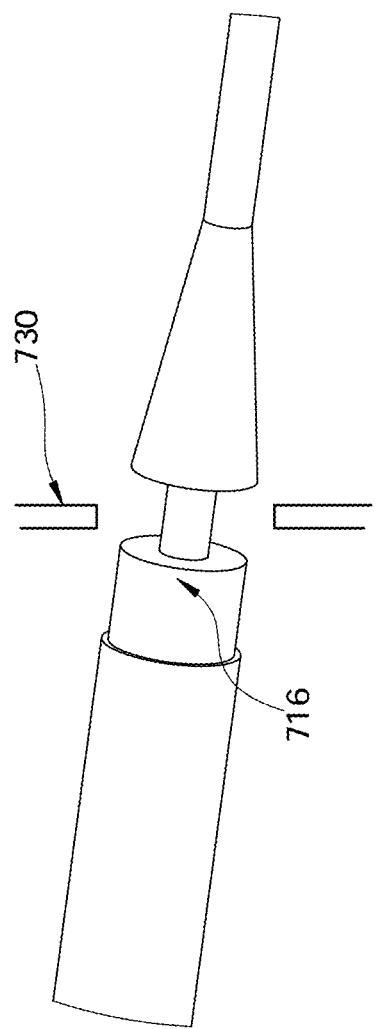
FIG. 17A is a partial perspective view of the distal end of a catheter constructed according to the present disclosure making a second cut.
Figure 17B:
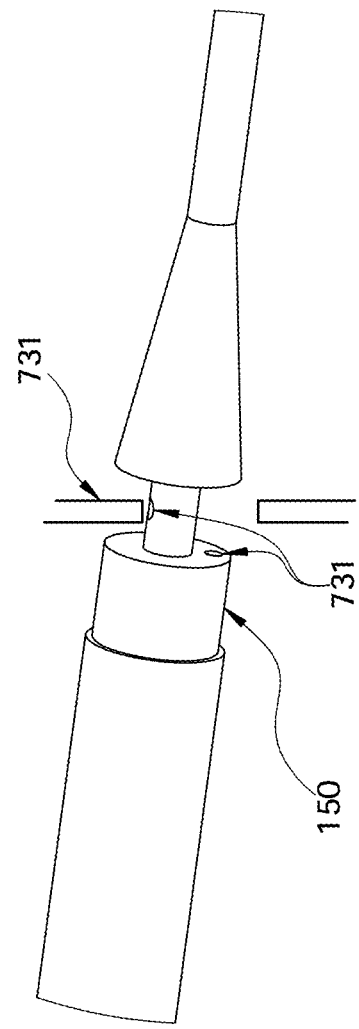
FIG. 17B is a partial perspective view of the distal end of a catheter constructed according to the present disclosure making a second cut.

Once a hole is created in the septal wall there are two ways to increase the area of removed tissue. The first is to simply create another hole. The second way to increase the area of removed tissue in the wall is to enlarge a present hole. To enlarge an existing hole the cutter 716, which may be a blade, energy source or the like as described above, is preferably aligned in the plane of the septum 730 as in FIG. 17a. Then the cutter 716 must be moved within the plane of the septum 730 to engage the septal tissue edge, 731 as shown in FIG. 17b. A tissue cookie can be cut and removed, or the laser or RF vaporizing technologies can be used to vaporize all the additional tissue meant for removal. The movements, cutter, and tissue to be cut will be relatively small compared to common imaging capabilities, and the imaging capability may only be 2D. Accordingly, the catheter 710 includes sensors 780 such an impedance, ultra sound, OCR, etc. to localize the tissue to be cut with respect to the cutter. The sensor 780 could alternatively be a suction port or orifice (a hole). The sensor(s) can be on the device, in the cutter element, or anywhere in the cutting region. In one embodiment the same optical fiber used for laser cutting can also be used for tissue sensing, or the same RF electrodes used for tissue cutting can be used to sense the orientation of tissue within the cutter region.

In the suction case if a low pressure can be pulled on the orifice it may be expected that it is blocked by tissue and tissue is ready to cut. Likewise, a biopsy type forceps with sensing capability is used to increase hole diameter by grabbing a portion of tissue for the cutter to cut. To facilitate controlled catheter movements a catheter handle can be locked in place with respect to the septal wall, e.g., by fastening the handle, the sheath, or the catheter to the patient's bedside.

Regardless of the tissue removal or retention means, it is especially advantageous to include a tissue collection device when attempting a second cut. For example, the catheter may include a lumen or compartment at the distal end to retain the tissue. Likewise, under suction the device may include a tissue trap, such that fluid, blood, or other material may pass, but tissue is retained in the trap. The physician then may monitor the trap to determine that the tissue removed from the septum has been captured, and is not still in the heart. Such a monitoring may be automatically provided, or may be manual by the physician. It is advantageous if such monitoring can be conducted before the catheter is removed from the patient, and as such in one embodiment the trap is exterior to the body and readily accessible by the physician. In another embodiment, the trap is automatically monitored by a sensor, such as an electrode, visual examination, pressure sensor, or the like for the presence and volume of tissue.

Typically the device types described herein work best if there is no bias, or force on the tissue in any direction other than what is necessary to capture and cut. The exception is a device used to increase an existing holes size, in which case biasing the shaft and cutter into the side of the previous hole is necessary. In general though, if there is bias in or out of the septal plane during capture for instance, the tissue will likely be stretched over the capture components prior to capture, making the resulting hole smaller than expected. Likewise, if the bias is within the septal plane prior to capture, the device shaft will elongate or tear the hole such that the capture has minimal tissue on one side and bunched tissue on the other. If a cut is made in the latter situation, the cutter may pass through, on one side, the hole created by the bias, leaving an elongated hole. Also, if part of the cut passes through a hole stretched by bias, the tissue around the shaft will not be complete, creating an increased safety risk that would need mitigating.

Figure 18:
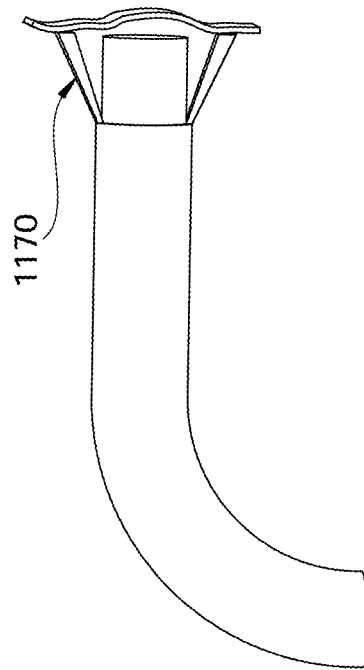
FIG. 18 is a partial perspective view of the distal end of a catheter constructed according to the present disclosure.

To remove bias—device stability, control and feedback is needed. Stability can be achieved at least three ways. First, a distal structure 1170 as in FIG. 18, attached to the outer sheath can engage the septal tissue, allowing all adjustments to be with respect to it. This frame structure may be at least partly disconnected from the proximal components to minimize unintended forces. The frame structure may consist of one or more struts extending from the catheter or sheath, designed to lean against the tissue and hold the catheter and cutter orthogonally to the tissue. Likewise, in another embodiment the structure may be a hood. A hood structure would also allow a suction to remove all blood and provide direct visualization of the septum. In another example the distal structure 1170 may be a balloon on the outer surface of the sheath, such that when inflated the balloon structure matches the contour of the septum and provides for an orthogonal guide to the sheath, catheter, or blade. In each case, the orthogonal guide is preferably collapsible for delivery into the atrium.

Second, the device, such as the sheath or catheter shaft, can be affixed securely to the patients puncture site via a catheter holder, allowing all adjustments to be with respect to the puncture site and therefore the septum. Finally, the catheter handle can be affixed to the patient, drape, bed rail mount/platform, or similar via a catheter holder.

A catheter holder would secure either the catheter shaft, catheter handle, or both. The combination of the catheter handle and catheter holder would secure and hold constant the catheter shaft, and therefore hold constant the distal end of the catheter tip, from rotation, bending, longitudinal movements, alignment, bias, tissue capture actuation and cutter operation. The operator could then control fine adjustable movements of the handle or catheter holder in order to make fine prescribed movements to the catheter distal tip, for more accurately and safely cutting a hole in the interatrial septum.

Since each of these progressively is further from the septum, they progressively become less stable. However, each is more stable than the clinician simply controlling localization with his hand. Control of the distal tip of the devices is achieved through the device rotation, shaft deflection, bending of the shaft, and actuation of the distal components. In some cases, for precise aperture creation, these critical control movements may be less than 1 mm, making the previously mentioned device stability critical. As input into the decision to manipulate the controls for proper aperture creation precise feedback is necessary. Feedback described above included, bias force sensing, tissue thickness sensing, device localization sensing, visual handle controls of distal catheter elements, as examples. Most of the control and feedback are in reference to some stable device reference point established somewhere along the catheter, as necessary to deliver a precise aperture quickly and safely.

In another embodiment, the cutting means is allowed to "float" with respect to the catheter, such that it is contact with the tissue that governs the orientation of the cutting means, rather than the orientation of the catheter. In particular, if the bottom side of a circular cutter contacts the tissue first, the cutter will pivot as its pushed forward, for example, so that only the top portion moves forward until the entire cutter is substantially in contact with the tissue. For example, in one embodiment the cutter may be attached to the medical device via a central shaft, and spaced from the catheter via springs around the periphery, such that under light pressure from the fossa, the cutter compresses one or more springs, but does not initially compress the others, causing the cutter face to move into an orthogonal position vis a vis the tissue. As the cutter comes fully into contact with the tissue, the pressure from the catheter continues to rise and it is pushed orthogonally through the tissue.

The invention claimed is:

1. A medical device assembly comprising:
   a sheath, the sheath comprising:
      an elongated sheath shaft, the sheath shaft having a first bend region, a central lumen and a distal end,
      a first steering wire, the steering wire having a first position and a second position, wherein at the first position the first bend region is substantially linear, and wherein at the second position the distal end of the sheath is substantially perpendicular to a longitudinal axis of the sheath,
   a catheter inside the sheath, the catheter comprising:
      a catheter shaft, the catheter shaft having a central lumen,
      a shaped blade, the shaped blade comprising:
         a blade cutting edge that is oriented at a substantially right angle to the longitudinal axis of the sheath when the sheath is oriented substantially perpendicular to the inter atrial septum, and is adapted to cut a 3 mm or larger durable aperture in the interatrial septum,
      a tissue articulator adapted to hold the interatrial septum.

2. The assembly of claim 1 further comprising a marker to identify the catheter location on a visualization system.

3. The assembly of claim 1, wherein the articulator is a suction device.

4. The assembly of claim 3, wherein the assembly does not comprise a component adapted to cross the interatrial septum such as a guidewire or needle.

5. The assembly of claim 3, wherein the articulator is adapted to retain the interatrial septum from only the same side of the interatrial septum as the shaped blade cuts the interatrial septum.

6. The assembly of claim 1 wherein the shaped blade is selected from the group consisting of a circular blade, a square blade, a triangular blade, a sawtoothed blade, a franseen blade, or a polygonal blade.

7. The assembly of claim 1 further comprising a tissue removal device.

8. The assembly of claim 7 wherein the tissue removal device is adapted to remove or hold a first tissue portion so that the articulator can hold a second tissue portion against the blade.

9. The assembly of claim 8 wherein the tissue removal device is a suction mechanism adapted to remove the first tissue portion.

10. The assembly of claim 1 wherein the articulator comprises a tissue removal device.

11. The assembly of claim 1 further comprising an anchor.

12. The assembly of claim 11 wherein the anchor attaches to the interatrial septum.

13. The assembly of claim 11 wherein the anchor attaches to one of the patient's exterior or the patient's bedside.

14. The assembly of claim 1 further comprising an orthogonal guide, the orthogonal guide adapted to hold the shaped blade in an orthogonal position to the interatrial septum.

15. The assembly of claim 1, further comprising an actuator operably connected to the tissue articulator, and
   wherein the tissue articulator has a first setting and a second setting, the tissue articulator being adapted to hold the interatrial septum against the shaped blade for cutting while in the second setting, and wherein the actuator has a first position and a second position, wherein when the actuator is in the second position the tissue articulator holds the interatrial septum against the shaped blade.

16. A medical device assembly comprising:
   a sheath, the sheath comprising:
      an elongated sheath shaft, the sheath shaft having a first bend region, a central lumen and a distal end,
      a first steering wire, the steering wire having a first position and a second position, wherein at the first position the first bend region is substantially linear, and wherein at the second position the distal end of the sheath is substantially perpendicular to a longitudinal axis of the sheath,
   a catheter inside the sheath, the catheter comprising:
      a catheter shaft,
      a shaped blade, the shaped blade comprising:
         a blade cutting edge that is oriented at a substantially right angle to the longitudinal axis of the sheath when the sheath is oriented substantially perpendicular to the inter atrial septum, and is adapted to cut a 3 mm or larger durable aperture in the interatrial septum,
      a tissue articulator, the tissue articulator having a first setting and a second setting, the tissue articulator being adapted to hold the interatrial septum against the shaped blade for cutting while in the second setting,
      an actuator connected to the tissue articulator, the actuator having a first position and a second position, wherein when the actuator is in the second position the tissue articulator holds the interatrial septum against the shaped blade.

17. The assembly of claim 16 further comprising a suction opening configured to provide suction in the approximate area of the shaped blade.

18. The assembly of claim 16 wherein the tissue articulator is a tapered cone having a proximal face, the proximal face being adapted to retain a tissue.

19. A method of treating a heart comprising the steps of:
- inserting a catheter into the right atrium of the heart, the catheter comprising:
  - a shaft,
  - a distal catheter lumen,
  - a shaped cutting blade arranged around the distal catheter lumen,
  - a tissue articulator, the tissue articulator having a first position and a second position,
  - an actuator connected to the tissue articulator
  - a steering mechanism
- while the catheter is in the right atrium, actuating the actuator to move the tissue articulator into a second position that holds the tissue against the shaped cutting blade,
- cutting an aperture in the interatrial septum between the right atrium and the left atrium,
- removing a cut tissue from the right atrium.

20. The method of claim 19 further comprising a step of attaching a tissue removal device to a portion of the interatrial septum.

\* \* \* \* \*